(12) United States Patent
Zhao et al.

(10) Patent No.: US 10,717,736 B2
(45) Date of Patent: Jul. 21, 2020

(54) PYRROLE AMIDES AS ALPHA V INTEGRIN INHIBITORS

(71) Applicant: BRISTOL-MYERS SQUIBB COMPANY, Princeton, NJ (US)

(72) Inventors: Guohua Zhao, Princeton, NJ (US); James Mignone, Hamilton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/347,826

(22) PCT Filed: Nov. 7, 2017

(86) PCT No.: PCT/US2017/060392
§ 371 (c)(1),
(2) Date: May 7, 2019

(87) PCT Pub. No.: WO2018/089360
PCT Pub. Date: May 17, 2018

(65) Prior Publication Data
US 2019/0256512 A1    Aug. 22, 2019

Related U.S. Application Data

(60) Provisional application No. 62/418,833, filed on Nov. 8, 2016.

(51) Int. Cl.
| | |
|---|---|
| *C07D 471/04* | (2006.01) |
| *A61K 31/4375* | (2006.01) |
| *A61P 1/16* | (2006.01) |
| *A61P 13/12* | (2006.01) |
| *A61P 11/00* | (2006.01) |
| *A61P 35/00* | (2006.01) |

(52) U.S. Cl.
CPC .............. *C07D 471/04* (2013.01); *A61P 1/16* (2018.01); *A61P 11/00* (2018.01); *A61P 13/12* (2018.01); *A61P 35/00* (2018.01)

(58) Field of Classification Search
CPC .............. C07D 471/04; C07D 403/14; A61K 31/4375; A61K 31/506
USPC ................... 546/122; 514/300, 256; 544/333
See application file for complete search history.

(56) References Cited

U.S. PATENT DOCUMENTS

| | | | |
|---|---|---|---|
| 5,760,029 A | 6/1998 | Jadhav et al. | |
| 6,090,944 A | 7/2000 | Hutchinson | |
| 6,114,328 A | 9/2000 | Wityak et al. | |
| 8,481,549 B2* | 7/2013 | Fatheree | C07D 401/04 514/255.05 |
| 2008/0045521 A1 | 2/2008 | Arnould et al. | |
| 2008/0255183 A1 | 10/2008 | Arnould et al. | |
| 2016/0264566 A1 | 9/2016 | DeGrado et al. | |

FOREIGN PATENT DOCUMENTS

| | | |
|---|---|---|
| WO | WO199926945 A1 | 6/1999 |
| WO | WO199930709 A1 | 6/1999 |
| WO | WO2002060438 A1 | 8/2002 |
| WO | WO2006108040 A1 | 10/2006 |
| WO | WO2007141473 A1 | 12/2007 |
| WO | WO2011098603 A1 | 8/2011 |
| WO | WO2014154725 A1 | 10/2014 |
| WO | WO2015091426 A1 | 6/2015 |
| WO | WO2016046225 A1 | 3/2016 |
| WO | WO2016046226 A1 | 3/2016 |
| WO | WO2016046230 A1 | 3/2016 |
| WO | WO2016046241 A1 | 3/2016 |
| WO | WO2016134223 A2 | 8/2016 |

* cited by examiner

Primary Examiner — Charanjit Aulakh
(74) Attorney, Agent, or Firm — Gary Greenblatt

(57) ABSTRACT

The present invention provides compounds of Formula (I) or stereoisomers, tautomers, or pharmaceutically acceptable salts or solvates thereof, wherein all the variables are as defined herein. These compounds are inhibitors to $\alpha_v$-containing integrins. This invention also relates to pharmaceutical compositions comprising these compounds and methods of treating a disease, disorder, or condition associated with dysregulation of αv-containing integrins, such as pathological fibrosis, transplant rejection, cancer, osteoporosis, and inflammatory disorders, by using the compounds and pharmaceutical compositions.

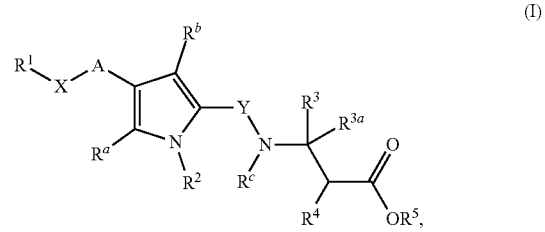

(I)

15 Claims, No Drawings

PYRROLE AMIDES AS ALPHA V INTEGRIN INHIBITORS

CROSS REFERENCE TO RELATED APPLICATION

This application is a national phase application under 35 U.S.C. § 371 of International Patent Application No. PCT/US2017/060392, filed Nov. 7, 2017, which claims priority to U.S. Provisional Application No. 62/418,833 filed Nov. 8, 2016, which are expressly incorporated fully herein by reference.

FIELD OF THE INVENTION

The present invention relates to substituted pyrrole amides as $\alpha_v$ integrin inhibitors, pharmaceutical compositions comprising such compounds and to their use in therapy, especially in the treatment or prophylaxis of diseases, disorders, and conditions for which an $\alpha_v$ integrin inhibitor is indicated in a human.

BACKGROUND OF THE INVENTION

Integrins belong to a large family of a/(3 heterodimeric transmembrane proteins that are involved in cell adhesion to a wide variety of extracellular matrix proteins, cell-cell interactions, cell migration, proliferation, survival, and in maintenance of tissue integrity (Barczyk et al. *Cell and Tissue Research* 2010, 339, 269; Srichai, M. B.; Zent, R. in *Cell-Extracellular Matrix Interactions in Cancer*, 2010). In mammals, there are 24α/β integrin heterodimers known from various combinations of 18 alpha and 8 beta subunits. Transforming Growth Factor-β (TGF-β) has a central role in driving a number of pathological processes underlying fibrosis, cell growth, and autoimmune diseases. Alpha V ($\alpha_v$) Integrins, that include $\alpha_v\beta 1$, $\alpha_v\beta 3$, $\alpha_v\beta 5$, $\alpha_v\beta 6$, and $\alpha_v\beta 8$, are involved in a critical pathway that leads to the conversion of latent TGF-β to its active form (Henderson, N. C.; Sheppard, D. *Biochim, Biophys. Acta* 2013, 1832, 891). Thus, antagonism of such $\alpha_v$ integrin-mediated activation of latent TGF-β provides a viable therapeutic approach to intervene in TGF-β-driven pathological states (Sheppard, D. *Eur. Resp. Rev.* 2008, 17, 157; Goodman, S. L.; Picard, M. *Trends Pharmacol. Sciences* 2012, 33(7), 405; Hinz, B. *Nature Medicine* 2013, 19(12), 1567; Pozzi, A.; Zent, R. *J. Am. Soc. Nephrol.* 2013, 24(7), 1034). All five $\alpha_v$ integrins belong to a small subset (8 out of 24) of integrins that recognize the Arginine-Glycine-Aspartic acid (RGD) motif present in their native ligands such as fibronectin, vitronectin, and Latency-Associated Peptide (LAP).

The expression of $\alpha_v$ integrin subtypes varies significantly. For example, $\alpha_v\beta 6$ is expressed on epithelial cells at very low levels in healthy tissue but is significantly upregulated during inflammation and wound healing. $\alpha_v\beta 3$ and $\alpha_v\beta 5$ are expressed on osteoclasts, endothelial, smooth muscle, and solid tumor cells, as well as on pericytes and podocytes, while $\alpha_v\beta 1$ is expressed on activated fibroblasts and mesangial cells.

Fibrotic conditions that represent major unmet medical needs are Idiopathic Pulmonary Fibrosis (IPF), liver and kidney fibrosis, Non-Alcoholic Fatty Liver Disease (NAFLD), Non-Alcoholic Steato-Hepatitis (NASH), as well as systemic sclerosis. Two drugs, pirfenidone and nintedanib, that act by non-integrin-mediated mechanisms, have recently been approved for treatment of IPF. The present invention relates to compounds that inhibit or antagonize the action of one or more of the $\alpha_v$ integrins in the treatment of pathological conditions, such as fibrosis and cancer, mediated by these integrins.

A number of selective or nonselective small molecule, peptidic, and antibody-based inhibitors of $\alpha_v$ integrins have been reported in the literature (Kapp, T. G. et al. *Expert Opin. Ther. Patents* 2013, 23(10), 1273; O'Day, S. et al. *Brit. J. Cancer* 2011, 105(3), 346; Pickarski, M. et al. *Oncol. Rep.* 2015, 33, 2737; Wirth, M. et al. *Eur. Urol.* 2014, 897; Henderson, N. C. et al. *Nature Medicine* 2012, 19(12), 1617; Horan, G. S. et al. *Am. J. Resp. Crit. Care Med.* 2008, 177, 56; Puthawala, K. et al. *Am. J. Resp. Crit. Care Med.* 2008, 177, 82; Reed, N. I. et al. *Sci. Transl. Med.* 2015, 7(288), 288ra79; Anderson, N. A. et al. WO 2014/154725 A1, WO 2016/046225 A1, WO 2016/046226 A1, WO 2016/046230 A1, WO 2016/046241 A1).

SUMMARY OF THE INVENTION

In one aspect, the present invention provides compounds of Formula (I) as well as the subgenera and species thereof, including stereoisomers, tautomers, pharmaceutically acceptable salts, and solvates thereof, which are useful as $\alpha_v$ integrin inhibitors.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with dysregulation of $\alpha_v$-containing integrins in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used for the manufacture of a medicament for the treatment of a disease, disorder, or condition associated with dysregulation of $\alpha_v$-containing integrins in a patient.

Other features and advantages of the invention will be apparent from the following detailed description and claims.

DETAILED DESCRIPTION OF THE INVENTION

The present application provides compounds, including all stereoisomers, solvates, prodrugs and pharmaceutically acceptable salt and solvate forms thereof, according to Formula I. The present application also provides pharmaceutical compositions containing at least one compound according to Formula I, or or a stereoisomer, a tautomer, or a pharmaceutically acceptable salt or a solvate thereof, and optionally at least one additional therapeutic agent. Additionally, the present application provides methods for treating a patient suffering from an $\alpha_v$ Integrin-modulated disease or disorder such as for example, Idiopathic Pulmonary Fibrosis (IPF), liver and kidney fibrosis, Non-Alcoholic Fatty Liver Disease (NAFLD), Non-Alcoholic Steato-Hepatitis (NASH), cardiac fibrosis, and systemic sclerosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides, inter alia, a compound of Formula (I):

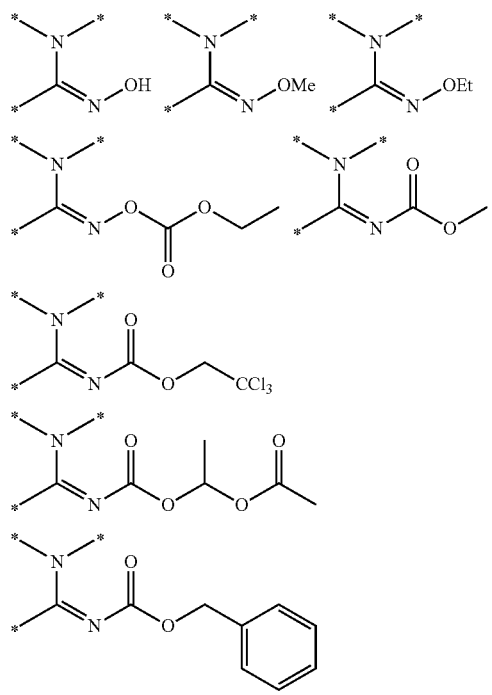

or a stereoisomer, a tautomer, or a pharmaceutically acceptable salt or solvate thereof, wherein:

A is a covalent bond, O, S, NH, —O—(C$_{1-3}$ alkylene)-, —S—(C$_{1-3}$ alkylene)- or —NH—(C$_{1-3}$ alkylene)-, wherein the C$_{1-3}$ alkylene is each independently substituted with 0, 1, or 2 R$^{7a}$;

X is absent or C$_{1-5}$ linear alkylene substituted with 0, 1, 2, or 3 R$^{7b}$;

Y is C(O) or C(R$^{6a}$R$^{6b}$);

R$^1$ is an Arginine mimetic moiety selected from the group consisting of

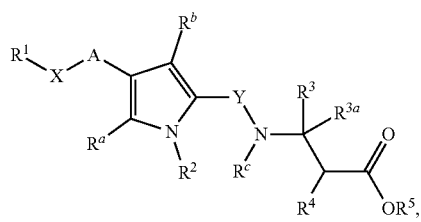

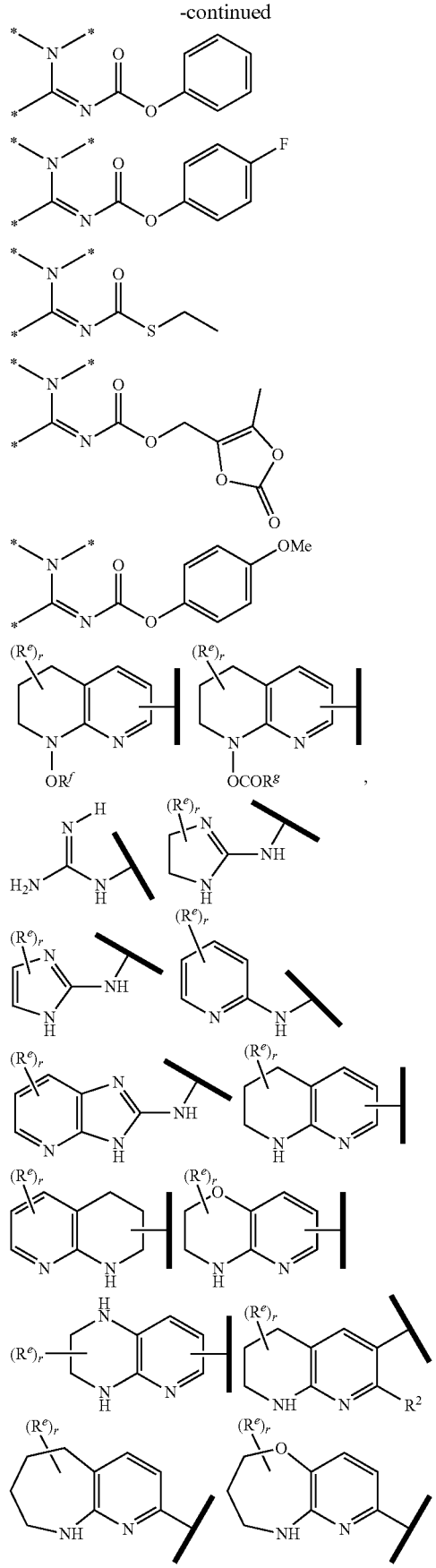

-continued one of the asterisks in each of the arginine mimetics moiety is an attachment point to X and the other two asterisks are hydrogen;

$R^e$ is OH, amino, amido, carbamate, sulfonamide, $C_{1-4}$ alkyl, halo, $C_{1-4}$ haloalkyl, or $C_{3-6}$ cycloalkyl;

$R^f$=H, $CH_3$, $CH_2CH_3$, $C(O)OCH_2CH_3$;

$R^g$=$CH_3$, $CH_2CH_3$, $CH_2CCl_3$, phenyl, 4-fluorophenyl, 4-methoxyphenyl, benzyl, r is an integer of 0, 1, 2, or 3;

$R^2$ is hydrogen or $C_{1-6}$ alkyl;

$R^3$ is hydrogen, $C_{1-6}$ alkyl, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$;

$R^{3a}$ is hydrogen; or alternatively, $R^{3a}$ and $R^3$, together with the atom or atoms to which they are attached, form a 3- to 6-membered carbocyclic or heterocyclic ring which is optionally substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^4$ is hydrogen, $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^9$;

n is an integer of 1 or 2;

$R^5$ is hydrogen, $R^{5a}$, or a structural moiety selected from $L^1$ and $L^2$ are each independently $C_{1-4}$ alkylene;

$R^{5a}$ and $R^{5b}$ are each independently $C_{1-6}$ alkyl, phenyl, benzyl, or 5- to 7-membered heterocyclyl; wherein the alkyl, phenyl, and heterocyclyl are each independently substituted with 0 to 3 $R^{5d}$;

$R^{5c}$ is $C_{1-6}$ alkyl or 5- to 7-membered carbocyclyl; wherein the alkyl, phenyl, and heterocyclyl are each independently substituted with 0 to 3 $R^{5d}$;

$R^{5d}$, at each occurrence, is independently halo, OH, alkoxy, oxo, or alkyl; or alternatively, two adjacent $R^{5d}$, together with the atoms to which they are attached, form a carbocyclyl moiety;

$R^{6a}$ and $R^{6b}$ are each independently hydrogen or $C_{1-6}$ alkyl;

$R^{7a}$ and $R^{7b}$ are each independently halo, cyano, hydroxyl, amino, $C_{1-6}$ alkyl, haloalkyl, hydroxyalkyl, aminoalkyl, alkoxy, haloalkoxy, amido, carbamate, or sulfonamide;

$R^8$ is each independently halo, cyano, OH, $NR^aR^b$, $C_{1-6}$ alkyl, alkoxy, alkylamino, haloalkyl, haloalkoxy, haloaminoalkyl, hydroxyalkyl, aminoalkyl, alkylsulfonyl (e.g., —$S(O)_2R'$), sulfonamide (e.g., —$S(O)_2NR'R''$), 3 to 6 membered carbocyclyl, 3 to 6 membered heterocyclyl, 6- to 10-membered aryl, or 5- to 10-membered heteroaryl; or alternatively, two $R^8$ at adjacent positions, together with the atoms to which they are attached, form a carbocyclyl or heterocyclyl; wherein the aryl and heteroaryl are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^9$ at each occurrence is independently halo, cyano, OH, $NR^aR^b$, $C_{1-6}$ alkyl, alkoxy, alkylamino, haloalkyl, haloalkoxy, haloaminoalkyl, hydroxyalkyl, aminoalkyl, alkylsulfonyl (e.g., —$S(O)_2R'$), sulfonamide (e.g., —$S(O)_2NR'R''$), 3 to 6 membered carbocyclyl, 3 to 6 membered heterocyclyl, 6- to 10-membered aryl, or 5- to 10-membered heteroaryl; or alternatively, two $R^9$ at adjacent positions, together with the atoms to which they are attached, form a carbocyclyl or heterocyclyl; wherein the aryl and heteroaryl are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{10}$ is $C_{1-6}$ alkyl, 3- to 10-membered carbocyclyl, 3- to 10-membered heterocyclyl, 6- to 10-membered aryl, or 5- to 10-membered heteroaryl; wherein the alkyl, carbocyclyl, heterocyclyl are each independently substituted with 0, 1, 2, or 3 $R^{11}$;

$R^{11}$ is halo, cyano, hydroxyl, amino, amino, amido, carbamate, sulfonamide, $C_{1-6}$ alkyl, alkoxy, 3- to 10-membered carbocyclyl, 3- to 10-membered heterocyclyl, 6- to 10-membered aryl, or 5- to 10-membered heteroaryl; wherein the aryl, alkyl, cycloalkyl, heteroaryl, and cycloheteroalkyl are each independently substituted with 0, 1, 2, or 3 $R^{12}$;

$R^a$, $R^b$, and $R^c$, at each occurrence, are independently hydrogen, $C_{1-10}$ alkyl, 3- to 10-membered carbocyclyl, or 3- to 10-membered heterocyclyl; wherein the alkyl, carbocyclyl, heterocyclyl are each independently substituted with 0, 1, 2, or 3 $R^{13}$; and $R^{12}$ and $R^{13}$, at each occurrence, are independently halo, cyano, OH, amino, $C_{1-6}$ alkyl, alkoxy, alkylamino, haloalkyl, haloalkoxy, haloaminoalkyl, 3 to 6 membered carbocyclyl, or 3 to 6 membered heterocyclyl, 6- to 10-membered aryl, or 5- to 10-membered heteroaryl; wherein the aryl and heteroaryl are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide.

In one embodiment of Formula (I), $C(R^{6a}R^{6b})$ is $CHR^{6b}$, while in another embodiment, $C(R^{6a}R^{6b})$ is $CH_2$.

In one embodiment of Formula (I), $R^c$ is hydrogen or $C_{1-6}$ alkyl.

In one embodiment of Formula (I), Y is C(O).

In one embodiment of Formula (I), X is $C_{2-4}$ linear alkylene.

In one embodiment of Formula (I), $R^1$ is selected from a structural formula selected from the group consisting of

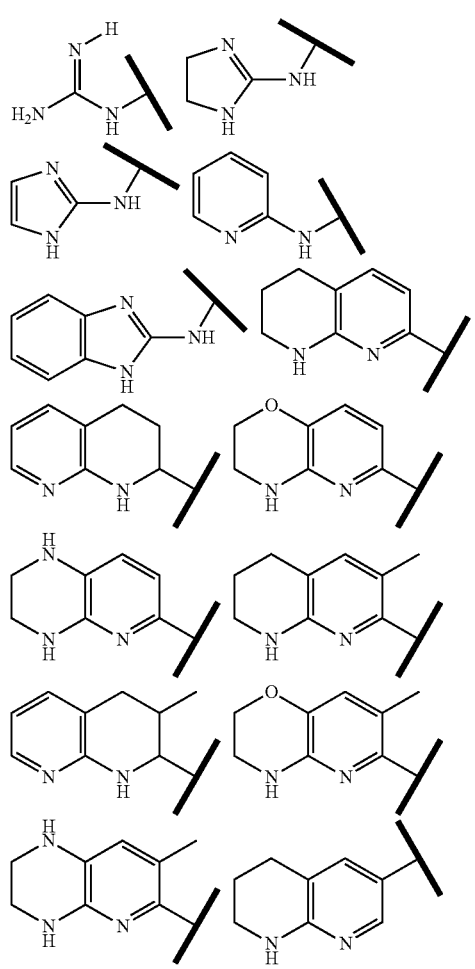

In one embodiment of Formula (I), $R^3$ and $R^4$ are not both hydrogen.

In one embodiment of Formula (I), $R^4$ is hydrogen; and $R^3$ is 3- to 10-membered carbocyclyl, 6- to 10-membered aryl, 3- to 14-membered heterocyclyl, 5- to 14-membered heteroaryl, wherein the carbocyclyl, heterocyclyl, aryl, and heteroaryl are each independently substituted with 0, 1, 2, or 3 $R^8$.

In one embodiment of Formula (I), $R^3$ is hydrogen; and $R^4$ is $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$.

In one embodiment of Formula (I), R³ is selected from the group consisting of hydrogen,
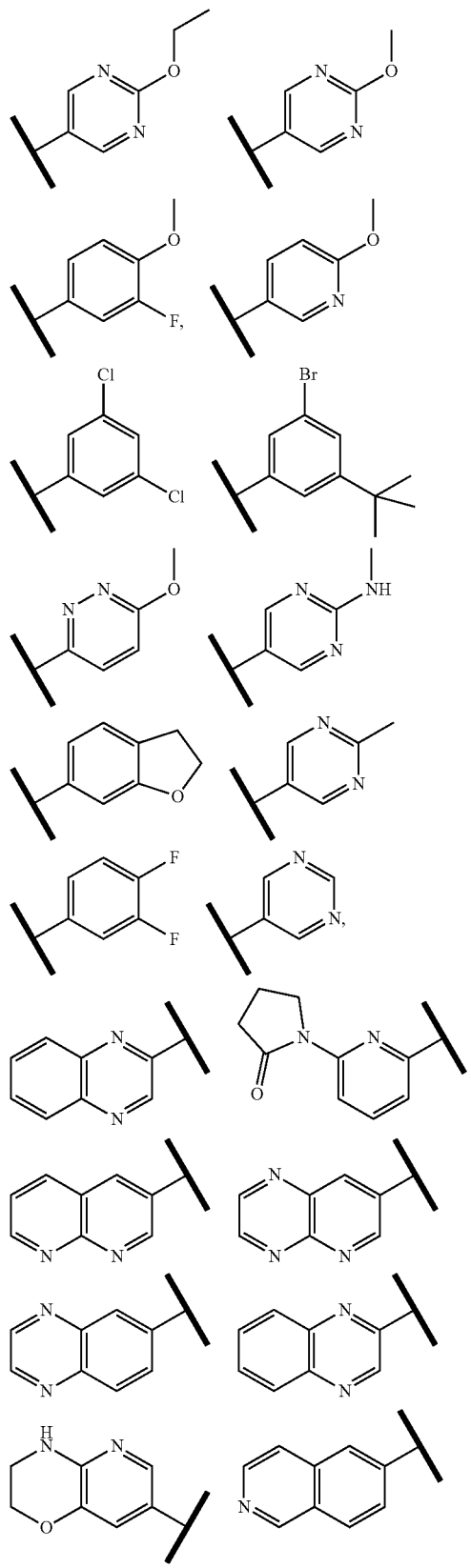
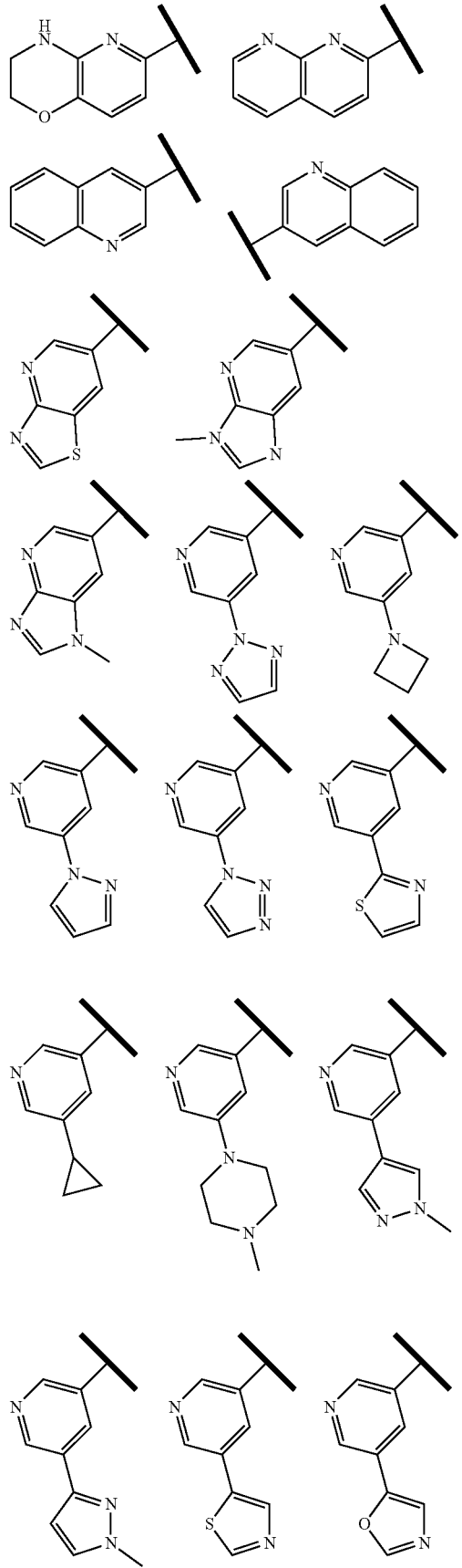
-continued -continued
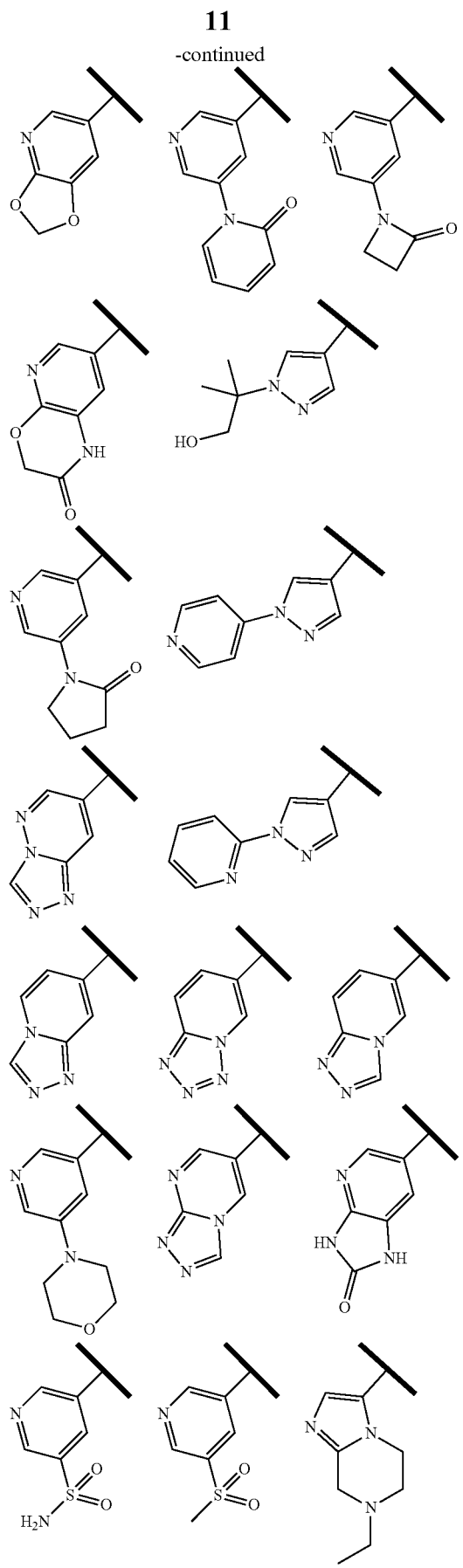
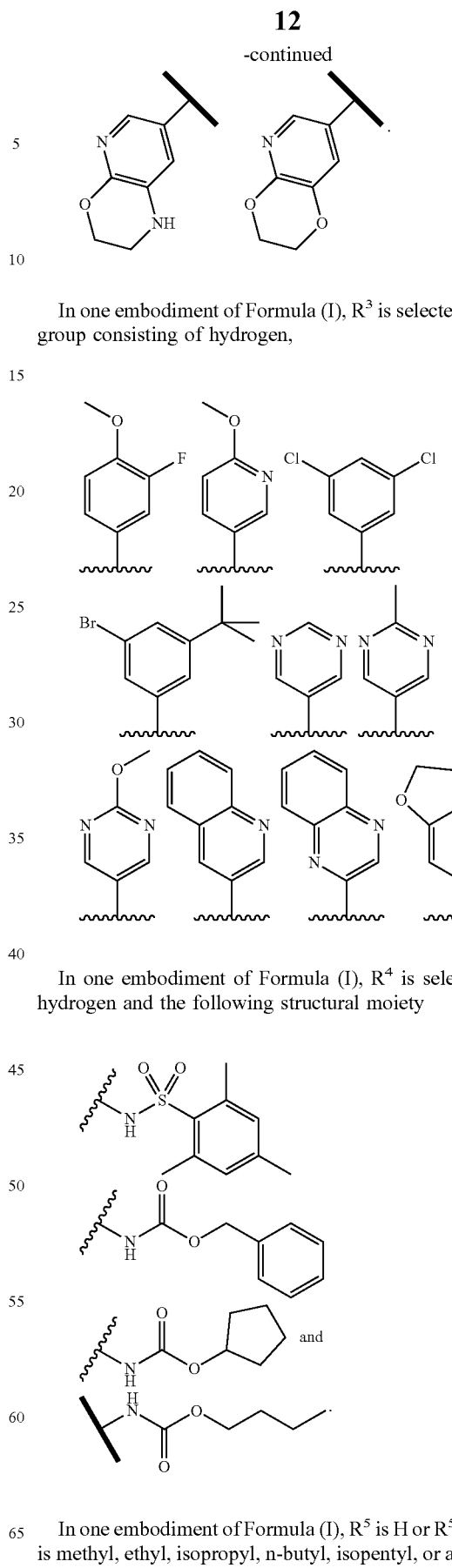
In one embodiment of Formula (I), R³ is selected from the group consisting of hydrogen,
In one embodiment of Formula (I), R⁴ is selected from hydrogen and the following structural moiety
In one embodiment of Formula (I), R⁵ is H or R⁵ᵃ; and R⁵ᵃ is methyl, ethyl, isopropyl, n-butyl, isopentyl, or a structural moiety selected from

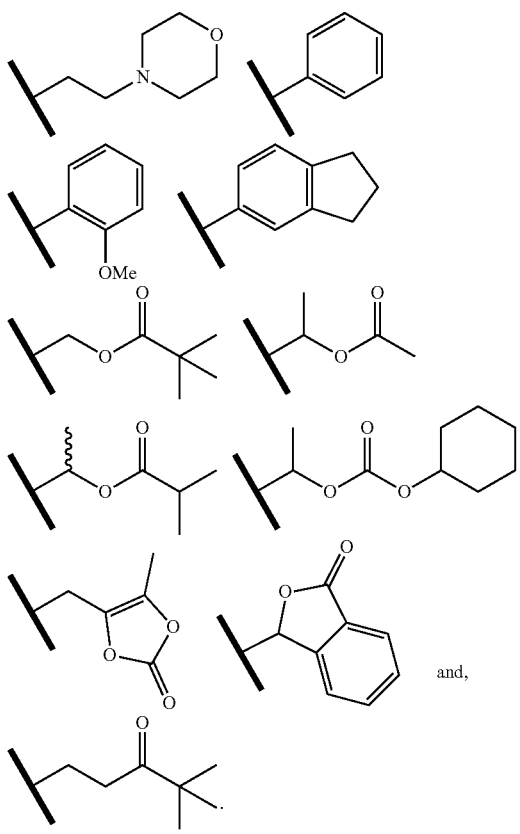

In one embodiment of Formula (I), $R^2$ is H; and $R^5$ is H.

In any one embodiment of Formula (I), the compound is selected from any one of the Examples as described in this specification, or a stereoisomer, a tautomer, or a pharmaceutically acceptable salt or solvate thereof.

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of $\alpha_v$ integrins in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an integrin receptor antagonizing effect in a patient comprising administering a therapeutically effective amount of a compound of the present invention, or a stereoisomer, a tautomer, or a pharmaceutically acceptable salt or solvate thereof, to the patient. In one embodiment, the integrin receptor antagonizing effect is an antagonizing effect to any of $\alpha_v\beta6$, $\alpha_v\beta1$, $\alpha_v\beta3$, $\alpha_v\beta5$, and $\alpha_v\beta8$; or a combination of one or more of $\alpha_v\beta6$, $\alpha_v\beta1$, $\alpha_v\beta3$, $\alpha_v\beta5$, and $\alpha_v\beta8$. For example, the integrin receptor antagonizing effect can be an $\alpha_v\beta6$, $\alpha_v\beta1$, $\alpha_v\beta3$, $\alpha_v\beta5$, and $\alpha_v\beta8$ antagonizing effect.

In some embodiments, the disease, disorder, or condition is associated with fibrosis, including pulmonary, liver, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of $\alpha_v$ integrins that can be prevented, modulated, or treated according to the present invention include, but are not limited to, transplant injection, fibrotic disorders (e.g., idiopathic pulmonary fibrosis (IPF), interstitial lung disease, liver fibrosis, kidney fibrosis, skin fibrosis, systemic sclerosis), inflammatory disorders (e.g., acute hepatitis, chronic hepatitis, non-alcoholic steatohepatitis (NASH), psoriasis, irritable bowel syndrome (IBS), inflammatory bowel disease (IBD)), osteoporosis, as well as cell-proliferative disorders (e.g., cancer, myeloma, fibroma, hepatocarcinoma, leukemia, Kaposi's sarcoma, solid tumors).

The fibrotic disorders, inflammatory disorders, as well as cell-proliferative disorders that are suitable to be prevented or treated by the compounds of the present invention include, but are not limited to, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, non-alcoholic fatty liver disease (NAFLD), alcoholic or non-alcoholic steatohepatitis (NASH), acute hepatitis, chronic hepatitis, liver cirrhosis, primary sclerosing cholangitis, drug-induced hepatitis, biliary cirrhosis, portal hypertension, regenerative failure, liver hypofunction, hepatic blood flow disorder, nephropathy, pneumonia, psoriasis, irritable bowel syndrome (IBS), inflammatory bowel disease (IBD), abnormal pancreatic secretion, benign prostatic hyperplasia, neuropathic bladder disease, spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocarcinoma, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$α_vβ6$ monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol,
3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic (β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as Idiopathic Pulmonary Fibrosis (IPF), liver and kidney fibrosis, Non-Alcoholic Fatty Liver Disease (NALFD), Non-Alcoholic Steato-Hepatitis (NASH), cardiac fibrosis, and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for examplee SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997), ACC inhibitors (for example, CP-640186 and NDI-010976), FGF21 agonist (for example, LY2405319 and BMS-986036), caspase inhibitors (for example, emricasan), NOX4 inhibitors (for example, GKT137831), MGAT2 inhibitor (for example, BMS-963272), and bile acid/fatty acid conjugates (for example aramchol). The $α_v$ inhibitors of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL: 3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., FXR agonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the av integrins. Such compounds may be provided in a commercial kit, for example, for use in pharmaceutical research involving $\alpha_v$ integrins activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by any one of Formula (I), (IIa), (IIb), (IIc), (IId), (IIe), (IIIa), (IIIb), (IVa) and (IVb), or a stereoisomer, a tautomer, or a pharmaceutically acceptable salt or solvate thereof.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —S(O)$_2$R', while sulfonamide may be represented by —S(O)$_2$NR$^c$R$^d$. R' is $C_1$ to $C_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR'R", wherein R' and R" are independently H or $C_{1-6}$ alkyl; or alternatively, R' and R", taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When R$^c$ or R$^d$ (or both of them) is $C_{1-6}$ alkyl, the amino group can also be referred to as alkylamino. Examples of alkylamino group include, without limitation, —NH$_2$, methylamino, ethylamino, propylamino, isopropylamino and the like.

The term "aminoalkyl" refers to an alkyl group on which one of the hydrogen atoms is replaced by an amino group. For example, aminoalkyl may be represented by N(R$^c$R$^d$)-alkylene-. "$C_1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, CF$_3$CH$_2$, CF$_3$ or CF$_3$CF$_2$CH$_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, CF$_3$CH$_2$O, CF$_3$O or CF$_3$CF$_2$CH$_2$O.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

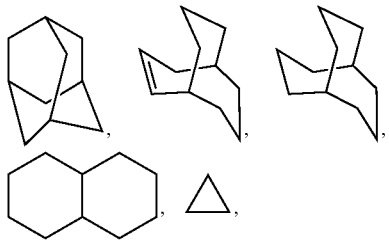

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4- thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

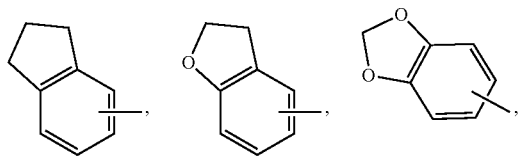

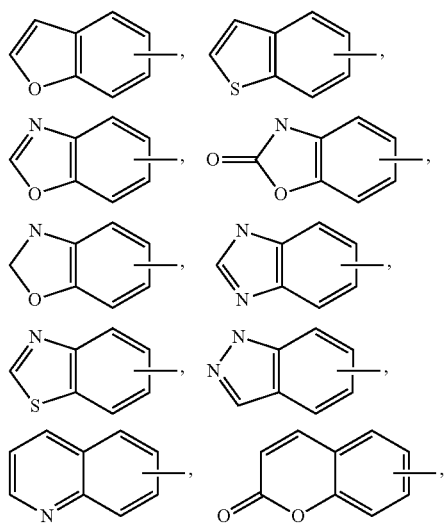

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy bond in a structural formula, such as

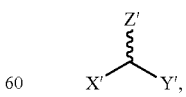

is used to depict a stereogenic center of the carbon atom to which X', Y', and Z' are attached and is intended to represent both enantiomers in a single FIGURE. That is, a structural formula with such as wavy bond denotes each of the enantiomers individually, such as

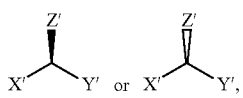

as well as a racemic mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a dotted ring is used within a ring structure, this indicates that the ring structure may be saturated, partially saturated or unsaturated.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

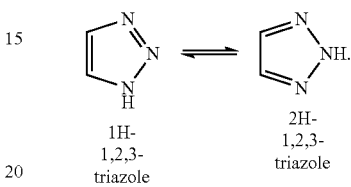

1H-1,2,3-triazole     2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Examples of such prodrug esters include:

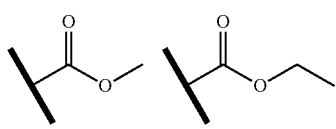

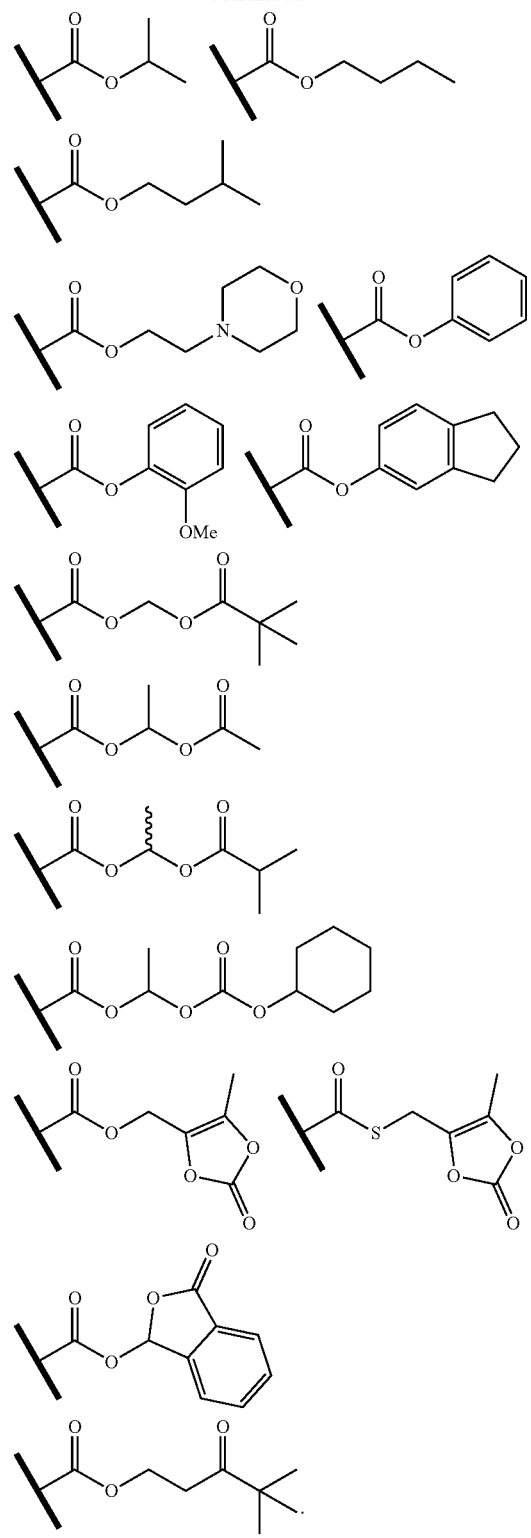

The compounds of the present invention contain an arginine mimetics moiety which can form physiologically hydrolyzable esters that serve as prodrugs, i.e., "prodrugs of arginine mimetics", by being hydrolyzed in the body to yield the compounds of the present invention per se. Representative examples of prodrugs of arginine mimetics include:

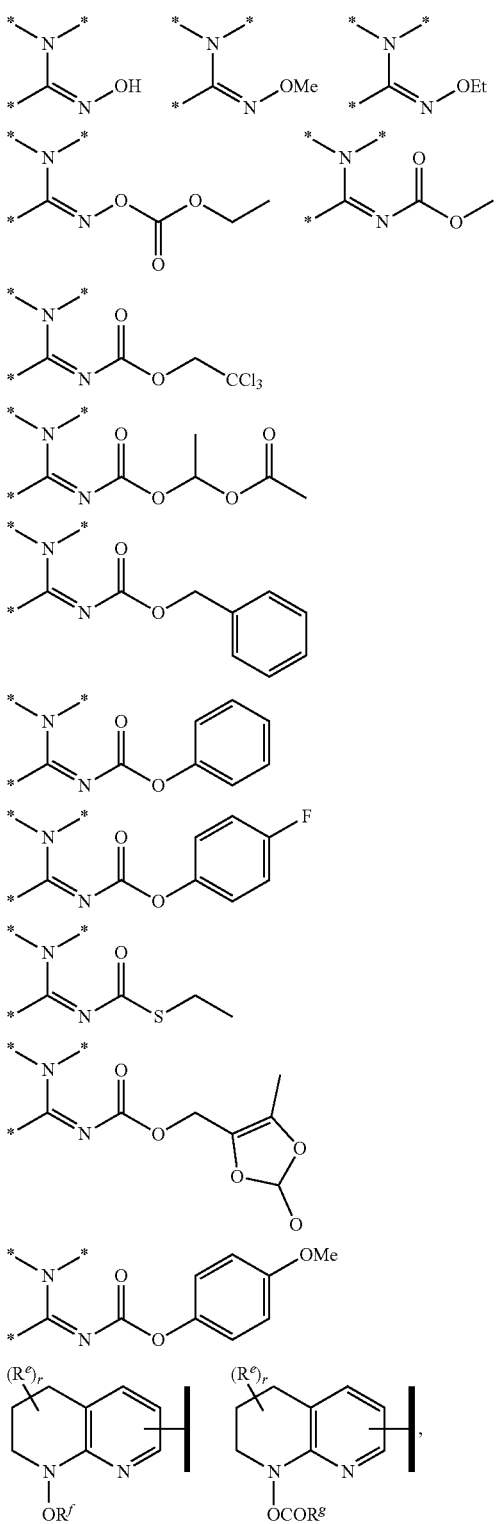

wherein, one of the asterisks in each of the arginine mimetics moiety is an attachment point to the parent molecule and the other two asterisks are hydrogen; $R^f$=H, Me, Et, COOEt; $R^g$=$CH_3$, $CH_2CH_3$, $CH_2CCl_3$, phenyl, 4-fluorophenyl, 4-methoxyphenyl, benzyl, $R^e$ is OH, $C_{1-4}$ alkyl, halo, haloalkyl, or $C_{1-4}$ cycloalkyl; and r is an integer of 0, 1, 2, or 3.

Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112: 309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
ACN acetonitrile
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA diethylamine
DMP or Dess-Martin 1,1,1-tris(acetyloxy)-1,1-dihydro-1,2-beniziodoxol-3-(1H)-one Periodinane
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexanes
HOBt or HOBT 1-hydroxybenzotriazole
H$_2$O$_2$ hydrogen peroxide
IBX 2-iodobenzoic acid
H$_2$SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MSCl methanesulfonyl chloride
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$COOH ammonium formate
NMM N-methylmorpholine
OTf triflate or trifluoromethanesulfonate
Pd$_2$(dba)$_3$ tris(dibenzylideneacetone)dipalladium(O)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride PPTS pyridinium p-toluenesulfonate
i-PrOH or IPA isopropanol
PS Polystyrene
PtO$_2$ platinum oxide
rt room temperature
SEM-Cl 2-(trimethysilyl)ethoxymethyl chloride
SiO$_2$ silica oxide
SnCl$_2$ tin(II) chloride
TBAI tetra-n-butylammonium iodide
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane
pTsOH p-toluenesulfonic acid
TsCl p-tolunesulfonyl chloride IV. Methods of Preparation The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., *Comprehensive Organic Transformations*, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., *Comprehensive Organic Transformations*, VCH, New York (1989).

Generic Schemes

The pyrrole analogs of Formula (I') can be prepared according to the general routes shown in Schemes 1 to 4 using methods known in the literature. Depending on the particular molecule of Formula (I') being prepared, $R^1$—X-A-, $R^2$, $R^3$, $R^{3a}$, $R^4$, $R^a$, $R^b$, and $R^c$ can either be fully installed prior to or elaborated after assemblage of the pyrrole amide structure of Formula (I'). As shown in Scheme 1, pyrrole ester 4 can be synthesized from pyrrole ester 1 via Suzuki reaction or Stille reaction as described in *Tetrahedron Lett.* 2003, 44, 427 (Handy, et al.). Alternatively pyrrole ester 4 can be made either from the corresponding methyl 1H-pyrrole-2-carboxylate by synthetic transformations known to those skilled in the art or via the cyclization of vinamidinium salt 2 and glycine ester 4 using the procedures of Gupton et al. *J. Org. Chem.* 1990, 55, 4735. Vinamidinium salt 2 is either commercially available or can be synthesized by using the procedures of Davies et al. *J. Org. Chem.* 2001, 66, 251 (hexafluorophosphate salts) or the procedures of Arnold et al. *Collect. Czech. Chem. Commun.* 1973, 38, 2633 (perchlorate salts). Pyrrole carboxylic acid 5 may be synthesized by the saponification of pyrrole ester 4 with a base such as NaOH, KOH or LiOH, in solvent such as EtOH or MeOH, followed by acidification with an acid such as HCl or H$_2$SO$_4$. Compounds of Formula (I'), when Y═CO and $R^5$═H, can be obtained by the amide bond formation between amino ester 6 with pyrrole carboxylic acid 5 using one of the variety of procedures conducive to amide formation known to those skilled in the art and subsequent deprotection of the resulting carboxylic ester. Amino ester 6 can be prepared using the methods known in the literature (for example, Hutchinson, J. H. et al. *J. Med Chem.* 2003, 46, 4790; Henderson, N. C. et al. *Nature Medicine* 2013, 19, 1617). Compounds of formula (I'), when Y═CR$^{6a}$R$^{6b}$; and $R^5$═H, can be prepared by alkylating amino ester 6 with pyrrole 7 or via a reduction amination of pyrrole aldehyde/ketone 8 and amino ester 6, followed by deprotection of the resulting carboxylic ester. Pyrrole 7 can be made from pyrrole ester 4, pyrrole carboxylic acid 5, or pyrrole aldehyde/ketone via reduction to the alcohol by a suitable reagent and conversion to a leaving group such as a mesylate, tosylate, or a halide represented by 7. The transformation from pyrrole ester 4 or pyrrole carboxylic acid 5 to pyrrole aldehyde/ketone 8 can be achieved by employing the procedures readily known to those skilled in the art.

Scheme 1
General scheme for the preparation of compounds of Formula (I') ($R^5$ = H)
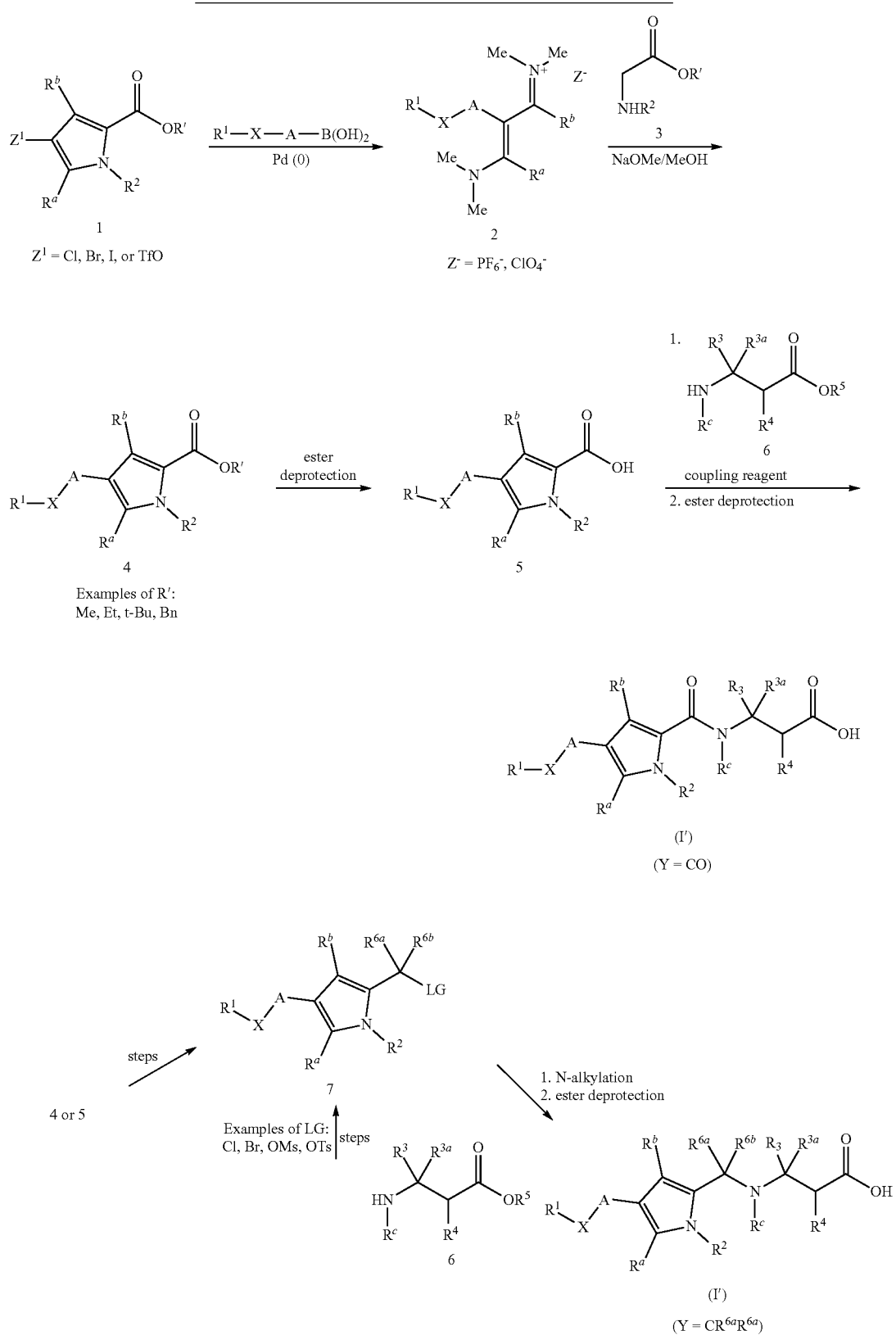

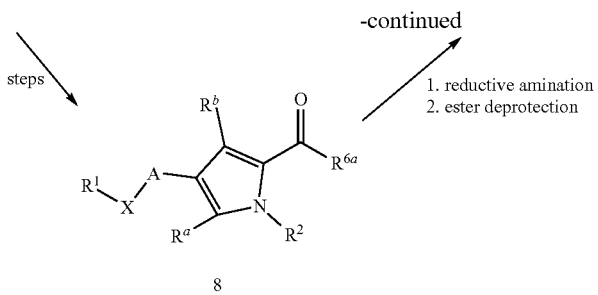

8

Syntheses of compounds of Formula (I') (Y=CO; $R^5$=H; Formulas 15, and 16) which contain tetrahydronaphthyridines as Arginine mimetics are illustrated in Scheme 2. Pyrrole ester 1 can be converted to ketone ester 11 by coupling with a) ketone alkene 9 or b) hydroxylalkyl alkene 10 under standard Heck coupling conditions (Felpin, F.-X.; Nassar-Hardy, L.; Le Callonnec, F.; Fouquet, E. *Tetrahedron* 2011, 67, 2815-2831) and subsequent oxidation of the resulting alcohol. Naphthyridine ester 12 can be formed by the condensation of ketone ester 11 with 2-amino-3-formylpyridine under Friedlander conditions (Jose Marco-Contelles; Elena Perez-Mayoral; Abdelouahid Samadi; Maria do Carmo Carreiras; Elena Soriano (2009). "Recent Advances in the Friedlander Reaction". *Chemical Reviews*. 109 (6): 2652-2671), or by coupling with naphthyridinyl alkene 13 under standard Heck coupling conditions. Naphthyridine amide 14 can be obtained by coupling of the resulting carboxylic acid from the deprotection of naphthyridine ester 12 with amino ester 6 using one of the variety of amide formation procedures known to those skilled in the art. Tetrahydronaphthyridine acids 15 (major) and 16 (minor) can be synthesized by the selective ring reduction of 14 in the presence of a catalyst such as $PtO_2$ and the subsequent deprotection of the resulting carboxylic ester. Tetrahydronaphthyridine acids 15 and 16 can also be prepared by the condensation of aldehyde ester 17 with a starting material having a pre-formed naphthyridine ring, such as methyl naphthyridine, in the presence of a sulfonamide, such as p-tosylamide (Yizhe Yan; Kun Xu; Yang Fang; and Zhiyong Wang. *J. Org. Chem.* 2011, 76, 6849-6855), and subsequently employing the method similar to the one used for the conversion of 12 to 15 and 16. Alternatively, 15 and 16 can be synthesized by the selective ring reduction of 12 or 18 to give tetrahydronaphthyridine esters 19 (major) and 20 (minor) followed by the transformations similar to those used for the conversion of 12 to 15 and 16.

Scheme 2

General scheme for the preparation of compounds of Formula (I') (Y = CO: $R^5$ = H; Formula 15 and 16) with tetrahydronaphthyridine as an Arginine mimetic (R1)

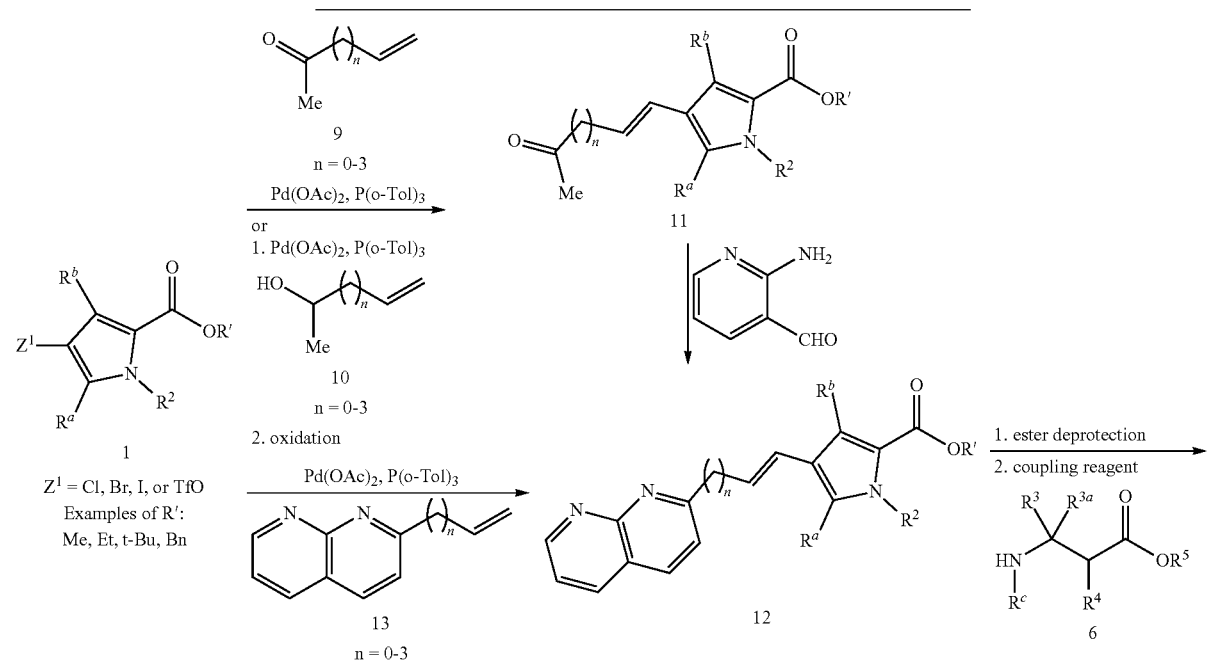

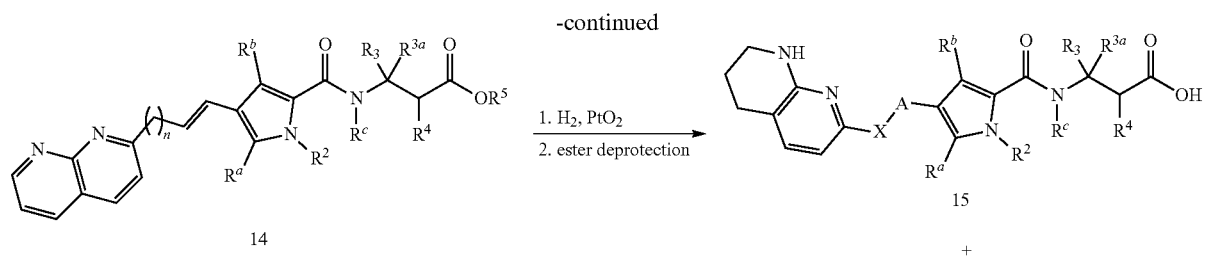

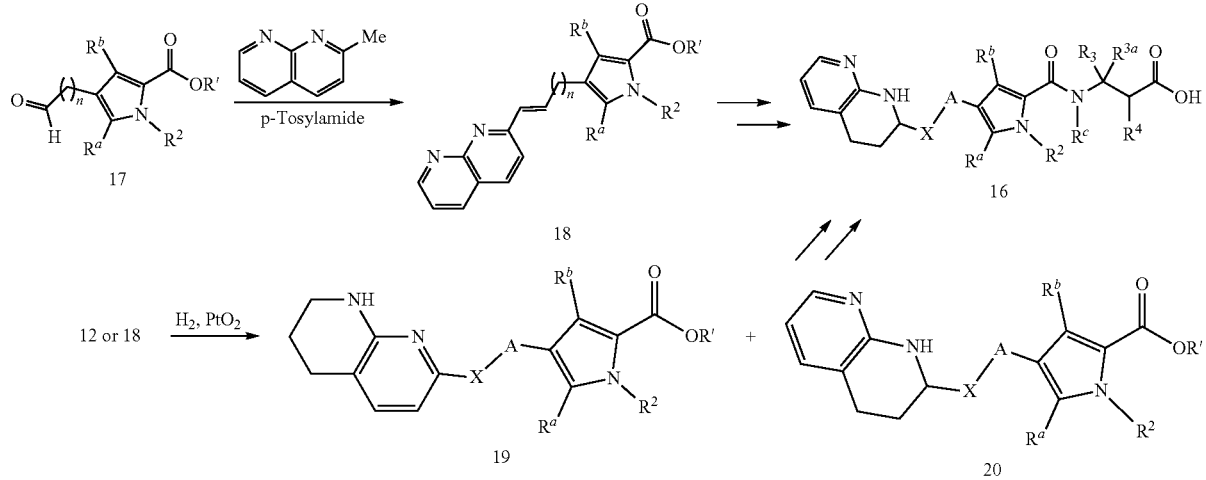

Scheme 3

Example of the synthesis of compounds of Formula (I')
(Y = CO; R⁵ = H; Formula 25) with 2-aminopyridine as an Arginine mimetic (R¹):

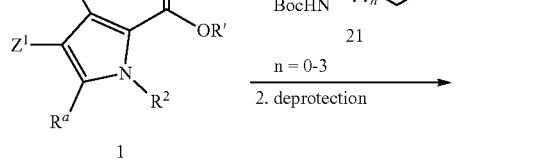

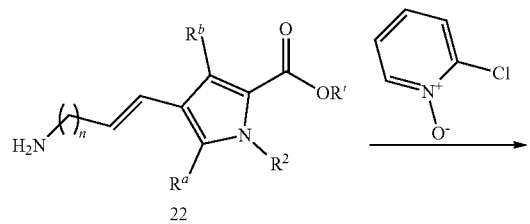

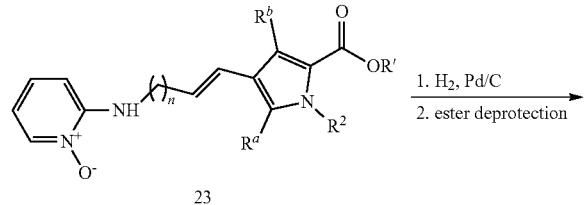

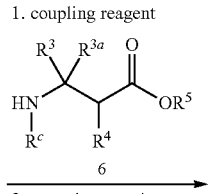

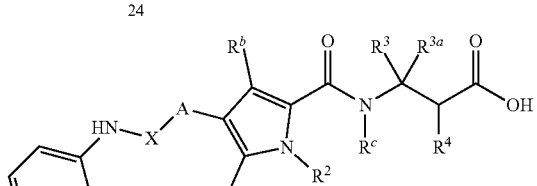

Scheme 3 describes an example of the synthesis of compounds of Formula (I') (Y=CO; R⁵=H; Formula 25) with 2-aminopyridine as an Arginine mimetic. Amino ester 22 can be prepared from pyrrole ester 1 by coupling with protected amino alkene 21 under Heck reaction conditions and subsequent deprotection. N-oxide 23 can be formed by the nucleophilic substitution of 2-chloropyridine oxide with amino ester 22. Aminopyridine acid 24 can be made by the reduction of N-oxide 23 in the presence of Pd/C followed by ester deprotection. Aminopyridine acid 25 can be obtained by the amide bond formation between amino ester 6 with aminopyridine acid 24 and subsequent deprotection of the resulting carboxylic ester.

Scheme 4

Example of the synthesis of compounds of Formula (I')
(Y = CO; R⁵ = H; Formula 29) with 2-aminodihydroimidazole as an Arginine mimetic (R¹):

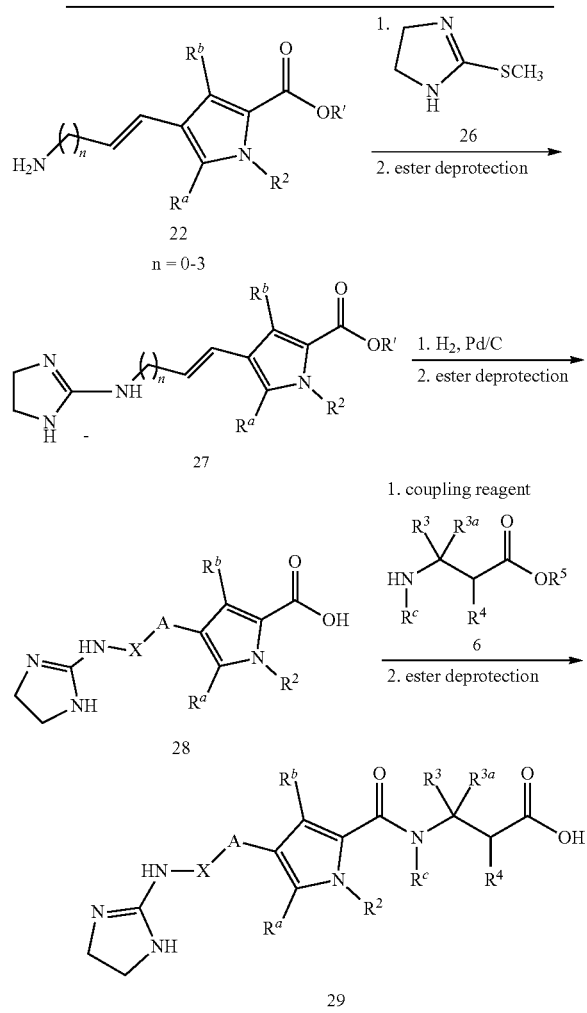

An example of the synthesis of compounds of Formula (I') (Y=CO; R⁵=H; Formula 29) with 2-aminodihydroimidazole as an Arginine mimetic is outlined in Scheme 4. Aminodihydroimidazole ester 27 can be made by the reaction of amino ester 22, described earlier, with a suitable electrophile such as 2-(methylthio)-4,5-dihydro-1H-imidazole followed by ester deprotection. Aminodihydroimidazole acid 28 can be prepared by the reduction of the double bond of aminodihydroimidazole ester 27 in the presence of Pd/C followed by ester deprotection. Aminopyridine acid 29 can be obtained by the amide bond formation between amino ester 6 with aminodihydroimidazole acid 28 and subsequent deprotection of the resulting carboxylic ester.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. ¹HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

Analytical HPLC Method #1: Phenomenex® Luna 5μ C18 4.6×50 mm, 4 min gradient, 10% MeOH/90% H₂O/0.1% H₃PO₄ to 90% MeOH/10% H₂O/0.1% H₃PO₄, 1 min hold; 4 mL/min, UV detection at 220 nm.

Analytical HPLC Method #2: YMC s5 Combiscreen ODS 6×50 mm, 4 min gradient, 10% ACN/90% H₂O/0.1% TFA to 90% ACN/10% H₂O/0.1% TFA, 1 min hold; 4 mL/min, UV detection at 220 nm.

Intermediate 1

Ethyl (S)-3-amino-3-(3-fluoro-4-methoxyphenyl)propanoate, HCl

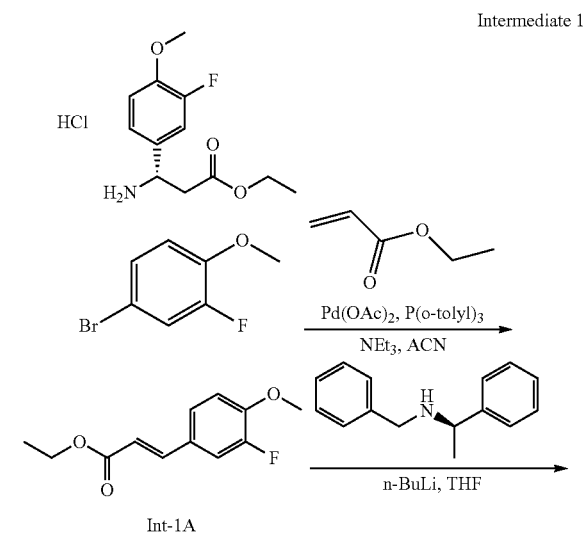

Int-1A

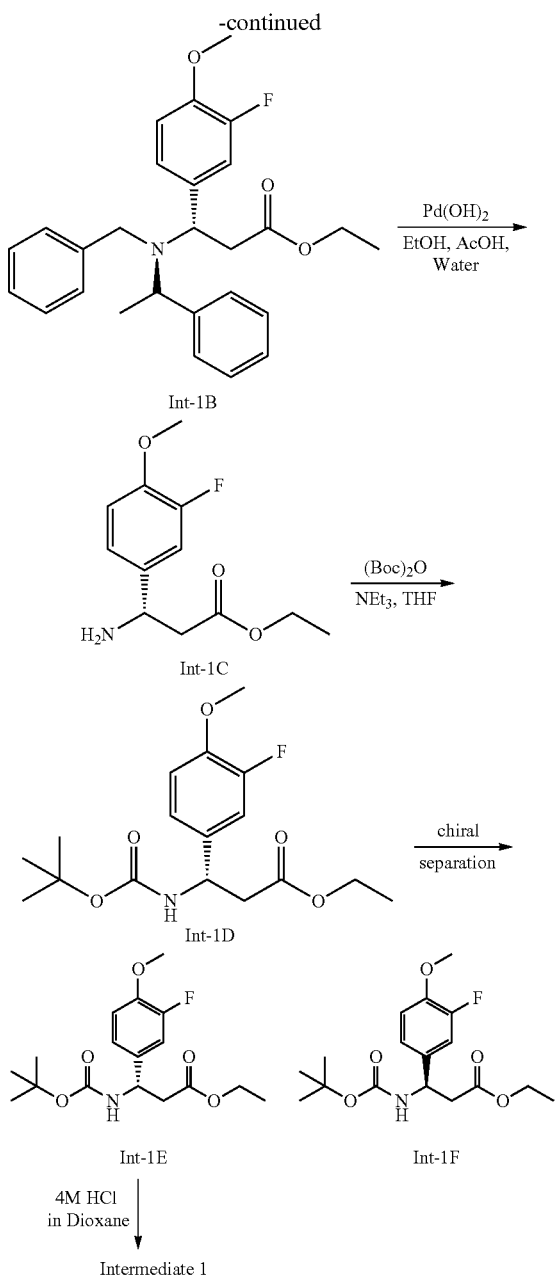

Int-1A, Int-1B, and Int-1C were prepared according to the procedure described in: Hutchinson, J. H. et al., *J. Med. Chem.* 2003, 46, 4790.

Int-1A. Ethyl (E)-3-(3-fluoro-4-methoxyphenyl)acrylate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 225.1 [M+H]$^+$.

Int-1B. Ethyl (S)-3-(benzyl((S)-1-phenylethyl)amino)-3-(3-fluoro-4-methoxyphenyl)propanoate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 436.2 [M+H]$^+$.

Int-1C. Ethyl (S)-3-amino-3-(3-fluoro-4-methoxyphenyl) propanoate: $^1$HNMR (500 MHz, CDCl$_3$) δ 7.13 (dd, J=12.2, 2.1 Hz, 1H), 7.07 (dt, J=8.3, 1.5 Hz, 1H), 6.92 (t, J=8.5 Hz, 1H), 4.37 (t, J=6.7 Hz, 1H), 4.15 (qd, J=7.1, 1.0 Hz, 2H), 3.88 (s, 3H), 2.65-2.55 (m, 2H), 1.25 (t, J=7.2 Hz, 3H). LCMS (ES): m/z 242.1 [M+H]$^+$.

Int-1D. Ethyl (S)-3-(tert-butoxycarbonyl)amino)-3-(3-fluoro-4-methoxyphenyl)propanoate: To a solution of Int-1C (31.75 g, 132 mmol) in THF (189 mL) at 0° C. were added triethylamine (20.18 mL, 145 mmol) and (Boc)$_2$O (30.6 mL, 132 mmol). The reaction mixture was warmed to room temperature and stirred for 18.5 h whereupon it was diluted with EtOAc. The reaction mixture was washed with water, 10% citric acid and brine. The organic layer was dried over anhydrous Na$_2$SO$_4$, concentrated and dried under vacuum to give Int-1D.

Int-1E. (S)-Ethyl 3-((tert-butoxycarbonyl)amino)-3-(3-fluoro-4-methoxyphenyl)propanoate: Int-1D was purified by preparative chiral SFC (Column: Whelko-RR (5×50 cm, 10 uM, #4080), BPR Pressure: 100 bars, Temperature: 35° C., Flow rate: 300 mL/min, Mobile Phase: CO$_2$/MeOH (70/30), Detector Wavelength: 220 nm; Separation Program: stack injection; Injection: 4 mL with cycle time: 2 mins; Sample preparation: 44.4 g/310 mL MeOH:DCM (9:1), 143.2 mg/mL; Throughput: 16.3 g/hr) to afford Int-1E (41.1 g, 91%) as a white solid: $^1$H NMR (500 MHz, CDCl$_3$) δ 7.09-6.97 (m, 2H), 6.94-6.87 (m, 1H), 5.47 (br. s., 1H), 5.03 (br. s., 1H), 4.09 (q, J=7.2 Hz, 2H), 3.88 (s, 3H), 2.92-2.70 (m, 2H), 1.44 (s, 9H), 1.20 (t, J=7.2 Hz, 3H). LCMS (ES): m/z 364 [M+Na]$^+$. >99% ee. [α]$_D^{20}$–27.36° (c 1.54, CHCl$_3$).

Int-1F. Ethyl (R)-3-((tert-butoxycarbonyl)amino)-3-(3-fluoro-4-methoxyphenyl)propanoate: The above preparative chiral SFC separation yielded Int-1F (1.5 g, 3%) as a white solid: $^1$H NMR (500 MHz, CDCl$_3$) δ 7.10-6.97 (m, 2H), 6.95-6.86 (m, 1H), 5.47 (br. s., 1H), 5.02 (d, J=8.0 Hz, 1H), 4.09 (q, J=7.0 Hz, 2H), 3.88 (s, 3H), 2.91-2.69 (m, 2H), 1.47-1.37 (m, 9H), 1.20 (t, J=7.2 Hz, 3H). LCMS (ES): m/z 364.1 [M+Na]$^+$. 96.4% ee. [α]$_D^{20}$+20.76° (c 1.54, CHCl$_3$).

Intermediate 1: A solution of Int-1E (1.0 g, 2.93 mmol) in 4 M HCl in dioxane (48 mL) was stirred at room temperature for 1 h. The solvent was removed in vacuo and the residue was air-dried under vacuum. The residue was then dissolved in EtOH (10 mL), concentrated in vacuo and dried under vacuum to yield Intermediate 1 (0.801 g, 98%) as a white solid. $^1$H NMR (500 MHz, CDCl$_3$) δ 8.80 (br. s., 3H), 7.37-7.28 (m, 2H), 6.95 (t, J=8.5 Hz, 1H), 4.68 (t, J=6.9 Hz, 1H), 4.08 (q, J=7.1 Hz, 2H), 3.88 (s, 3H), 3.22 (dd, J=16.6, 6.2 Hz, 1H), 3.00 (dd, J=16.5, 7.7 Hz, 1H), 1.18 (t, J=7.2 Hz, 3H). LCMS (ES): m/z 242.1 [M+H]$^+$. >99% ee. [α]$_D^{20}$+ 11.82° (c 1.54, CHCl$_3$).

Intermediate 2

Ethyl (R)-3-amino-3-(3-fluoro-4-methoxyphenyl) propanoate, HCl

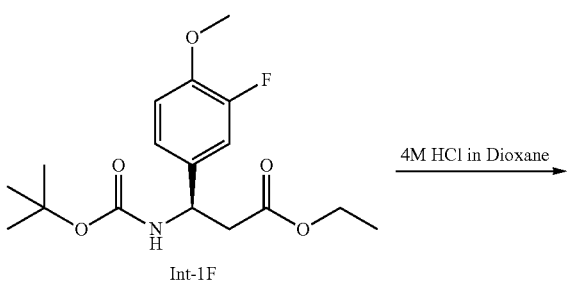

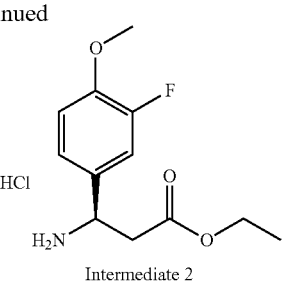

Intermediate 2

Intermediate 2: Using the procedure described for synthesis of Intermediate 1, Int-1F (1.5 g, 4.39 mmol) and 4 M HCl in dioxane (48 mL) yielded Intermediate 2 (1.16 g, 95%) as a white solid: $^1$H NMR (500 MHz, CDCl$_3$) δ 8.81 (br. s., 3H), 7.37-7.27 (m, 2H), 7.01-6.88 (m, 1H), 4.68 (br. s., 1H), 4.08 (q, J=7.1 Hz, 2H), 3.88 (s, 3H), 3.23 (dd, J=16.6, 6.2 Hz, 1H), 3.01 (dd, J=16.6, 7.6 Hz, 1H), 1.18 (t, J=7.0 Hz, 3H). LCMS (ES): m/z 242.1 [M+H]$^+$. 96.4% ee. $[α]_D^{20}$ –11.26° (c 1.54, CHCl$_3$).

Intermediate 3

Ethyl (S)-3-amino-3-(6-methoxypyridin-3-yl)propanoate

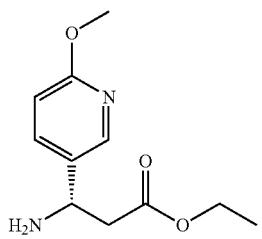

Intermediate 3

Intermediate 3 was prepared using the procedure described for Intermediate 1. $^1$H NMR (500 MHz, CDCl$_3$) δ 8.14 (d, J=2.2 Hz, 1H), 7.66 (dd, J=8.5, 2.5 Hz, 1H), 6.75 (d, J=8.5 Hz, 1H), 4.46 (dd, J=8.8, 5.0 Hz, 1H), 4.15 (q, J=7.2 Hz, 2H), 3.93 (s, 3H), 2.82 (dd, J=16.2, 8.8 Hz, 1H), 2.72-2.56 (m, 1H), 1.24 (t, J=7.2 Hz, 3H). HPLC retention time (Method #1): 1.132 min.; LCMS (ES): m/z 225.0 [M+H]$^+$.

Intermediate 4

Ethyl (R)-3-amino-3-(3-bromo-5-(tert-butyl)phenyl)propanoate

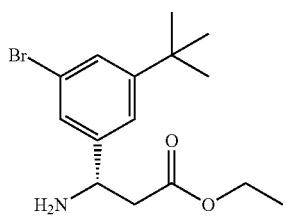

Intermediate 4

Intermediate 4 was prepared according to the procedure described in: Henderson, N. C. et. al., *Nature Medicine* 2013 19, 1617.

Intermediate 5

Methyl 3-amino-3-(3,5-dichlorophenyl)propanoate

Intermediate 6

Methyl (S)-3-amino-3-(3,5-dichlorophenyl)propanoate

Intermediate 7

Methyl (R)-3-amino-3-(3,5-dichlorophenyl)propanoate

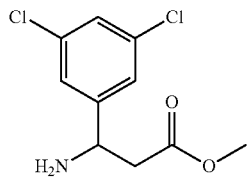

Intermediate 5

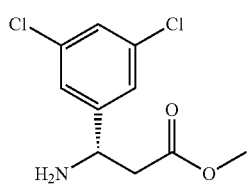

Intermediate 6

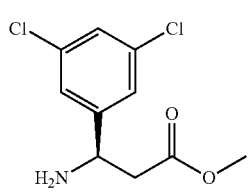

Intermediate 7

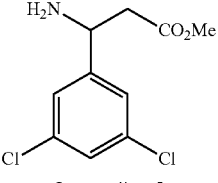

Intermediate 5

Int-5A: 3-Amino-3-(3,5-dichlorophenyl)propanoic acid: A mixture of ammonium acetate (14.09 g, 183 mmol), 3,5-dichlorobenzaldehyde (8.0 g, 45.7 mmol) and malonic acid (5.23 g, 50.3 mmol) in EtOH (90 mL) was heated at reflux for 16 h. After cooling to room temperature, the solid was collected by filtration, washed with EtOH (15 mL), and dried (anhydrous MgSO$_4$) to give crude Int-5A (7.0 g, 66%) as a white solid. LCMS (ES): m/z 234.3 [M+H]$^+$.

Intermediate 5: To a mixture of Int-5A (7.0 g, 29.9 mmol) in MeOH (50 mL) was added SOCl$_2$ (5.02 mL, 68.8 mmol). The reaction mixture was stirred at room temperature for 6 h. The solid was removed by filtration. The filtrate was concentrated in vacuo to give a crude product which was dissolved in EtOAc (150 mL). The organic layer was washed with sat. NaHCO$_3$ solution, brine, dried (anhydrous MgSO$_4$), filtered, and concentrated under reduced pressure to afford the crude product which was purified by flash chromatography (silica gel, CH$_2$Cl$_2$:MeOH, 100:0 to 95:5) to afford Intermediate 5 (3.3 g, 46%) as a yellow oil: $^1$H NMR (500 MHz, CDCl$_3$) δ 7.31 (d, J=1.9 Hz, 2H), 7.28 (t, J=1.9 Hz, 1H), 4.44 (t, J=6.7 Hz, 1H), 3.69 (s, 3H), 2.81-2.63 (m, 2H). LCMS (ES): m/z 248.3 [M+H]$^+$.

Intermediate 6: Intermediate 5 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: CO$_2$/MeOH (95/5)+0.1% DEA, Detector wavelength: 220 nm) to afford Intermediate 6 (2.3 g) as a yellow oil. $^1$H NMR (500 MHz, CDCl$_3$) δ 7.28 (d, J=1.9 Hz, 1H), 7.26 (t, J=1.9 Hz, 1H), 4.43-4.34 (m, 1H), 3.70 (s, 3H), 2.76-2.56 (m, 2H).

Intermediate 7: Intermediate 5 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: CO$_2$/MeOH (95/5)+0.1% DEA, Detector wavelength: 220 nm) to afford Intermediate 7 (1.31 g) as a yellow oil. $^1$H NMR (500 MHz, CDCl$_3$) δ 7.27 (d, J=1.9 Hz, 1H), 7.26 (t, J=1.9 Hz, 1H), 4.38 (dd, J=8.7, 4.8 Hz, 1H), 3.70 (s, 3H), 2.65 (dd, J=16.0, 4.8 Hz, 1H), 2.60 (dd, J=16.0, 8.7 Hz, 1H).

Intermediate 8

(S)-Ethyl 3-amino-3-(2,3-dihydrobenzofuran-6-yl)propanoate

Intermediate 8

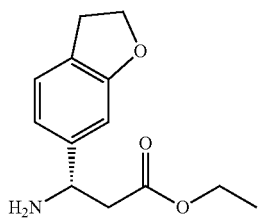

Intermediate 8 was prepared according to the procedure described for Intermediate 1. $^1$H NMR (400 MHz, DMSO-d$_6$) δ 7.17-7.10 (m, 1H), 6.86-6.74 (m, 2H), 4.49 (t, J=8.8 Hz, 2H), 4.19 (t, J=7.0 Hz, 1H), 4.06-3.94 (m, 2H), 3.12 (t, J=8.8 Hz, 2H), 2.70-2.54 (m, 3H), 1.21-1.05 (m, 3H). $^{13}$C NMR (400 MHz, DMSO-d$_6$) δ 171.13, 159.75, 146.24, 125.43, 124.37, 118.21, 106.80, 70.80, 59.62, 52.61, 44.12, 28.79, 14.02. LCMS (ES): m/z 236.0 [M+H]$^+$. [α]$_D^{25\,C}$ 6.0° (c 0.10 in CHCl$_3$).

Intermediate 9

Ethyl (S)-3-amino-3-(2-methoxypyrimidin-5-yl)propanoate

Intermediate 9

Int-9A was prepared according to the procedure described in Int-1A. $^1$H NMR (400 MHz, CDCl$_3$) δ 8.68 (s, 2H), 7.58 (d, J=16.0 Hz, 1H), 6.46 (d, J=16.0 Hz, 1H), 4.28 (q, J=7.0 Hz, 2H), 4.06 (s, 3H), 1.35 (t, J=7.0 Hz, 3H). LCMS (ES): m/z 209.0 [M+H]$^+$.

Intermediate 9: tert-Butyl alcohol (300 mL) was purged with ammonia keeping the temperature between 0-20° C. for 1 h. The ammonia purged tert-butyl alcohol and Int-9A (20 g, 96 mmol) were added to an 1 L autoclave. The reaction was heated at 80° C. for 30 h. The reaction was cooled to room temperature. The reaction mixture was removed from autoclave and concentrated. The crude solid was triturated with the diethyl ether and filtered. The filtrate was concentrated and purified by ISCO (5% methanol in chloroform) to yield the racemate (5.9 g). The racemate was further purified by SFC (Chiralpak IA (250×4.6) mm, 5u; % CO$_2$: 80%; % Co solvent: 20%(0.2% DEA in Methanol); Total Flow: 120.0 g/min; Back Pressure: 100 bars; Temperature: 30° C.; Detection: UV at 220 nm) to yield Intermediate 9 (2.3 g, 10%) as the first-eluting isomer. $^1$H NMR (300 MHz, DMSO-d$_6$) δ 8.58 (s, 2H), 4.20 (t, J=7.2 Hz, 1H), 4.02 (q, J=6.9 Hz, 2H), 3.89 (s, 3H), 2.67 (dd, J=7.2, 4.9 Hz, 2H), 2.09 (br s, 2H), 1.13 (t, J=7.2 Hz, 3H). LCMS (ES): m/z 226.2 [M+H]$^+$.

Intermediate 10

(S)-Ethyl 3-amino-3-(2-methylpyrimidin-5-yl)propanoate

Intermediate 10

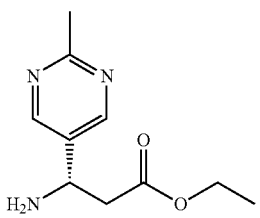

Intermediate 10 was prepared according to the procedure described for Intermediate 9. $^1$H NMR (400 MHz, DMSO-$d_6$) δ 8.66 (s, 2H), 4.20 (t, J=7.3 Hz, 1H), 4.05-3.98 (m, 2H), 2.68 (dd, J=7.0, 5.0 Hz, 2H), 2.57 (s, 3H), 2.09 (br s, 2H), 1.15-1.09 (m, 3H). LCMS (ES): m/z 210.2 [M+H]$^+$.

Intermediate 11

(S)-Ethyl 3-amino-3-(pyrimidin-5-yl)propanoate

Intermediate 11

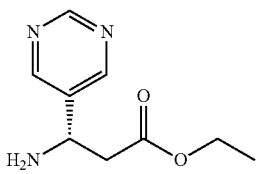

Intermediate 11 was prepared according to the procedure described for Intermediate 9. $^1$H NMR (300 MHz, DMSO-$d_6$) δ 9.05 (s, 1H), 8.80 (s, 2H), 4.24 (t, J=7.20 Hz, 1H), 4.01 (q, J=6.90 Hz, 2H), 2.74 (q, J=3.90 Hz, 2H), 1.11 (t, J=6.90 Hz, 3H). LCMS (ES): m/z 196.2 [M+H]$^+$.

Intermediate 12

Ethyl 3-amino-3-(2-methylpyrimidin-5-yl)propanoate (racemate)

Intermediate 12

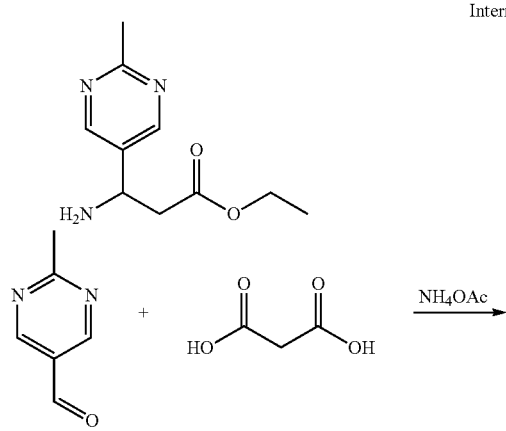

-continued

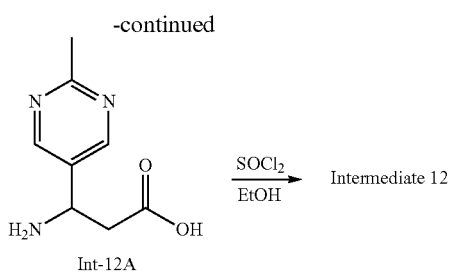

Int-12A. 3-Amino-3-(2-methylpyrimidin-5-yl)propanoic acid: A mixture of commercially available 2-methylpyrimidine-5-carbaldehyde (1.00 g, 8.19 mmol), malonic acid (1.28 g, 12.3 mmol) and ammonium acetate (1.58 g, 20.5 mmol) in EtOH (6.55 mL) were heated to 80° C. for 4 h. The reaction mixture was cooled to rt and the precipitate was collected by filtration, washed with cold EtOH and dried under vacuum to yield Int-12A (1.08 g, 73%) as an off-white solid which was used in the next step without further purification. $^1$H NMR (500 MHz, D$_2$O) δ 8.79 (s, 2H), 4.75-4.73 (m, 1H), 3.01-2.92 (m, 1H), 2.90-2.82 (m, 1H), 2.70 (s, 3H). HPLC retention time (Method #2): 0.168 min.; LCMS (ES): m/z 182.1 [M+H]$^+$.

Intermediate 12: SOCl$_2$ (0.185 mL, 2.54 mmol) was added dropwise to a room temperature solution of Int-12A (0.200 g, 1.10 mmol) in EtOH (2.90 mL) and the reaction mixture was stirred at room temperature overnight. The solvent was removed in vacuo and the residue was dissolved in DCM, washed with sat. NaHCO$_3$, water and brine. The organic layer was dried over anhydrous Na$_2$SO$_4$ and concentrated. The residue was purified by flash chromatography (silica gel, DCM:MeOH, 100:0 to 90:10) to yield Intermediate 12 (0.115 g, 50%) as a light yellow oil. $^1$H NMR (500 MHz, CDCl$_3$) δ 8.68 (s, 2H), 4.47 (dd, J=8.0, 5.5 Hz, 1H), 4.16 (q, J=7.2 Hz, 2H), 2.79-2.58 (m, 5H), 1.25 (t, J=7.2 Hz, 3H). HPLC retention time (Method #2): 0.317 min.; LCMS (ES): m/z 210.1 [M+H]$^+$.

Intermediate 13

Ethyl 3-amino-3-(2-methoxypyrimidin-5-yl)propanoate (racemate)

Intermediate 13

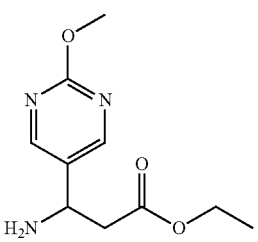

Intermediate 13 was prepared using the procedure described for Intermediate 12. $^1$H NMR (500 MHz, CDCl$_3$) δ 8.54 (s, 2H), 4.46-4.39 (m, 1H), 4.16 (q, J=7.2 Hz, 2H), 4.01 (d, J=0.6 Hz, 3H), 2.75-2.60 (m, 2H), 1.25 (t, J=7.2 Hz, 3H). HPLC retention time (Method #2): 0.490 min.; LCMS (ES): m/z 226.1 [M+H]$^+$.

Intermediate 14

Ethyl 3-amino-3-(pyrimidin-5-yl)propanoate (racemate)

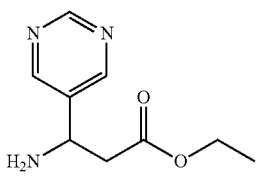

Intermediate 14

Intermediate 14 was prepared using the procedure described for Intermediate 12. ¹H NMR (500 MHz, CDCl₃) δ 9.15 (s, 1H), 8.79 (s, 2H), 4.50 (dd, J=7.8, 5.6 Hz, 1H), 4.16 (q, J=7.2 Hz, 2H), 2.77-2.64 (m, 2H), 1.25 (t, J=7.2 Hz, 3H). HPLC retention time (Method #2): 0.318 min.; LCMS (ES): m/z 196.1 [M+H]⁺.

Intermediate 15

(S)-Ethyl 3-amino-3-(quinolin-3-yl)propanoate

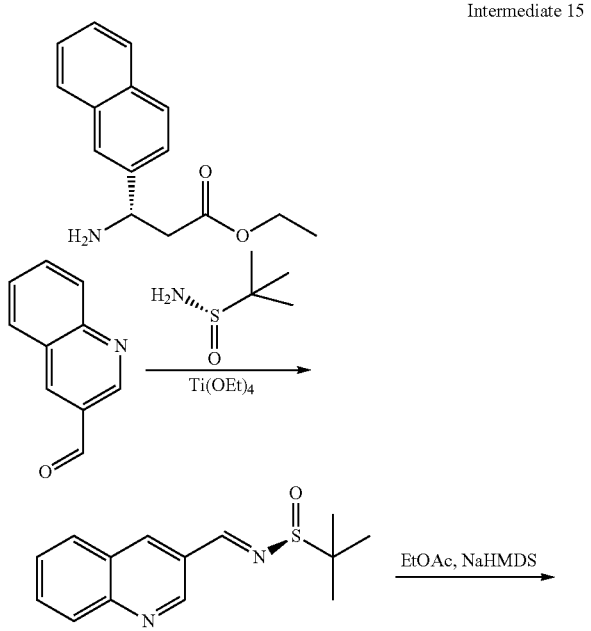

Intermediate 15

Int-15A. (S,E)-2-Methyl-N-(quinolin-3-ylmethylene)propane-2-sulfinamide: To a solution of quinoline-3-carbaldehyde (25 g, 159 mmol) in DCM (700 mL) was added (S)-2-methylpropane-2-sulfinamide (19.28 g, 159 mmol) followed by Ti(OEt)₄ (167 mL, 795 mmol). The reaction was heated to 40° C. overnight. The reaction was cooled to room temperature and quenched with water. The solids were filtered through a CELITE® bed and washed with DCM. The organic layer was washed with water, brine, dried over anhydrous sodium sulfate, and concentrated. The crude product was purified by flash chromatography to yield Int-15A (40 g, 97%) as a yellow solid. ¹H NMR (400 MHz, CDCl₃) δ 9.45 (d, J=2.0 Hz, 1H), 8.83 (s, 1H), 8.54 (d, J=1.8 Hz, 1H), 8.19 (d, J=8.5 Hz, 1H), 7.96 (d, J=8.3 Hz, 1H), 7.83-7.86 (m, 1H), 7.63-7.67 (m, 1H), 1.34 (s, 9H).

Int-15B. (S)-Ethyl 3-((S)-1,1-dimethylethylsulfinamido)-3-(quinolin-3-yl)propanoate: To a solution of 1 N NaHMDS in THF (230 mL, 230 mmol) in THF (750 mL) at −78° C. was added ethyl acetate (22.56 mL, 230 mmol) dropwise. The reaction was stirred for 0.5 h and Int-15A (40 g, 154 mmol) in THF (500 mL) was added dropwise. The reaction was stirred for 1 h at −78° C. and quenched with saturated NH₄Cl solution. The mixture was extracted with ethyl acetate. The organic layer was washed with water, brine, dried over anhydrous sodium sulfate and concentrated. The crude was purified by flash chromatography (2-3% methanol in DCM) to afford Int-15B (50 g, 93%) as a pale yellow liquid. ¹H NMR (300 MHz, DMSO-d₆) δ 8.91-9.02 (m, 1H), 8.38-8.25 (m, 1H), 7.93-8.03 (m, 2H), 7.74-7.77 (m, 1H), 7.58-7.63 (m, 1H), 4.92-4.80 (m, 1H), 4.10-3.92 (m, 2H), 3.06-2.89 (m, 2H), 1.18-1.01 (m, 12H). LCMS (ES): m/z 349.0 [M+H]⁺.

Intermediate 15: To a solution of Int-15B (50 g, 143 mmol) in ethanol (500 ml) was added 4 M HCl in 1,4-dioxane (200 mL). The reaction was stirred at rt for 2 h. The solvent was removed under reduced pressure. The residue was dissolved in water (150 mL) and washed with MTBE (3×75 mL). The aqueous layer was basified with 10% NaHCO₃ solution and extracted with ethyl acetate (3×150 mL). The combined organic layers were washed with water, brine, dried over anhydrous sodium sulfate, and concentrated. The crude was purified by SFC (Whelk (RR) (250× 30) mm, 5u; % CO₂: 70%; % Co solvent: 30%(0.2% DEA in methanol); Total Flow: 130.0 g/min; Back Pressure: 100 bars; Temperature: 30° C.; Detection: UV at 226 nm) to yield Intermediate 15 (15 g, 43%) as a brown liquid. ¹H NMR (400 MHz, DMSO-d₆) δ 8.94 (d, J=2.6 Hz, 1H), 8.27 (d, J=2.0 Hz, 1H), 7.92-8.02 (m, 2H), 7.74-7.69 (m, 1H), 7.56-7.60 (m, 1H), 4.44 (t, J=7.4 Hz, 1H), 4.05-3.97 (m, 2H), 2.76 (d, J=6.6 Hz, 2H), 2.17 (br. s., 2H), 1.09 (t, J=7.3 Hz, 3H). LCMS (ES): m/z 245.2 [M+H]⁺. 99.3% ee.

Intermediate 16

Ethyl 3-amino-3-(quinoxalin-2-yl)propanoate (racemate)

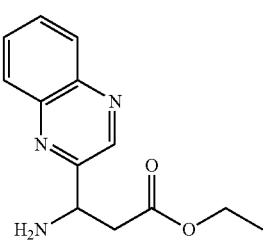

Intermediate 16

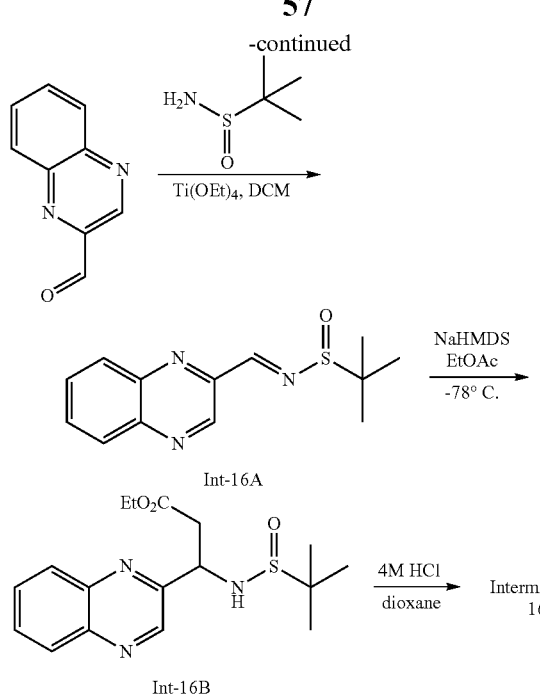

Int-16A.  (E)-2-Methyl-N-(quinoxalin-2-ylmethylene)propane-2-sulfinamide. To a solution of commercially available quinoxaline-2-carbaldehyde (0.500 g, 3.16 mmol) in DCM (14.0 mL) were added 2-methylpropane-2-sulfinamide (0.383 g, 3.16 mmol) and Ti(OEt)$_4$ (3.31 mL, 15.8 mmol). The reaction mixture was refluxed for 17 h at which point it was cooled to room temperature and quenched with water. After filtration of the reaction mixture through a CELITE® pad and subsequent washing of the cake with DCM, the organic phase of the filtrate was separated and washed with water, sat. brine, dried over anhydrous Na$_2$SO$_4$ and concentrated. The residue was purified by flash chromatography (silica gel, hexanes:EtOAc, 100:0 to 50:50) to yield Int-16A (0.690 g, 84%) as a tan solid. $^1$H NMR (500 MHz, DMSO-d$_6$) δ 9.54 (s, 1H), 8.68 (s, 1H), 8.29-8.17 (m, 2H), 8.06-7.92 (m, 2H), 1.27 (s, 9H). HPLC retention time (Method #2): 2.132 min.; LCMS (ES): m/z 262.1 [M+H]$^+$.

Int-16B.  Ethyl 3-((tert-butylsulfinyl)amino)-3-(quinoxalin-2-yl)propanoate. To a −78° C. solution of NaHMDS (1M in THF, 0.574 mL, 0.574 mmol) in THF (1.87 mL) was added ethyl acetate (0.056 mL, 0.574 mmol) dropwise and the reaction mixture was stirred at −78° C. for 30 min. A solution of Int-16A (0.100 g, 0.383 mmol) in THF (1.25 mL) was then added dropwise and the reaction mixture was allowed to stir at −78° C. for 30 min. The reaction mixture was quenched with sat. NH$_4$Cl and extracted with EtOAc (3×). The combined organic phases were washed with water, sat. brine, dried over anhydrous Na$_2$SO$_4$ and concentrated. The residue was purified by flash chromatography (silica gel, DCM:MeOH, 100:0 to 90:10) to yield Int-16B (0.111 g, 83%) as a light orange oil. $^1$H NMR (500 MHz, DMSO-d$_6$) δ 9.23 (s, 1H), 8.07-8.14 (m, 1H), 7.99-8.07 (m, 1H), 7.82-7.91 (m, 2H), 6.17 (d, J=9.35 Hz, 1H), 4.97-5.14 (m, 1H), 4.05 (quin, J=6.81 Hz, 2H), 3.10-3.26 (m, 1H), 2.94 (dd, J=8.80, 15.68 Hz, 1H), 1.10-1.19 (m, 12H). HPLC retention time (Method #2): 1.935 min.; LCMS (ES): m/z 350.1 [M+H]$^+$.

Intermediate 16: To a solution of Int-16B (0.111 g, 0.318 mmol) in EtOH (1.11 mL) at room temperature was added 4M HCl in dioxane (0.443 mL). The reaction mixture was stirred at room temperature for 1.5 h and then the solvent was removed in vacuo. The residue was dissolved in water and washed with diethyl ether (3×). The aqueous layer was basified using 10% aq. NaHCO$_3$ and then extracted with EtOAc (3×). The combined organic layers were washed with water, brine, dried over anhydrous Na$_2$SO$_4$, concentrated and dried under vacuum to yield Intermediate 16 (59.3 mg, 76%) as a tan oil which was not purified further. $^1$H NMR (400 MHz, CD$_3$OD) δ 8.99 (s, 1H), 8.16-8.00 (m, 2H), 7.90-7.74 (m, 2H), 4.66 (t, J=6.8 Hz, 1H), 4.08 (q, J=7.2 Hz, 2H), 3.14-3.03 (m, 1H), 2.98-2.87 (m, 1H), 1.15 (t, J=7.2 Hz, 3H). HPLC retention time (Method #2): 0.983 min.; LCMS (ES): m/z 246.2 [M+H]$^+$.

Intermediate 17

Ethyl (S)-3-amino-2-(((benzyloxy)carbonyl)amino)propanoate, HCl

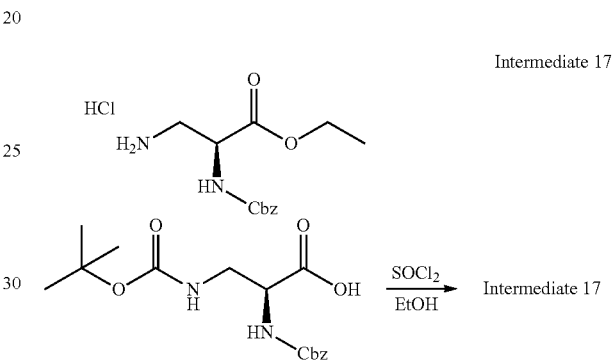

Intermediate 17. Intermediate 17 was prepared according to the procedure described in Patent: PCT INT. Appl., 2000021932. $^1$H NMR (500 MHz, DMSO-d$_6$) δ 8.16 (br. s., 3H), 7.88 (d, J=8.3 Hz, 1H), 7.43-7.26 (m, 5H), 5.08 (s, 2H), 4.38 (td, J=8.7, 4.7 Hz, 1H), 4.13 (q, J=7.2 Hz, 2H), 3.22 (dd, J=12.9, 4.4 Hz, 1H), 3.05 (dd, J=12.8, 9.5 Hz, 1H), 1.18 (t, J=7.2 Hz, 3H). HPLC retention time (Method #2): 1.078 min.; LCMS (ES): m/z 267 [M+H]$^+$.

Intermediate 18

Ethyl (S)-3-amino-2-((2,4,6-trimethylphenyl)sulfonamido)propanoate

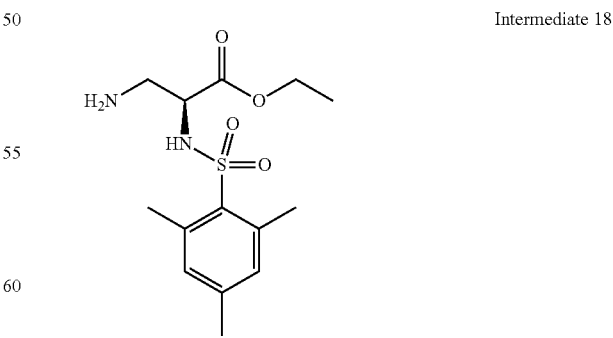

Intermediate 18 was prepared according to the procedure described in: Pitts, J. W. et. al., *J. Med. Chem.* 2000 43, 27. $^1$H NMR (500 MHz, CDCl$_3$) δ 6.95 (s, 2H), 5.63 (br. s., 1H), 5.31 (s, 1H), 3.97-4.05 (m, 2H), 3.82 (t, J=4.68 Hz, 1H), 2.94-3.05 (m, 2H), 2.66 (s, 6H), 2.29 (s, 3H), 1.14 (t, J=7.15 Hz, 3H). LCMS (ES): m/z 315 [M+H]⁺.

Intermediate 19

(E)-4-(2-(1,8-Naphthyridin-2-yl)vinyl)-1H-pyrrole-2-carboxylic acid, HCl

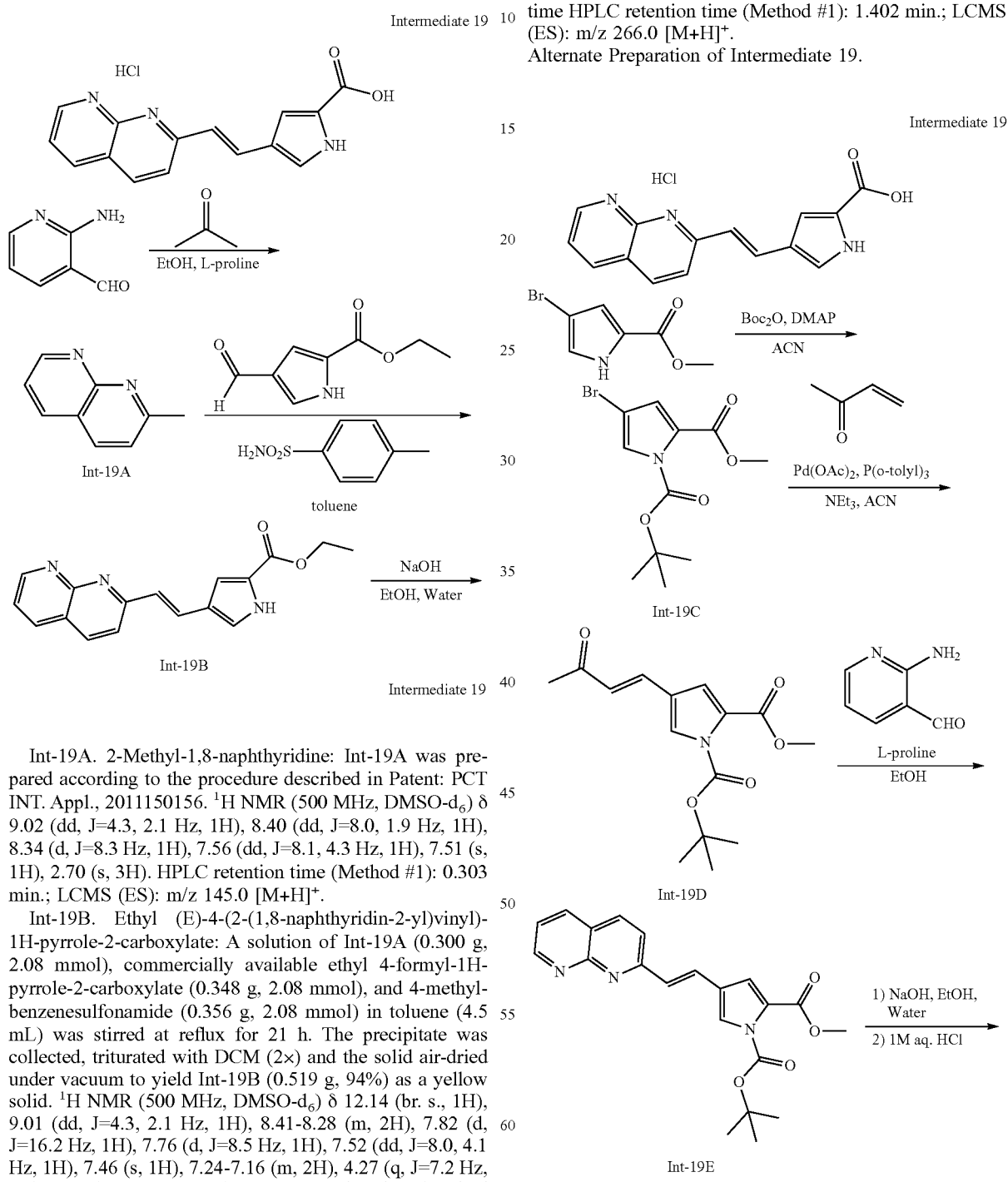

Int-19A. 2-Methyl-1,8-naphthyridine: Int-19A was prepared according to the procedure described in Patent: PCT INT. Appl., 2011150156. ¹H NMR (500 MHz, DMSO-d₆) δ 9.02 (dd, J=4.3, 2.1 Hz, 1H), 8.40 (dd, J=8.0, 1.9 Hz, 1H), 8.34 (d, J=8.3 Hz, 1H), 7.56 (dd, J=8.1, 4.3 Hz, 1H), 7.51 (s, 1H), 2.70 (s, 3H). HPLC retention time (Method #1): 0.303 min.; LCMS (ES): m/z 145.0 [M+H]⁺.

Int-19B. Ethyl (E)-4-(2-(1,8-naphthyridin-2-yl)vinyl)-1H-pyrrole-2-carboxylate: A solution of Int-19A (0.300 g, 2.08 mmol), commercially available ethyl 4-formyl-1H-pyrrole-2-carboxylate (0.348 g, 2.08 mmol), and 4-methylbenzenesulfonamide (0.356 g, 2.08 mmol) in toluene (4.5 mL) was stirred at reflux for 21 h. The precipitate was collected, triturated with DCM (2×) and the solid air-dried under vacuum to yield Int-19B (0.519 g, 94%) as a yellow solid. ¹H NMR (500 MHz, DMSO-d₆) δ 12.14 (br. s., 1H), 9.01 (dd, J=4.3, 2.1 Hz, 1H), 8.41-8.28 (m, 2H), 7.82 (d, J=16.2 Hz, 1H), 7.76 (d, J=8.5 Hz, 1H), 7.52 (dd, J=8.0, 4.1 Hz, 1H), 7.46 (s, 1H), 7.24-7.16 (m, 2H), 4.27 (q, J=7.2 Hz, 2H), 1.31 (t, J=7.0 Hz, 3H). HPLC retention time (Method #1): 1.973 min.; LCMS (ES): m/z 294.0 [M+H]⁺.

Intermediate 19: A 95:5 EtOH/H₂O solution (421 mL) containing Int-19B (35.0 g, 95.0 mmol) and NaOH (11.5 g, 286 mmol) was refluxed for 4 h whereupon the EtOH was removed in vacuo. After air drying under vacuum to remove trace EtOH, the residue was acidified to pH ~2 with 1M aq. HCl. The precipitate was collected by filtration, washed with water and dried under vacuum to yield Intermediate 19 (14.2 g, 39%) as a crude orange solid. ¹H NMR (500 MHz, DMSO-d₆) δ 12.31 (br. s., 1H), 9.16 (dd, J=4.8, 1.8 Hz, 1H), 8.80 (d, J=8.0 Hz, 1H), 8.75 (d, J=8.8 Hz, 1H), 8.22-8.08 (m, 2H), 7.85 (dd, J=8.0, 4.7 Hz, 1H), 7.53 (dd, J=2.6, 1.5 Hz, 1H), 7.33 (d, J=16.0 Hz, 1H), 7.18 (s, 1H). HPLC retention time HPLC retention time (Method #1): 1.402 min.; LCMS (ES): m/z 266.0 [M+H]⁺.

Alternate Preparation of Intermediate 19.

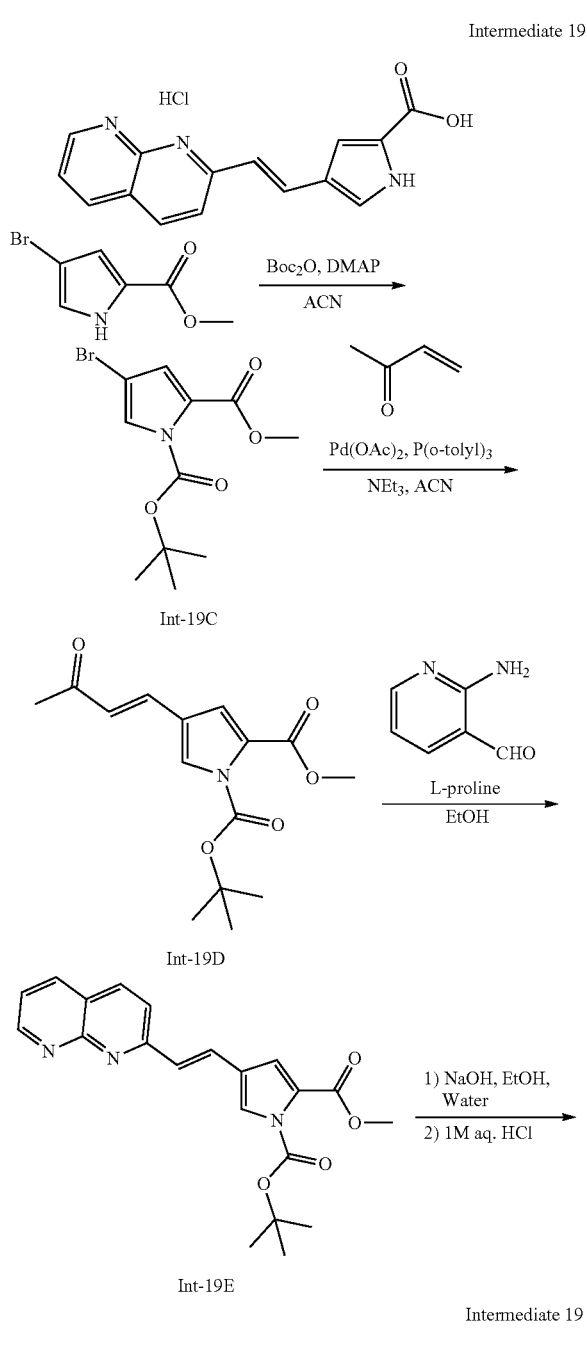

Int-19C: 1-(tert-Butyl) 2-methyl 4-bromo-1H-pyrrole-1,2-dicarboxylate: Int-19C was prepared according to the procedure described in: Desplat, V. et. al., *Journal of Enzyme Inhibition and Medicinal Chemistry* 2010 25, 204. ¹H NMR (500 MHz, CDCl₃) δ 7.31 (d, J=1.9 Hz, 1H), 6.79 (d, J=1.9 Hz, 1H), 3.85 (s, 3H), 1.58 (s, 9H). LCMS (ES): m/z 249.9 [M-tBu+H]⁺.

Int-19D. 1-(tert-Butyl) 2-methyl (E)-4-(3-oxobut-1-en-1-yl)-1H-pyrrole-1,2-dicarboxylate: A solution of Int-19C (0.100 g, 0.329 mmol), but-3-en-2-one (0.027 mL, 0.329 mmol), triethylamine (0.124 mL, 0.888 mmol), palladium acetate (8.3 mg, 0.037 mmol) and tri-o-tolylphosphine (17 mg, 0.055 mmol) in ACN (0.110 mL) was degassed with argon and then heated at 90° C. for 17 h. The solvent was removed in vacuo and the residue was purified by flash chromatography (silica gel, hexanes:EtOAc, 100:0 to 75:25) to yield Int-19D (36.7 mg, 38%) as a white solid. ¹H NMR (500 MHz, CDCl₃) δ 7.53 (d, J=1.9 Hz, 1H), 7.36 (d, J=16.0 Hz, 1H), 7.01 (d, J=1.9 Hz, 1H), 6.48 (d, J=16.2 Hz, 1H), 3.88 (s, 3H), 2.33 (s, 3H), 1.60 (s, 9H). HPLC retention time HPLC retention time (Method #1): 3.193 min.; LCMS (ES): m/z 294.1 [M+H]⁺.

Int-19E. 1-(tert-Butyl) 2-methyl (E)-4-(2-(1,8-naphthyridin-2-yl)vinyl)-1H-pyrrole-1,2-dicarboxylate, TFA: A solution of Int-19D (36 mg, 0.123 mmol), 2-aminonicotinaldehyde (19.5 mg, 0.160 mmol) and L-proline (4.58 mg, 0.115 mmol) in EtOH (0.366 mL) was stirred at 80° C. for 19 h. The solvent was removed in vacuo and the residue was purified by Prep. HPLC (Phenomenex Luna AXIA 5u C18 21.1×100 mm, 10 min gradient, 15 min run, 10% to 100% Solvent B=90% MeOH-10% H₂O-0.1% TFA, Solvent A=10% MeOH-90% H₂O-0.1% TFA) to yield Int-19E (11.3 mg, 19%) as an orange oil. LCMS (ES): m/z 280.0 [M-Boc+H]⁺.

Intermediate 19. Following the procedure described above, a solution of Int-19E (11.3 mg, 0.023 mmol) and NaOH (4.58 mg, 0.115 mmol) in EtOH (0.177 mL) and water (9.32 µL) yielded Intermediate 19 as an orange solid. LCMS (ES): m/z 266.0 [M+H]⁺.

Intermediate 20.

(E)-4-(2-(1,8-Naphthyridin-2-yl)vinyl)-1H-pyrrole-2-carboxylic acid, HCl

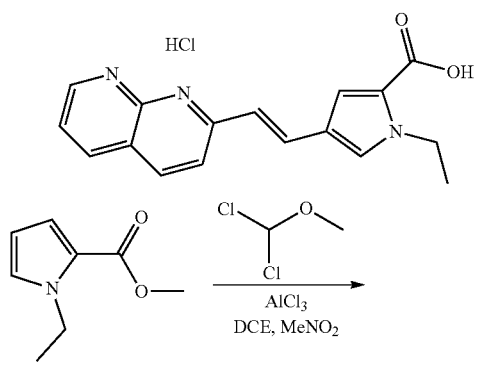

Intermediate 20

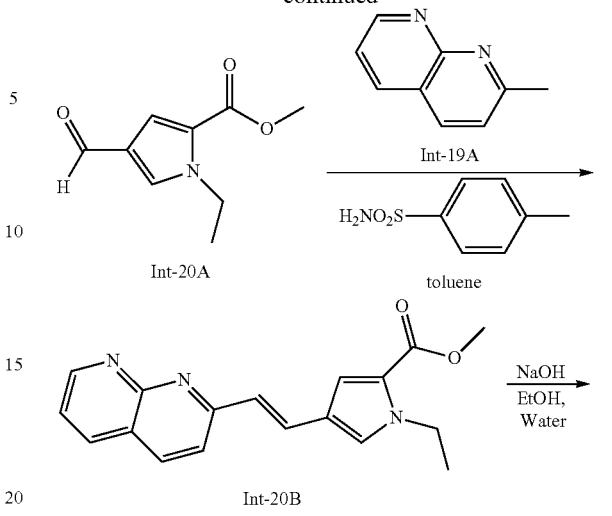

Int-20A. Methyl 1-ethyl-4-formyl-1H-pyrrole-2-carboxylate: Methyl 1-ethyl-1H-pyrrole-2-carboxylate (0.430 g, 2.81 mmol) and AlCl₃ (0.749 g, 5.61 mmol) were added to a 1:1 solution of DCE (2.90 mL) and nitromethane (2.90 mL) at −20° C. 1,1-Dichlorodimethyl ether (0.306 mL, 3.46 mmol) was added dropwise and the reaction mixture was stirred at −20° C. for 1 h. The reaction mixture was poured onto ice and the phases were separated. The aqueous layer was extracted with DCM, the organic layers were combined and washed with water, sat. NH₄Cl, brine, dried over anhydrous Na₂SO₄ and concentrated. The residue was purified by flash chromatography (silica gel, DCM:EtOAc, 100:0 to 0:100) to yield Int-20A (0.439 g, 86%) as an orange solid. ¹H NMR (500 MHz, CDCl₃) δ 9.78 (s, 1H), 7.48 (d, J=1.9 Hz, 1H), 7.37 (d, J=1.9 Hz, 1H), 4.42 (q, J=7.2 Hz, 2H), 3.86 (s, 3H), 1.46 (t, J=7.2 Hz, 3H). HPLC retention time HPLC retention time (Method #1): 2.122 min.; LCMS (ES): m/z 182.1 [M+1-1]⁺.

Int-20B. Methyl (E)-4-(2-(1,8-naphthyridin-2-yl)vinyl)-1-ethyl-1H-pyrrole-2-carboxylate: Following the procedure described in Int-19B, a solution of Int-19A (0.349 g, 2.42 mmol), Int-20A (0.438 g, 2.42 mmol), and 4-methylbenzenesulfonamide (0.413 g, 2.21 mmol) in toluene (5.23 mL) yielded Int-20B (0.488 mg, 66%) as an orange solid. ¹H NMR (500 MHz, CDCl₃) δ 9.07 (dd, J=4.4, 1.9 Hz, 1H), 8.16-8.03 (m, 2H), 7.88 (d, J=16.0 Hz, 1H), 7.54 (d, J=8.5 Hz, 1H), 7.39 (dd, J=8.0, 4.1 Hz, 1H), 7.25 (d, J=1.9 Hz, 1H), 7.15-7.03 (m, 2H), 4.38 (q, J=7.2 Hz, 2H), 3.86 (s, 3H), 1.44 (t, J=7.2 Hz, 3H). LCMS (ES): m/z 308.1 [M+H]⁺.

Intermediate 20. Following the procedure described in Intermediate 19, a solution of Int-20B and NaOH (0.316 g, 7.89 mmol) in EtOH (12.2 mL) and water (0.642 mL) yielded Intermediate 20 (0.387 g, 74%) as an orange solid. 50 mg of this material was purified by preparative HPLC (Phenomenex Luna AXIA 5u C18 21.2×100 mm, 10 min gradient, 12 min run, 5% to 100% Solvent B=90% MeOH-10% H₂O-0.1% TFA, Solvent A=10% MeOH-90% H₂O-0.1% TFA) to yield Intermediate 20 as an orange solid as the TFA salt. ¹H NMR (500 MHz, DMSO-d₆) δ 12.62 (br. s., 1H), 9.13 (dd, J=4.7, 1.7 Hz, 1H), 8.68 (d, J=6.9 Hz, 1H), 8.64 (d, J=8.8 Hz, 1H), 8.09 (d, J=8.8 Hz, 1H), 8.00 (d, J=16.0 Hz, 1H), 7.77 (dd, J=8.0, 4.7 Hz, 1H), 7.66 (d, J=1.9

Hz, 1H), 7.25 (d, J=1.9 Hz, 1H), 7.21 (d, J=16.0 Hz, 1H), 4.36 (q, J=7.2 Hz, 2H), 1.34 (t, J=7.0 Hz, 3H). LCMS (ES): m/z 294.0 [M+H]⁺.

Intermediate 21.

(E)-4-(2-(1,8-Naphthyridin-2-yl)vinyl)-1-methyl-1H-pyrrole-2-carboxylic Acid, HCl

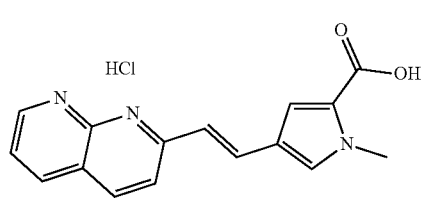

Intermediate 21

Intermediate 21 was prepared according to the procedure described in Intermediate 19 starting from commercially available methyl 4-formyl-1-methyl-1H-pyrrole-2-carboxylate. LCMS (ES): m/z 280.1 [M+H]⁺.

Intermediate 22.

(E)-4-(2-(1,8-Naphthyridin-2-yl)vinyl)-5-methyl-1H-pyrrole-2-carboxylic Acid, HCl

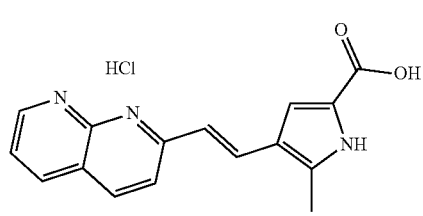

Intermediate 22

Intermediate 22 was prepared according to the procedure described in Intermediate 19 starting from Ethyl 4-formyl-5-methyl-1H-pyrrole-2-carboxylate which was prepared according to the procedure described in Patent: PCT Int. Appl., 2005026149. LCMS (ES): m/z 280.1 [M+H]⁺.

Intermediate 23.

4-(1,8-Naphthyridin-2-yl)-1H-pyrrole-2-carboxylic Acid, HCl

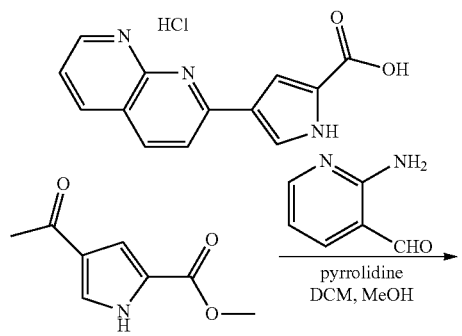

Intermediate 23

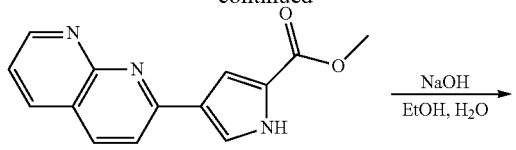

Intermediate 23

Int-23A. Methyl 4-(1,8-naphthyridin-2-yl)-1H-pyrrole-2-carboxylate: To a solution of methyl 4-acetyl-1H-pyrrole-2-carboxylate (0.342 g, 2.05 mmol) and pyrrolidine (0.372 mL, 4.50 mmL) in DCM (1.71 mL) and MeOH (5.12 mL) at room temperature was added 2-aminonicotinaldehyde (0.250 g, 2.05 mmol). The reaction mixture was stirred at room temperature for 24 h. The precipitate was collected, washed with MeOH and dried under vacuum to yield Int-23A (0.345 g, 67%) as a light yellow solid. ¹H NMR (500 MHz, DMSO-d₆) δ 12.37 (br. s., 1H), 9.00 (dd, J=4.3, 2.1 Hz, 1H), 8.44-8.30 (m, 2H), 8.05 (d, J=8.5 Hz, 1H), 7.93 (d, J=1.7 Hz, 1H), 7.57 (d, J=1.7 Hz, 1H), 7.52 (dd, J=8.0, 4.1 Hz, 1H), 3.83 (s, 3H). HPLC retention time (Method #1): 1.515 min.; LCMS (ES): m/z 254.1 [M+H]⁺.

Intermediate 23. Following the procedure described in Intermediate 19, Int-23A (0.100 g, 0.395 mmol) and NaOH (0.047 g, 1.19 mmol) in EtOH (3.75 mL) and water (0.197 mL) yielded Intermediate 23 (0.109 g, 100%) as an orange solid. ¹H NMR (500 MHz, DMSO-d₆) δ 12.62 (br. s., 1H), 9.17 (dd, J=5.0, 1.7 Hz, 1H), 8.91-8.81 (m, 1H), 8.72 (d, J=8.8 Hz, 1H), 8.37 (d, J=8.5 Hz, 1H), 8.23-8.13 (m, 1H), 7.88 (dd, J=8.1, 5.1 Hz, 1H), 7.66 (t, J=1.9 Hz, 1H). HPLC retention time (Method #1): 1.205 min.; LCMS (ES): m/z 240.1 [M+H]⁺.

Intermediate 24.

4-(3-(1,8-Naphthyridin-2-yl)propyl)-1H-pyrrole-2-carboxylic Acid, HCl, 3 NaCl

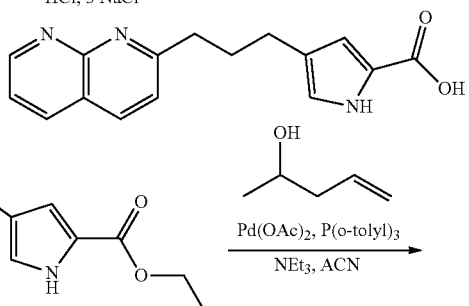

Intermediate 24

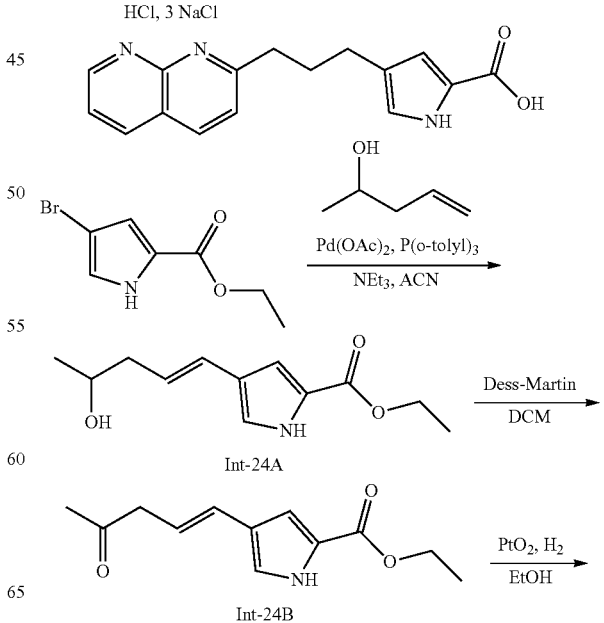

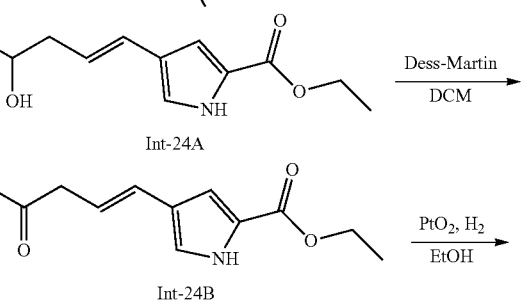

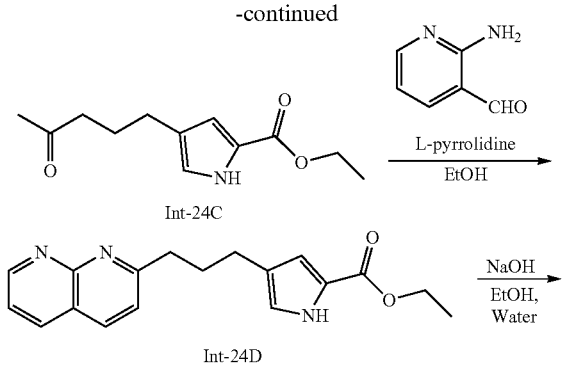

Intermediate 24

Int-24A. Ethyl (E)-4-(4-hydroxypent-1-en-1-yl)-1H-pyrrole-2-carboxylate: Following the procedure described in Int-1A, a solution of ethyl 4-bromo-1H-pyrrole-2-carboxylate (0.500 g, 2.29 mmol), pent-4-en-2-ol (0.829 mL, 8.03 mmol), triethylamine (0.863 mL, 6.19 mmol), palladium acetate (58.0 mg, 0.258 mmol) and tri-o-tolylphosphine (0.116 g, 0.381 mmol) in ACN (22.7 mL) yielded Int-24A (0.201 g, 39%) as a yellow oil. $^1$H NMR (500 MHz, CDCl$_3$) δ 8.99 (br. s., 1H), 6.99 (s, 1H), 6.91-6.87 (m, 1H), 6.34 (d, J=16.0 Hz, 1H), 6.01-5.90 (m, 1H), 4.36-4.28 (m, 2H), 3.89 (dd, J=12.2, 6.2 Hz, 1H), 2.40-2.32 (m, 1H), 2.30-2.19 (m, 1H), 1.41-1.32 (m, 3H), 1.25 (d, J=6.3 Hz, 3H). HPLC retention time (Method #2): 1.568 min.; LCMS (ES): m/z 224.2 [M+H]$^+$.

Int-24B. Ethyl (E)-4-(4-oxopent-1-en-1-yl)-1H-pyrrole-2-carboxylate: Dess-Martin periodinane (0.456 g, 1.08 mmol) was added to a solution of Int-24A (0.200 g, 0.896 mmol) in DCM (8.37 mL). The reaction mixture was stirred at room temperature for 1 h then diluted with diethyl ether. After filtration of the mixture through a CELITE® pad and subsequent washing of the cake with diethyl ether, the filtrate was concentrated in vacuo and the residue was purified by flash chromatography (silica gel, hexanes:EtOAc, 100:0 to 70:30) to yield Int-24B (106 mg, 53%) as a yellow oil. $^1$H NMR (500 MHz, CDCl$_3$) δ 8.93 (br. s., 1H), 6.90-6.88 (m, 1H), 6.81 (dd, J=2.8, 1.7 Hz, 1H), 6.23 (d, J=16.0 Hz, 1H), 5.92 (dt, J=15.7, 7.2 Hz, 1H), 4.22 (q, J=7.2 Hz, 2H), 3.16 (d, J=7.2 Hz, 2H), 2.09 (s, 3H), 1.26 (t, J=7.2 Hz, 3H). HPLC retention time (Method #2): 0.703 min.; 1.733 min LCMS (ES): m/z 222.2 [M+H]$^+$.

Int-24C. Ethyl 4-(4-oxopentyl)-1H-pyrrole-2-carboxylate: To a solution of Int-24B (95 mg, 0.185 mmol) in EtOH (6.33 mL) was added PtO$_2$ (22 mg, 0.095 mmol). The suspension was hydrogenated (1 atm H$_2$, balloon) at room temperature for 2 h. After filtration of the reaction mixture through a CELITE® pad and subsequent washing of the cake with EtOH, the filtrate was concentrated in vacuo and dried under vacuum to yield Int-24C (82 mg, 77%) as a yellow oil. $^1$H NMR (500 MHz, CDCl$_3$) δ 8.91 (br. s., 1H), 6.79-6.68 (m, 2H), 4.31 (q, J=7.1 Hz, 2H), 2.47 (dt, J=17.5, 7.5 Hz, 4H), 2.13 (s, 3H), 1.86 (quin, J=7.4 Hz, 2H), 1.36 (t, J=7.2 Hz, 3H). HPLC retention time (Method #2): 1.788 min.; LCMS (ES): m/z 224.2 [M+H]$^+$.

Int-24D. Ethyl 4-(3-(1,8-naphthyridin-2-yl)propyl)-1H-pyrrole-2-carboxylate: To a solution of Int-24C (82 mg, 0.367 mmol) and pyrrolidine (36 μL, 0.441 mmol) in DCM (0.307 mL) and EtOH (0.921 mL) was added 2-aminonicotinaldehyde (45 mg, 0.367 mmol) and the mixture was stirred at room temperature for 7 h. The solvent was removed in vacuo and the residue was purified by flash chromatography (silica gel, DCM:EtOAc, 100:0 to 25:75) to yield Int-24D (61.2 mg, 54%) as a white solid. $^1$H NMR (500 MHz, CDCl$_3$) δ 9.10 (dd, J=4.1, 1.9 Hz, 1H), 8.88 (br. s., 1H), 8.16 (dd, J=8.0, 1.9 Hz, 1H), 8.10 (d, J=8.3 Hz, 1H), 7.45 (dd, J=8.1, 4.3 Hz, 1H), 7.38 (d, J=8.3 Hz, 1H), 6.79 (s, 2H), 4.30 (q, J=7.2 Hz, 2H), 3.18-3.00 (m, 2H), 2.61 (t, J=7.6 Hz, 2H), 2.20 (quin, J=7.6 Hz, 2H), 1.35 (t, J=7.2 Hz, 3H). HPLC retention time (Method #2): 1.140 min.; LCMS (ES): m/z 310.3 [M+H]$^+$.

Intermediate 24: A 95:5 EtOH/H$_2$O solution (1.58 mL) containing Int-24D (61.2 mg, 0.198 mmol) and NaOH (23.7 mg, 0.593 mmol) was refluxed for 2 h whereupon the EtOH was removed in vacuo. After air drying under vacuum to remove trace EtOH, the residue was acidified to pH ~2 with 1M aq. HCl. The water was removed in vacuo and the residue was air-dried under vacuum to yield Intermediate 24 (98 mg, 100%) as a crude orange solid. $^1$H NMR (500 MHz, DMSO-d$_6$) δ 11.43 (br. s., 1H), 9.25 (br. s., 1H), 8.88 (d, J=7.2 Hz, 1H), 8.82 (d, J=8.0 Hz, 1H), 7.93 (d, J=5.8 Hz, 2H), 6.79 (br. s., 1H), 6.59 (br. s., 1H), 3.14 (br. s., 2H), 2.56-2.51 (m, 2H), 2.09 (br. s., 2H). HPLC retention time (Method #2): 0.703 min.; LCMS (ES): m/z 282.2 [M+H]$^+$.

Intermediate 25-1

4-(2-(5,6,7,8-Tetrahydro-1,8-naphthyridin-2-yl)ethyl)-1H-pyrrole-2-carboxylic Acid, HCl, 4 NaCl

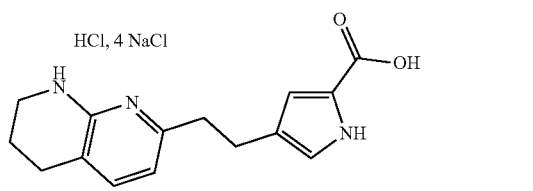

Intermediate 25-1 and
Intermediate 25-2

4-(2-(1,2,3,4-Tetrahydro-1,8-naphthyridin-2-yl)ethyl)-1H-pyrrole-2-carboxylic Acid, HCl, 4 NaCl

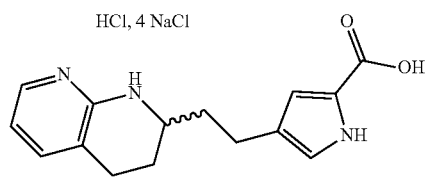

Intermediate 25-2

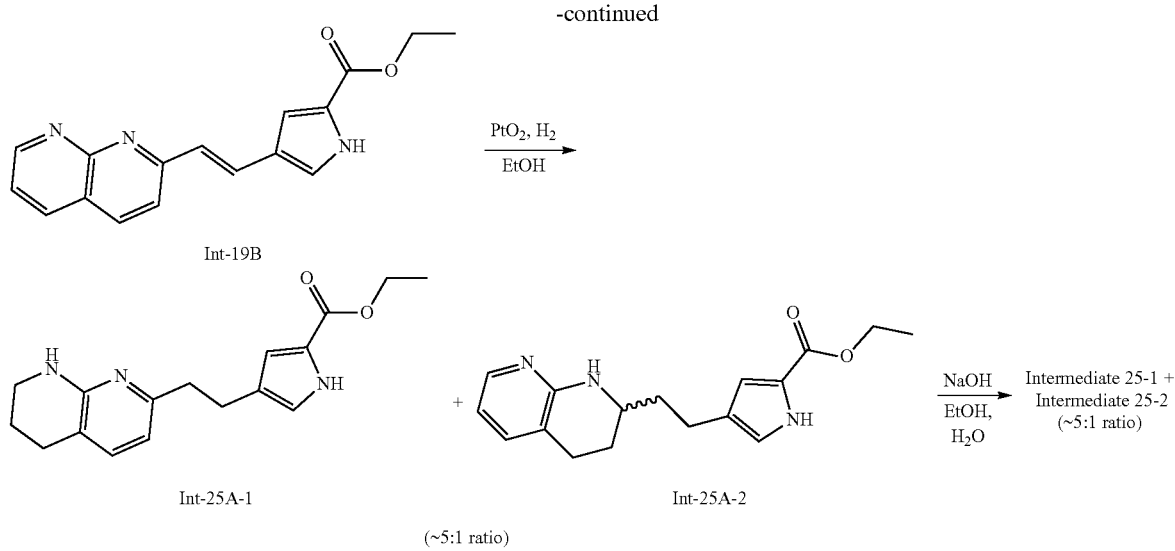

Int-25A-1. Ethyl 4-(2-(5,6,7,8-tetrahydro-1,8-naphthyridin-2-yl)ethyl)-1H-pyrrole-2-carboxylate, TFA and Int-25A-2. Ethyl 4-(2-(1,2,3,4-tetrahydro-1,8-naphthyridin-2-yl)ethyl)-1H-pyrrole-2-carboxylate, TFA: To a solution of Int-19B (0.500 g, 1.69 mmol) in EtOH (22.6 mL) was added $PtO_2$ (77.0 mg, 0.339 mmol). The suspension was hydrogenated (1 atm Hz, balloon) at room temperature for 24 h. The white precipitate that formed was dissolved in MeOH, filtered through a CELITE® pad and the cake was washed with MeOH. The filtrate was concentrated in vacuo and air-dried under vacuum. The residue was purified by reverse phase ISCO chromatography (50 g column—HPC 18 Aq silica gel cartridge, 24 min. run) and eluted with a gradient from 10% ACN/$H_2O$/TFA (5%/95%/0.05%) to 100% ACN/$H_2O$/TFA (95%/5%/0.05%) to yield a mixture of Int-25A-1 and Int-25A-2 (0.544 mg, 77%) in approximately a 5:1 ratio as a white solid. HPLC retention time (Method #2): 1.363 min.; LCMS (ES): m/z 300.2 $[M+H]^+$.

Intermediate 25-1 and Intermediate 25-2. Using the procedure described to prepare Intermediate 24, a mixture of Int-25A-1 and Int-25A-2 (0.544 g, 1.32 mmol) and NaOH (0.211 g, 0.526 mmol) in EtOH (6.26 mL) and water (0.329 mL) yielded a mixture of Intermediate 25-1 and Intermediate 25-2 (0.713 g, 100%) in approximately a 5:1 ratio as a crude light orange solid. HPLC retention time (Method #2): 0.938 min.; LCMS (ES): m/z 272.2 $[M+H]^+$.

Example 1

(S)-3-(3-Fluoro-4-methoxyphenyl)-3-(4-(2-(5,6,7,8-tetrahydro-1,8-naphthyridin-2-yl)ethyl)-1H-pyrrole-2-carboxamido)propanoic Acid

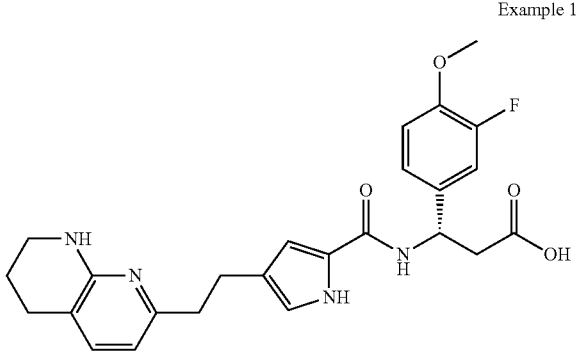 [SMILES: COc1ccc([C@H](CC(=O)O)NC(=O)c2cc(CCc3ccc4c(n3)NCCC4)c[nH]2)cc1F]

Example 1 and

Example 2

(3S)-3-(3-Fluoro-4-methoxyphenyl)-3-(4-(2-(1,2,3,4-tetrahydro-1,8-naphthyridin-2-yl)ethyl)-1H-pyrrole-2-carboxamido)propanoic Acid

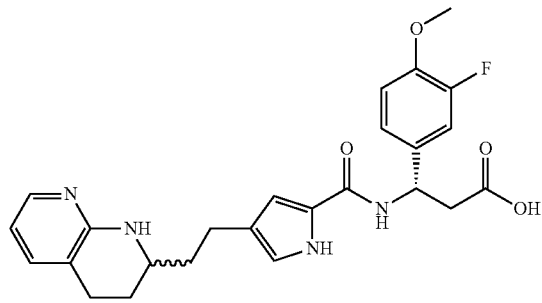

Example 2

-continued
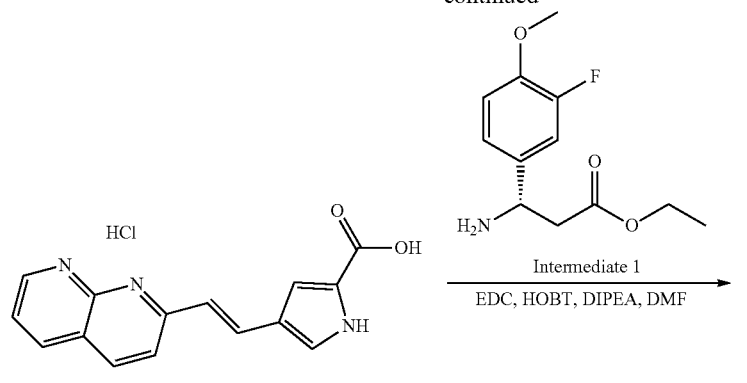
Intermediate 19
Intermediate 1
EDC, HOBT, DIPEA, DMF
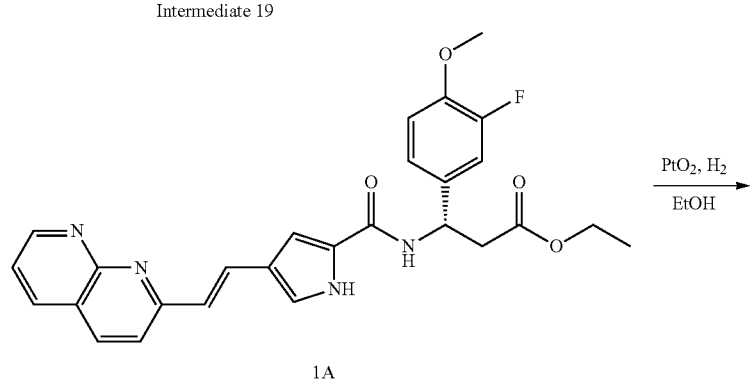
1A
PtO₂, H₂
EtOH
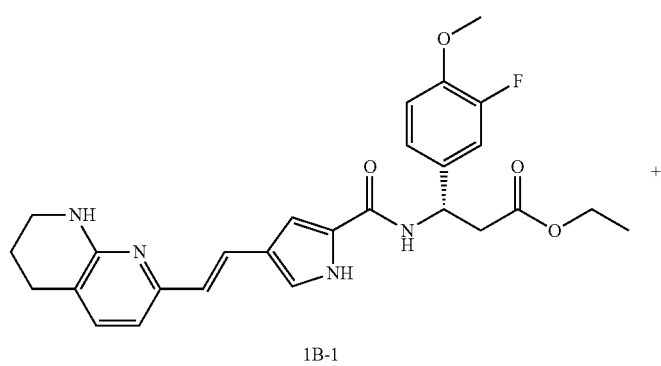
1B-1
+
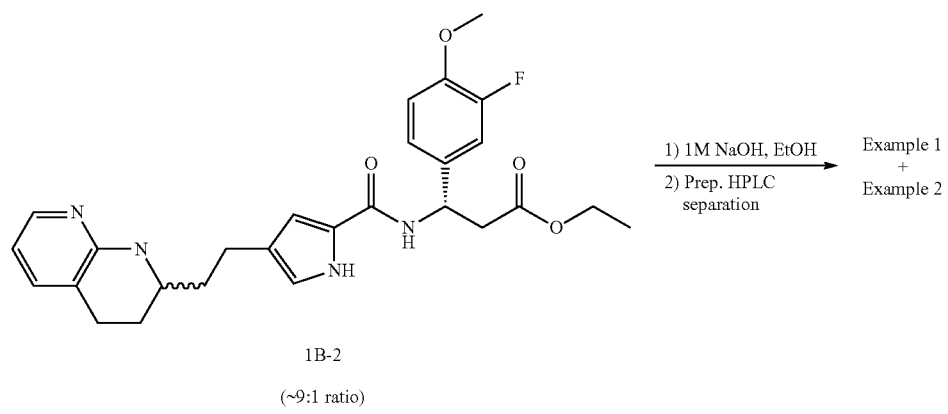 [SMILES: CCOC(=O)C[C@H](NC(=O)c1cc(CCC2CCc3cccnc3N2)c[nH]1)c1ccc(OC)c(F)c1]
1B-2
(~9:1 ratio)
1) 1M NaOH, EtOH
2) Prep. HPLC separation
Example 1
+
Example 2

1A. Ethyl (S,E)-3-(4-(2-(1,8-naphthyridin-2-yl)vinyl)-1H-pyrrole-2-carboxamido)-3-(3-fluoro-4-methoxyphenyl)propanoate: To a solution of Intermediate 19 (13.9 g, 37.0 mmol) and Intermediate 1 (10.3 g, 37.0 mmol) in DMF (185 mL) were added EDC (14.2 g, 73.9 mmol), HOBT (11.3 g, 73.9 mmol) and DIPEA (20.5 mL, 118 mmol). The reaction mixture was stirred at room temperature for 2 h whereupon it was diluted with water (200 mL). The precipitate was collected, washed with water and dried under vacuum to yield 1A (20.0 g, 100%). $^{1}$H NMR (500 MHz, DMSO-$d_6$) δ 11.76 (br. s., 1H), 9.00 (dd, J=4.1, 1.9 Hz, 1H), 8.52 (d, J=8.5 Hz, 1H), 8.40-8.32 (m, 2H), 7.87-7.76 (m, 2H), 7.51 (dd, J=8.1, 4.3 Hz, 1H), 7.36-7.22 (m, 3H), 7.20-7.10 (m, 2H), 7.04 (d, J=16.2 Hz, 1H), 5.46-5.33 (m, 1H), 4.08-3.97 (m, 2H), 3.83-3.78 (m, 3H), 2.99-2.79 (m, 2H), 1.12 (t, J=7.2 Hz, 3H). HPLC retention time (Method #1): 2.440 min.; LCMS (ES): m/z 489.0 [M+H]$^+$.

1B-1. Ethyl (S)-3-(3-fluoro-4-methoxyphenyl)-3-(4-(2-(5,6,7,8-tetrahydro-1,8-naphthyridin-2-yl)ethyl)-1H-pyrrole-2-carboxamido)propanoate and 1B-2. Ethyl (3S)-3-(3-fluoro-4-methoxyphenyl)-3-(4-(2-(1,2,3,4,4a,8a-hexahydro-1,8-naphthyridin-2-yl)ethyl)-1H-pyrrole-2-carboxamido)propanoate: To a solution of 1A (0.100 g, 0.205 mmol) in EtOH (5.53 mL) was added and PtO$_2$ (9.3 mg, 0.041 mmol). The suspension was hydrogenated (1 atm H$_2$, balloon) at room temperature for 18 h. After filtration of the reaction mixture through a CELITE® pad and subsequent washing of the cake with EtOH, the filtrate was concentrated in vacuo and dried under vacuum to yield a mixture of 1B-1 and 1B-2 (100 mg, 99%) as a crude yellow gummy foam in approximately a 9:1 ratio. HPLC retention time (Method #1): 2.253 min.; LCMS (ES): m/z 495.0 [M+H]$^+$.

Example 1

To a solution of a mixture of 1B-1 and 1B-2 (34.2 mg, 0.069 mmol) in EtOH (1.3 mL) at room temperature was added 1M aq. NaOH (0.207 mL, 0.207 mmol) and the reaction mixture was stirred for 1 h at which point the EtOH was removed in vacuo. After air drying under vacuum to remove trace EtOH, the residue was acidified to pH ~2 with 1M aq. HCl. The water was removed in vacuo and the residue was purified by preparative HPLC (Column: XBridge C18, 19×200 mm, 5-μm particles; Mobile Phase A: 5:95 acetonitrile: water with 10 mM ammonium acetate; Mobile Phase B: 95:5 acetonitrile: water with 10 mM ammonium acetate; Gradient: 13-43% B over 25 minutes, then a 4-minute hold at 43% B; Flow: 20 mL/min.) to yield Example 1 (12 mg, 36%). $^{1}$H NMR (500 MHz, CDCl$_3$) δ 10.83 (br. s., 1H), 9.14 (br. s., 1H), 8.84 (br. s., 1H), 7.26-7.21 (m, 1H), 7.19-7.12 (m, 2H), 6.89 (t, J=8.7 Hz, 1H), 6.43 (br. s., 2H), 6.18 (d, J=6.9 Hz, 1H), 5.37 (d, J=6.1 Hz, 1H), 3.85 (s, 3H), 3.43 (br. s., 2H), 2.95-2.73 (m, 6H), 2.68 (t, J=5.9 Hz, 2H), 1.89 (d, J=5.5 Hz, 2H). HPLC retention time (Method #1): 1.837 min.; LCMS (ES): m/z 467.1 [M+H]$^+$. Human αVβ6 IC50 (nM)=2.55.

Example 2

The preparative HPLC purification described in Example 1 afforded Example 2 (2.7 mg, 8%) as a mixture of diastereomers. $^{1}$H NMR (500 MHz, CDCl$_3$) δ 10.17-9.93 (m, 1H), 9.48 (br. s., 1H), 8.81-8.54 (m, 1H), 7.59-7.41 (m, 1H), 7.33 (d, J=5.5 Hz, 1H), 7.21-7.06 (m, 2H), 6.93-6.79 (m, 1H), 6.70-6.40 (m, 3H), 5.37 (br. s., 1H), 3.82 (d, J=5.0 Hz, 3H), 3.52 (br. s., 1H), 2.92-2.57 (m, 6H), 2.00-1.83 (m, 2H), 1.75 (dd, J=13.6, 7.3 Hz, 1H), 1.60 (dd, J=13.6, 9.2 Hz, 1H). HPLC retention time (Method #1): 1.892 min.; LCMS (ES): m/z 467.1 [M+H]$^+$. Human αVβ6 IC50 (nM)=3.75.

The Examples in the following Table 1 were prepared in similar manner to Example 1-1. $^{1}$H NMR was measured at 500 MHz, DMSO-$d_6$, unless otherwise indicated.

TABLE 1

| Example No. | Structure and Name | Analytical and Biological Data |
|---|---|---|
| 3 | 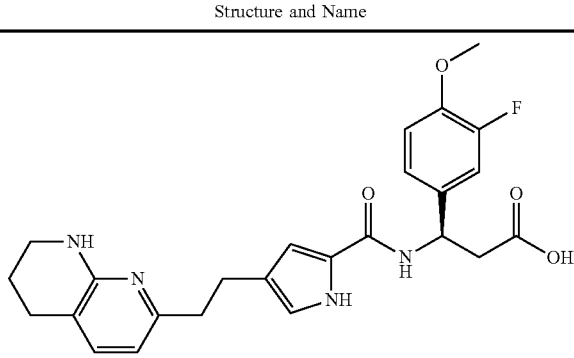<br>(R)-3-(3-Fluoro-4-methoxyphenyl)-3(4-(2-(5,6,7,8-tetrahydro-1,8-naphthyridin-2-yl)ethyl)-1H-pyrrole-2-carboxamido)-propanoic acid | $^{1}$H NMR (500 MHz, DMSO-$d_6$) δ 11.04 (br. s., 1H), 8.29 (d, J = 8.5 Hz, 1H), 7.20 (d, J = 12.5 Hz, 1H), 7.15-7.04 (m, 2H), 7.01 (d, J = 7.3 Hz, 1H), 6.76-6.47 (m, 2H), 6.36-6.07 (m, 1H), 5.29 (q, J = 7.6 Hz, 1H), 3.79 (s, 3H), 3.23 (br. s., 2H), 2.81-2.63 (m, 6H), 2.59 (t, J = 6.1 Hz, 2H), 1.78-1.64 (m, 2H). LCMS (ES): m/z 467.3 [M + H]$^+$. Human αVβ6 IC50 (nM) = 228.97. |

TABLE 1-continued

| Example No. | Structure and Name | Analytical and Biological Data |
|---|---|---|
| 4 | 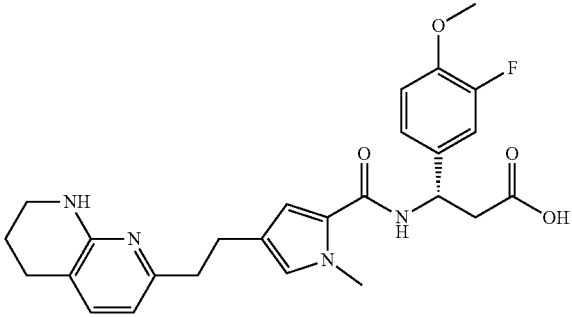<br>(S)-3-(3-Fluoro-4-methoxyphenyl)-3-(1-methyl-4-(2-(5,6,7,8-tetrahydro-1,8-naphthyridin-2-yl)ethyl-1H-pyrrole-2-carboxamido)propanoic acid | $^1$H NMR (500 MHz, DMSO-d$_6$) δ 8.17 (d, J = 8.2 Hz, 1H), 7.17 (d, J = 12.5 Hz, 1H), 7.11-7.02 (m, 2H), 6.98 (d, J = 7.3 Hz, 1H), 6.66 (d, J = 18.0 Hz, 2H), 6.24 (d, J = 7.3 Hz, 1H), 5.23 (q, J = 7.9 Hz, 1H), 3.76 (s, 3H), 3.67 (s, 3H), 3.20 (br. s., 2H), 2.83-2.71 (m, 1H), 2.69-2.54 (m, 7H), 1.75-1.63 (m, 2H). LCMS (ES): m/z 481.3 [M + H]$^+$. Human αVβ6 IC50 (nM) = 22.09. |
| 5 | 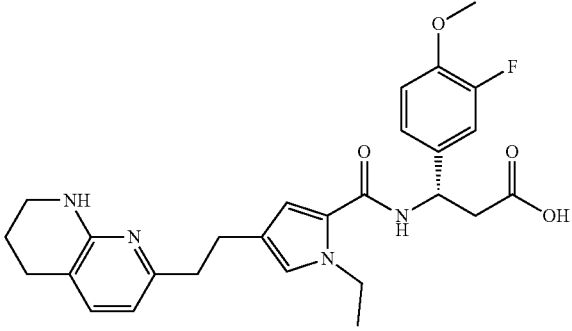<br>Ethyl (S)-3-(1-ethyl-4-(2-(5,6,7,8-tetrahydro-1,8-naphthyridin-2-yl)ethyl)-1H-pyrrole-2-carboxamido)-3-(3-fluoro-4-methoxyphenyl)propanoate | $^1$H NMR (500 MHz, DMSO-d$_6$) δ 8.18 (d, J = 8.2 Hz, 1H), 7.16 (d, J = 12.8 Hz, 1H), 7.10-7.02 (m, 2H), 6.99 (d, J = 7.3 Hz, 1H), 6.70 (s, 1H), 6.65 (s, 1H), 6.35-6.08 (m, 1H), 5.31-5.13 (m, 1H), 4.12 (dquin, J = 13.2, 6.6 Hz, 2H), 3.76 (s, 3H), 3.20 (br. s., 2H), 2.74 (d, J = 8.5 Hz, 1H), 2.68-2.63 (m, 1H), 2.61 (s, 4H), 2.56 (t, J = 6.0 Hz, 2H), 1.75-1.60 (m, 2H), 1.13 (t, J = 6.9 Hz, 3H). LCMS (ES): m/z 495.5 [M + H]$^+$. Human αVβ6 IC50 (nM) = 50.27. |
| 6 | 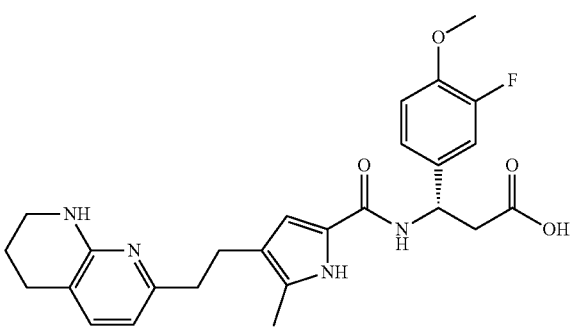<br>(S)-3-(3-Fluoro-4-methoxyphenyl)-3-(5-methyl-4-(2-(5,6,7,8-tetrahydro-1,8-naphthyridin-2-yl)ethyl)-1H-pyrrole-2-carboxamido)propanoic acid | $^1$H NMR (500 MHz, DMSO-d$_6$) δ 10.91 (br. s., 1H), 8.41 (br. s., 1H), 7.17 (d, J = 12.7 Hz, 1H), 7.11-6.84 (m, 3H), 6.60 (s, 1H), 6.24 (d, J = 7.2 Hz, 1H), 5.31-5.07 (m, 1H), 3.78 (s, 3H), 3.23 (br. s., 2H), 2.69-2.56 (m, 8H), 2.03 (s, 3H), 1.74 (d, J = 5.7 Hz, 2H). LCMS (ES): m/z 481.3 [M + H]$^+$. Human αVβ6 IC50 (nM) = 5.93. |

TABLE 1-continued

| Example No. | Structure and Name | Analytical and Biological Data |
|---|---|---|
| 7 | 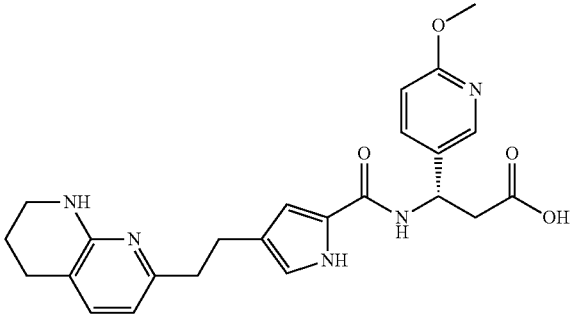<br>(S)-3-(6-Methoxypyridin-3-yl)-3-(4-(2-(5,6,7,8-tetrahydro-1,8-naphthyridin-2-yl)ethyl)-1H-pyrrole-2-carboxamido)-propanoic acid | $^1$H NMR (500 MHz, DMSO-$d_6$) δ 11.07 (br. s., 1H), 8.25 (d, J = 8.5 Hz, 1H), 8.08 (s, 1H), 7.67 (d, J = 8.2 Hz, 1H), 7.30 (d, J = 6.4 Hz, 1H), 6.74 (d, J = 8.5 Hz, 1H), 6.61 (br. s., 2H), 6.41 (d, J = 7.0 Hz, 1H), 5.28 (q, J = 7.6 Hz, 1H), 3.77 (s, 3H), 3.29 (br. s., 2H), 2.86-2.58 (m, 8H), 1.74 (br. s., 2H). LCMS (ES): m/z 450.1 [M + H]$^+$. Human αVβ6 IC50 (nM) = 4.00. |
| 8 | 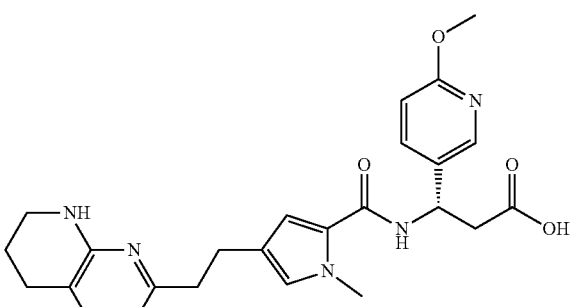<br>(S)-3-(6-Methoxypyridin-3-yl)-3-(1-methyl-4-(2-(5,6,7,8-tetrahydro-1,8-naphthyridin-2-yl)ethyl)-1H-pyrrole-2-carboxamido)-propanoic acid | $^1$H NMR (500 MHz, DMSO-$d_6$) δ 8.26 (d, J = 8.5 Hz, 1H), 8.11 (s, 1H), 7.71 (d, J = 8.5 Hz, 1H), 7.03 (d, J = 7.3 Hz, 1H), 6.77 (d, J = 8.5 Hz, 1H), 6.68 (d, J = 7.0 Hz, 2H), 6.28 (d, J = 7.0 Hz, 1H), 5.28 (q, J = 7.7 Hz, 1H), 3.81 (s, 3H), 3.70 (s, 3H), 3.24 (br. s., 2H), 2.90-2.81 (m, 1H), 2.77-2.70 (m, 1H), 2.66-2.56 (m, 6H), 1.80-1.64 (m, 2H). LCMS (ES): m/z 464.2 [M + H]$^+$. Human αVβ6 IC50 (nM) = 22.53. |
| 9 | 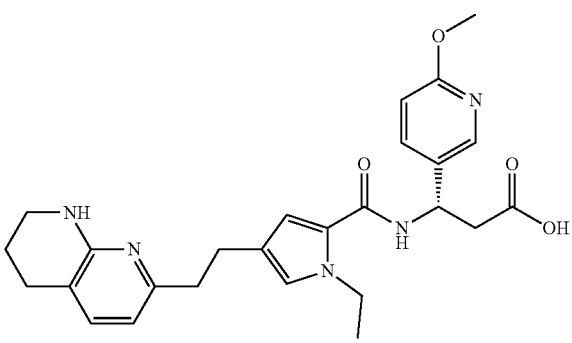<br>Ethyl (S)-3-(1-ethyl-4-(2-(5,6,7,8-tetrahydro-1,8-naphthyridin-2-yl)ethyl)-1H-pyrrole-2-carboxamido)-3-(6-methoxypyridin-3-yl)propanoate | $^1$H NMR (500 MHz, DMSO-$d_6$) δ 8.26 (d, J = 8.2 Hz, 1H), 8.13 (s, 1H), 7.72 (d, J = 8.2 Hz, 1H), 7.03 (d, J = 7.0 Hz, 1H), 6.78 (d, J = 8.5 Hz, 1H), 6.74 (s, 1H), 6.68 (s, 1H), 6.28 (d, J = 7.3 Hz, 1H), 5.29 (q, J = 7.7 Hz, 1H), 4.28-4.06 (m, 2H), 3.81 (s, 3H), 3.24 (br. s., 2H), 2.90-2.81 (m, 1H), 2.80-2.69 (m, 1H), 2.64 (s, 4H), 2.60 (t, J = 6.0 Hz, 2H), 1.80-1.62 (m, 2H), 1.17 (t, J = 7.0 Hz, 3H). LCMS (ES): m/z 478.1 [M + H]$^+$. Human αVβ6 IC50 (nM) = 46.81. |

TABLE 1-continued

| Example No. | Structure and Name | Analytical and Biological Data |
|---|---|---|
| 10 | 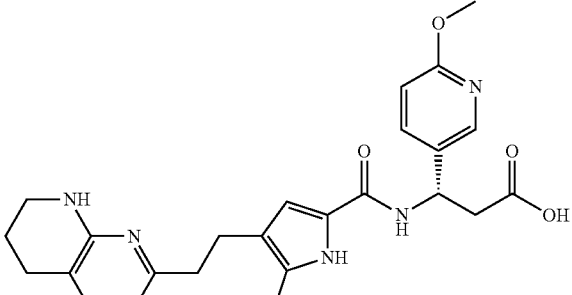<br>(S)-3-(6-ethoxypyridin-3-yl)-3-(5-methyl-4-(2-(5,6,7,8-tetrahydro-1,8-naphthyridin-2-yl)ethyl)-1H-pyrrole-2-carboxamido)-propanoic acid | $^1$H NMR (500 MHz, DMSO-$d_6$) δ 10.82 (br. s., 1H), 8.24 (d, J = 7.9 Hz, 1H), 8.09 (s, 1H), 7.68 (d, J = 6.5 Hz, 1H), 7.02 (d, J = 7.2 Hz, 1H), 6.76 (d, J = 8.7 Hz, 1H), 6.60 (br. s., 1H), 6.24 (d, J = 7.3 Hz, 1H), 5.26 (d, J = 7.5 Hz, 1H), 3.73 (br. s., 3H), 3.22 (br. s., 2H), 2.84-2.67 (m, 2H), 2.57 (d, J = 7.2 Hz, 6H), 2.01 (s, 3H), 1.72 (br. s., 2H). LCMS (ES): m/z 464.4 [M + H]$^+$. Human αVβ6 IC50 (nM) = 3.96; Human αVβ3 IC50 (nM) = 2.49; Human αVβ5 IC50 (nM) = 10.45; and Human αVβ8 IC50 (nM) = 414.86. |
| 11 | 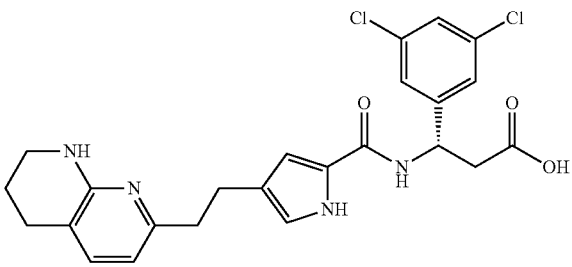<br>(S)-3-(3,5-Dichlorophenyl)-3-(4-(2-(5,6,7,8-tetrahydro-1,8-naphthyridin-2-yl)ethyl)-1H-pyrrole-2-carboxamido)-propanoic acid | $^1$H NMR (500 MHz, DMSO-$d_6$) δ 11.13 (br. s., 1H), 8.32 (d, J = 7.9 Hz, 1H), 7.48 (s, 1H), 7.42 (d, J = 1.5 Hz, 2H), 7.12 (d, J = 7.0 Hz, 1H), 6.70 (br. s., 1H), 6.65 (br. s., 1H), 6.34 (d, J = 7.3 Hz, 1H), 5.39-5.25 (m, 1H), 3.27 (br. s., 2H), 2.87-2.74 (m, 2H), 2.71 (s, 4H), 2.62 (t, J = 6.0 Hz, 2H), 1.79-1.65 (m, 2H). LCMS (ES): m/z 487.2 [M + H]$^+$. Human αVβ6 IC50 (nM) = 2.03. |
| 12 | 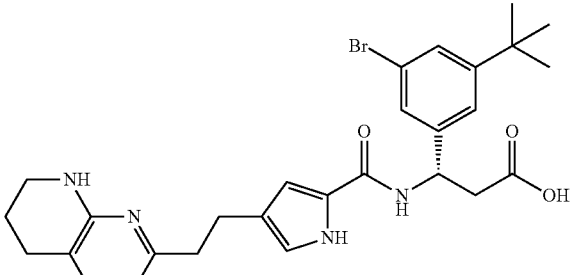<br>(S)-3-(3-Bromo-5-(tert-butyl)phenyl)-3-(4-(2-(5,6,7,8-tetrahydro-1,8-naphthyridin-2-yl)ethyl)-1H-pyrrole-2-carboxamido)-propanoic acid | $^1$H NMR (500 MHz, DMSO-$d_6$) δ 11.08 (br. s., 1H), 8.37 (d, J = 7.6 Hz, 1H), 7.44-7.31 (m, 3H), 7.01 (d, J = 7.3 Hz, 1H), 6.69 (br. s., 1H), 6.63 (br. s., 1H), 6.30-6.20 (m, 1H), 5.33 (d, J = 7.3 Hz, 1H), 3.23 (br. s., 2H), 2.84-2.63 (m, 6H), 2.59 (br. s., 2H), 1.75 (d, J = 5.5 Hz, 2H), 1.25 (s, 9H). LCMS (ES): m/z 553.2 [M + H]$^+$. Human αVβ6 IC50 (nM) = 0.63. |
| 13 | 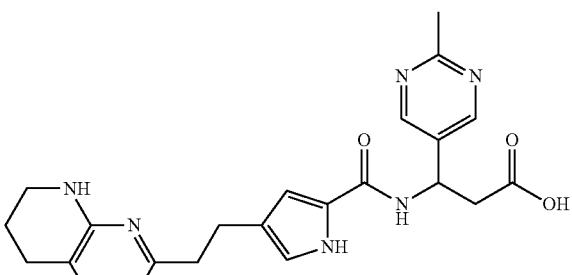<br>3-(2-Methylpyrimidin-5-yl)-3-(4-(2-(5,6,7,8-tetrahydro-1,8-naphthyridin-2-yl)ethyl)-1H-pyrrole-2-carboxamido)-propanoic acid | $^1$H NMR (500 MHz, CD$_3$OD) δ 8.73 (s, 2H), 7.35 (d, J = 7.4 Hz, 1H), 6.73 (d, J = 1.4 Hz, 1H), 6.69 (d, J = 1.4 Hz, 1H), 6.45 (d, J = 7.4 Hz, 1H), 5.52-5.39 (m, 1H), 3.48-3.38 (m, 2H), 2.94-2.78 (m, 6H), 2.75 (t, J = 6.2 Hz, 2H), 2.66 (s, 3H), 1.93-1.84 (m, 2H). LCMS (ES): m/z 435.3 [M + H]$^+$. Human αVβ6 IC50 (nM) = 6.70; Human αVβ1 IC50 (nM) = 3,999.74; Human αVβ3 IC50 (nM) = 4.59; Human αVβ5 IC50 (nM) = 3.84; and Human αVβ8 IC50 (nM) = 5,000.00. |

TABLE 1-continued

| Example No. | Structure and Name | Analytical and Biological Data |
|---|---|---|
| 14 | 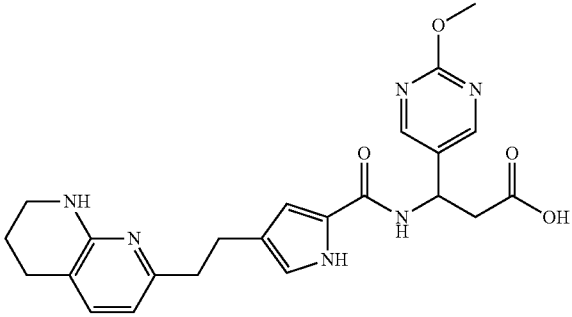<br>3-(2-Methoxypyrimidin-5-yl)-3-(4-(2-(5,6,7,8-tetrahydro-1,8-naphthyridin-2-yl)ethyl)-1H-pyrrole-2-carboxamido-propanoic acid | $^1$H NMR (500 MHz, CD$_3$OD) δ 8.58 (s, 2H), 7.39 (d, J = 6.8 Hz, 1H), 6.68 (d, J = 13.4 Hz, 2H), 6.47 (d, J = 7.1 Hz, 1H), 5.42 (br. s., 1H), 3.97 (s, 3H), 3.42 (br. s., 2H), 2.92-2.69 (m, 8H), 1.88 (br. s., 2H). LCMS (ES): m/z 451.1 [M + H]$^+$. Human αVβ6 IC50 (nM) = 7.17; Human αVβ1 IC50 (nM) = 3,711.68; Human αVβ3 IC50 (nM) = 4.69; Human αVβ5 IC50 (nM) = 5.68; and Human αVβ8 IC50 (nM) = 5.043.53. |
| 15 | 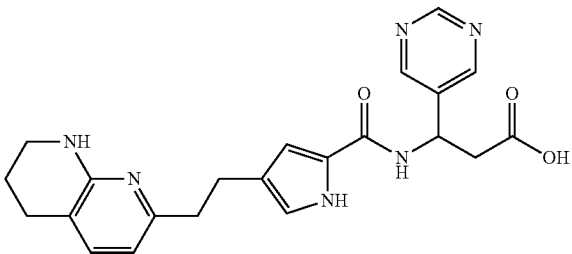<br>3-(Pyrimidin-5-yl)-3-(4-(2-(5,6,7,8-tetrahydro-1,8-naphthyridin-2-yl)ethyl)-1H-pyrrole-2-carboxamido)propanoic acid | $^1$H NMR (500 MHz, DMSO-d$_6$) δ 11.15 (br. s., 1H), 9.06 (s, 1H), 8.80 (s, 2H), 8.49 (d, J = 7.2 Hz, 1H), 7.01 (d, J = 7.2 Hz, 1H), 6.69 (s, 1H), 6.63 (s, 1H), 6.26 (d, J = 7.2 Hz, 1H), 5.40-5.22 (m, 1H), 3.23 (br. s., 2H), 2.99-2.79 (m, 2H), 2.67 (br. s., 4H), 2.60 (t, J = 6.1 Hz, 2H), 1.78-1.68 (m, 2H). LCMS (ES): m/z 421.1 [M + H]$^+$. Human αVβ6 IC50 (nM) = 11.88. |
| 16 | 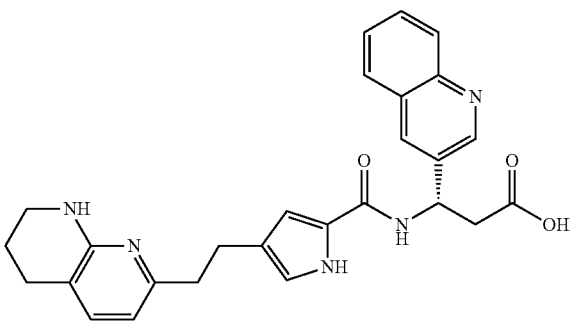<br>(S)-3-(Quinolin-3-yl)-3-(4-(2-(5,6,7,8-tetrahydro-1,8-naphthyridin-2-yl)ethyl)-1H-pyrrole-2-carboxamido)-propanoic acid | $^1$H NMR (500 MHz, CD$_3$OD) δ 8.95 (d, J = 1.3 Hz, 1H), 8.32 (s, 1H), 7.97 (d, J = 8.4 Hz, 1H), 7.86 (d, J = 8.1 Hz, 1H), 7.71 (t, J = 7.6 Hz, 1H), 7.60-7.52 (m, 1H), 7.33 (d, J = 7.3 Hz, 1H), 6.75 (s, 1H), 6.67 (s, 1H), 6.44 (d, J = 7.3 Hz, 1H), 5.66 (t, J = 6.5 Hz, 1H), 3.38 (t, J = 5.5 Hz, 2H), 2.93 (d, J = 6.6 Hz, 2H), 2.81 (dd, J = 17.0, 6.3 Hz, 4H), 2.71 (t, J = 6.1 Hz, 2H), 1.86 (quin, J = 5.8 Hz, 2H). LCMS (ES): m/z 470.1 [M + H]$^+$. Human αVβ6 IC50 (nM) = 1.10; Human αVβ1 IC50 (nM) = 359.96; Human αVβ3 IC50 (nM) = 3.44; Human αVβ5 IC50 (nM) = 1.73; and Human αVβ8 IC50 (nM) = 2.665.62. |
| 17 | 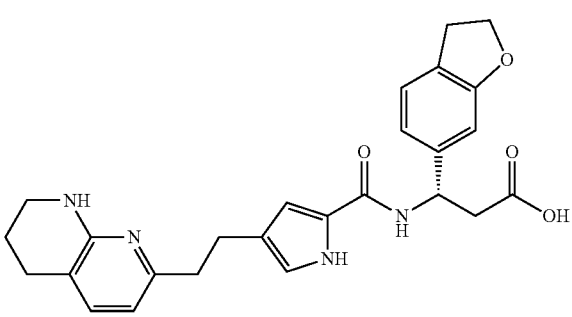<br>(S)-3-(2,3-Dihydrobenzofuran-6-yl)-3-(4-(2-(5,6,7,8-tetrahydro-1,8-naphthyridin-2-yl)ethyl)-1H-pyrrole-2-carboxamido)propanoic acid | $^1$H NMR (500 MHz, CD$_3$OD) δ 7.36 (d, J = 7.3 Hz, 1H), 7.11 (d, J = 7.7 Hz, 1H), 6.86 (d, J = 7.7 Hz, 1H), 6.77 (s, 1H), 6.66 (d, J = 11.6 Hz, 2H), 6.47 (d, J = 7.3 Hz, 1H), 5.34 (t, J = 6.6 Hz, 1H), 4.49 (t, J = 8.6 Hz, 2H), 3.44-3.41 (m, 2H), 3.13 (t, J = 8.6 Hz, 2H), 2.90-2.79 (m, 4H), 2.77-2.69 (m, 4H), 1.92-1.87 (m, 2H). LCMS (ES): m/z 461.4 [M + H]$^+$. Human αVβ6 IC50 (nM) = 4.63; Human αVβ1 IC50 (nM) = 1,217.83; Human αVβ3 IC50 (nM) = 3.68; Human αVβ5 IC50 (nM) = 0.85; and Human αVβ8 IC50 (nM) = 3,760.94. |

| Example No. | Structure and Name | Analytical and Biological Data |
|---|---|---|
| 18 | 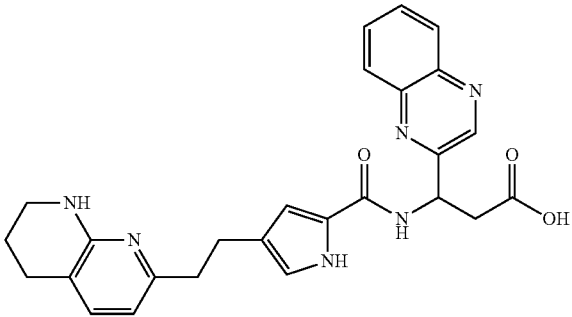<br>3-(Quinoxalin-2-yl)-3-(4-(2-(5,6,7,8-tetrahydro-1,8-naphthyridin-2-yl)ethyl)-1H-pyrrole-2-carboxamido)propanoic acid | $^1$H NMR (500 MHz, DMSO-$d_6$) δ 11.12 (br. s., 1H), 8.96 (br. s., 1H), 8.71 (br. s., 1H), 8.05 (dd, J = 16.4, 7.4 Hz, 2H), 7.83 (t, J = 6.7 Hz, 2H), 7.02 (d, J = 7.2 Hz, 1H), 6.73 (br. s., 1H), 6.65 (br. s., 1H), 6.27 (d, J = 7.2 Hz, 1H), 5.58 (br, s., 1H), 3.59 (br. s., 2H), 3.23 (br. s., 2H), 2.66 (br. s., 4H), 2.58 (d, J = 6.1 Hz, 2H), 1.73 (br. s., 2H). LCMS (ES): m/z 470.0 [M + H]$^+$. Human αVβ6 IC50 (nM) = 25.91. |
| 19 | 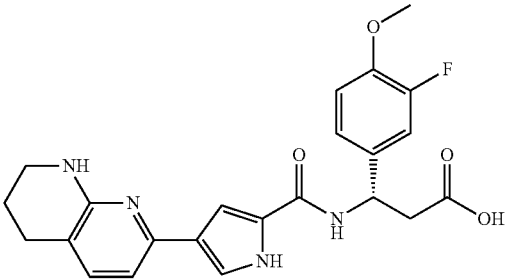<br>(S)-3-(3-Fluoro-4-methoxyphenyl)-3-(4-(5,6,7,8-tetrahydro-1,8-naphthyridin-2-yl)-1H-pyrrole-2-carboxamido)-propanoic acid | $^1$H NMR (500 MHz, DMSO-$d_6$) δ 11.45 (br. s., 1H), 8.47 (d, J = 8.2 Hz, 1H), 7.34-7.20 (m, 3H), 7.15-6.93 (m, 3H), 6.68 (d, J = 7.3 Hz, 1H), 6.06 (br. s., 1H), 5.45-5.21 (m, 1H), 3.80 (s, 3H), 3.27 (br. s., 2H), 2.86-2.78 (m, 1H), 2.76-2.68 (m, 1H), 2.63 (t, J = 6.1 Hz, 2H), 1.85-1.67 (m, 2H). LCMS (ES): m/z 439.2 [M + H]$^+$. Human αVβ6 IC50 (nM) = 81.03. |
| 20 | 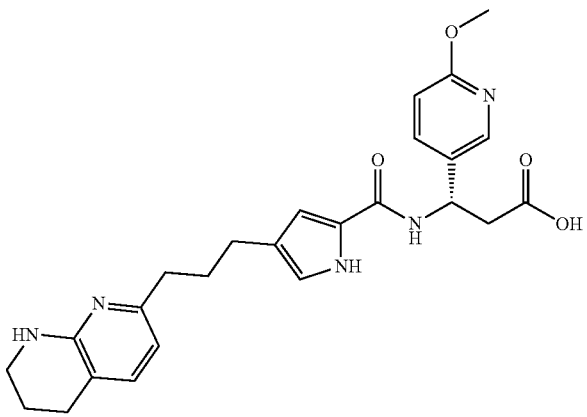<br>(S)-3-(6-Methoxypyridin-3-yl)-3-(4-(3-(5,6,7,8-tetrahydro-1,8-naphthyridin-2-yl)propyl)-1H-pyrrole-2-carboxamido)-propanoic acid, 2TFA | $^1$H NMR (500 MHz, DMSO-$d_6$) δ 11.08 (br. s., 1H), 8.29 (d, J = 8.2 Hz, 1H), 8.12 (s, 1H), 7.71 (d, J = 8.6 Hz, 1H), 7.16 (br. s., 1H), 6.78 (d, J = 8.6 Hz, 1H), 6.65 (br. s., 2H), 6.34 (d, J = 7.0 Hz, 1H), 5.32 (q, J = 7.7 Hz, 1H), 3.80 (s, 3H), 3.26 (br. s., 2H), 2.94-2.69 (m, 2H), 2.62 (t, J = 5.8 Hz, 2H), 2.49-2.46 (m, 2H), 2.38 (t, J = 7.3 Hz, 2H), 1.83-1.63 (m, 4H). LCMS (ES): m/z 464.3 [M + H]$^+$. Human αVβ6 IC50 (nM) = 22.41. |

| Example No. | Structure and Name | Analytical and Biological Data |
|---|---|---|
| 21 | 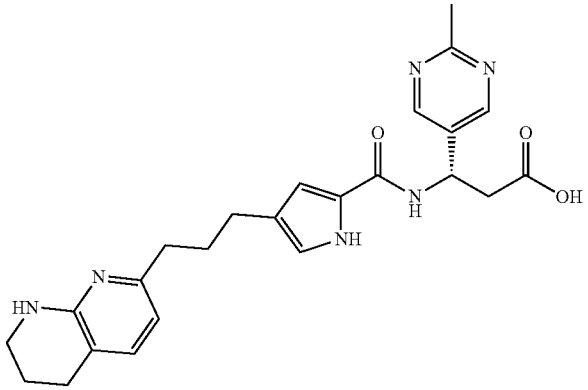<br>(S)-3-(2-Methylpyrimidin-5-yl)-3-(4-(3-(5,6,7,8-tetrahydro-1,8-naphthyridin-2-yl)propyl)-1H-pyrrole-2-carboxamido)-propanoic acid, TFA | $^1$H NMR (400 MHz, CD$_3$OD) δ 8.73 (d, J = 1.5 Hz, 2H), 7.53 (br d, J = 7.5 Hz, 1H), 6.76-6.65 (m, 2H), 6.59 (dd, J = 7.4, 3.6 Hz, 1H), 5.48-5.42 (m, 1H), 3.53-3.42 (m, 2H), 3.06-2.91 (m, 2H), 2.79-2.75 (m, 2H), 2.70 (br d, J = 7.9 Hz, 2H), 2.67 (s, 3H), 2.56 (t, J = 7.4 Hz, 2H), 2.03-1.87 (m, 4H). LCMS (ES): m/z 449.4 [M + H]$^+$. Human αVβ6 IC50 (nM) = 166.60. |
| 22 | 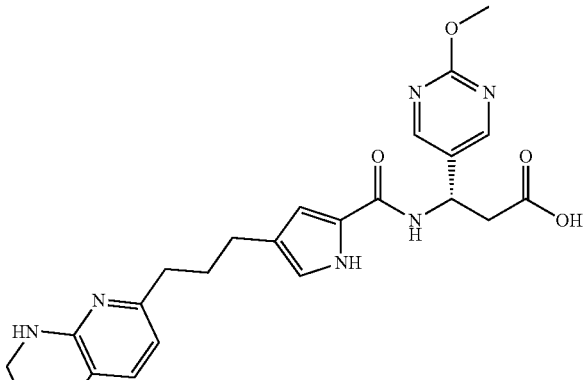<br>(S)-3-(2-Methoxypyrimidin-5-yl)-3-(4-(3-(5,6,7,8-tetrahydro-1,8-napthyridin-2-yl)propyl)-1H-pyrrole-2-carboxamido)-propanoic acid | $^1$H NMR (500 MHz, CD$_3$OD) δ 8.60 (s, 2H), 7.38 (br d, J = 7.2 Hz, 1H), 6.70 (s, 1H), 6.66 (s, 1H), 6.49 (d, J = 7.3 Hz, 1H), 5.36 (br t, J = 6.7 Hz, 1H), 3.97 (s, 3H), 3.45-3.38 (m, 2H), 2.80 (br d, J = 6.8 Hz, 2H), 2.73 (br t, J = 6.0 Hz, 2H), 2.65-2.61 (m, 2H), 2.52 (br t, J = 6.9 Hz, 2H), 1.97-1.93 (m, 2H), 1.93-1.85 (m, 2H). LCMS (ES): m/z 465.5 [M + H]$^+$. Human αVβ6 IC50 (nM) = 14.48. |

Example 23

(S)-3-(4-(2-(5,6,7,8-Tetrahydro-1,8-naphthyridin-2-yl)ethyl)-1H-pyrrole-2-carboxamido)-2-((2,4,6-trimethylphenyl)sulfonamido)propanoic Acid and Example 24

(2S)-3-(4-(2-(1,2,3,4-Tetrahydro-1,8-naphthyridin-2-yl)ethyl)-1H-pyrrole-2-carboxamido)-2-((2,4,6-trimethylphenyl)sulfonamido)propanoic Acid Example 23

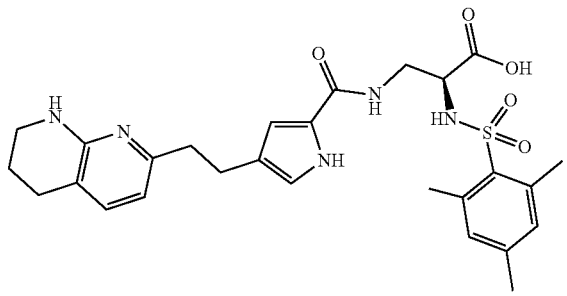

Example 24

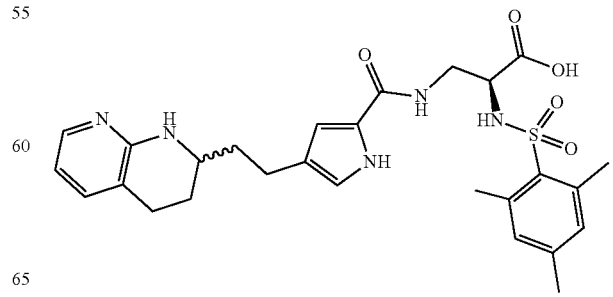

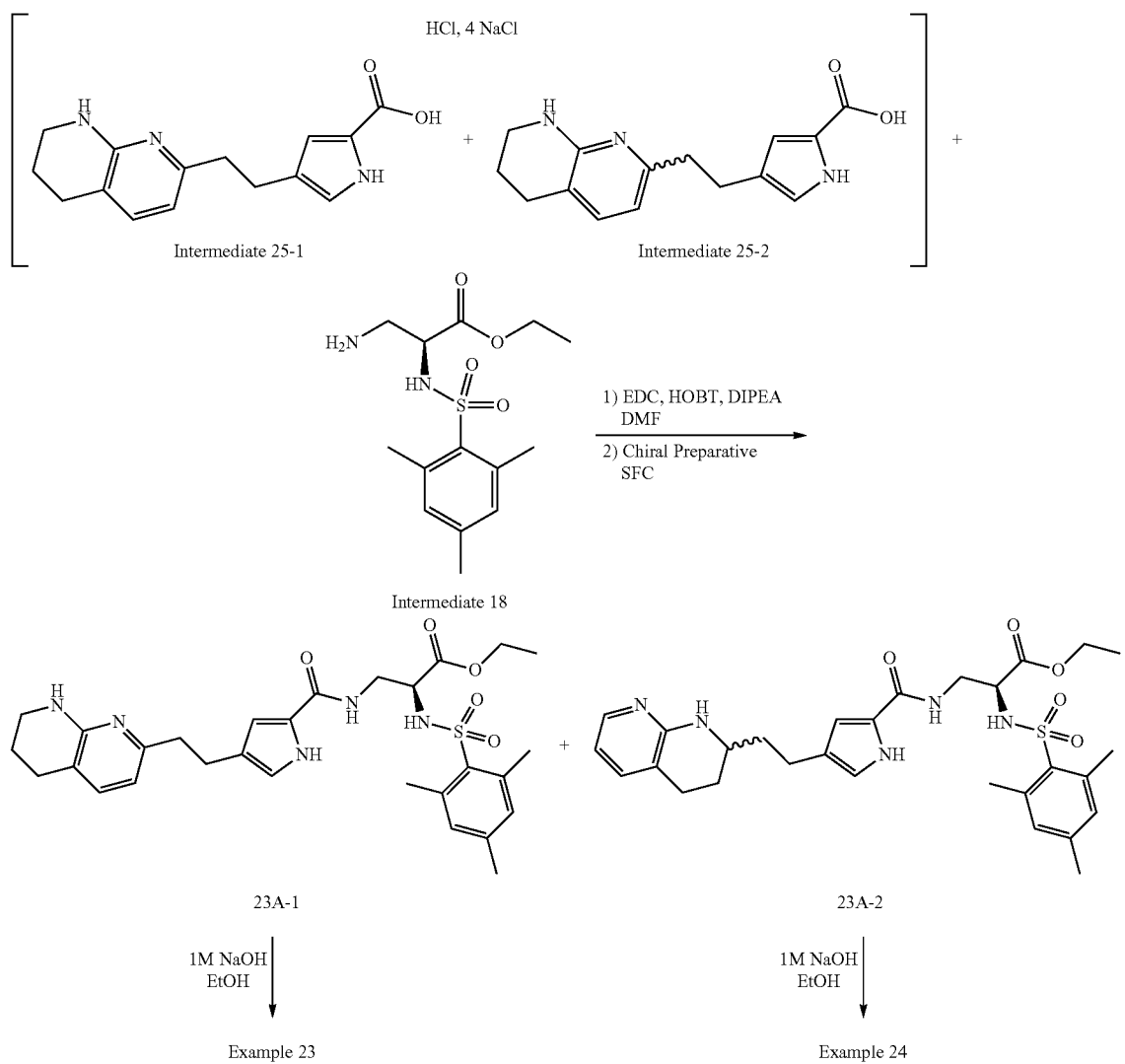

23-1A. Ethyl (S)-3-(4-(2-(5,6,7,8-tetrahydro-1,8-naphthyridin-2-yl)ethyl)-1H-pyrrole-2-carboxamido)-2-((2,4,6-trimethylphenyl)sulfonamido)propanoate: To a solution of a mixture of Intermediate 25-1 and Intermediate 25-2 (0.713 g, 1.32 mmol) and Intermediate 18 (0.414 g, 1.32 mmol) in DMF (6.58 mL) were added EDC (0.505 g, 2.63 mmol), HOBT (0.403 g, 2.63 mmol) and DIPEA (0.506 mL, 2.90 mmol). The reaction mixture was stirred at room temperature for 16 h whereupon it was diluted with water. The precipitate was collected, washed with water and dried under vacuum to afford a crude brown solid which was purified by chiral preparative SFC (Instrument: Berger Multigram II Prep SFC; Column: Ethyl 2-Pyridine 21×250 mm, 5 micron; Mobile Phase: 15% 10 mM NH$_4$OAc in MeOH+3% H$_2$O/85% CO$_2$; Flow Conditions: 45 mL/min, 100 Bar, 40° C.; Detector Wavelength: 220 nm; Injection Details: 0.5 mL of ~50 mg/mL in MeOH) to yield 23A-1 (0.135 g, 16%) as a yellow solid. $^1$H NMR (500 MHz, CD$_3$OD) δ 7.54 (d, J=7.2 Hz, 1H), 6.92 (s, 2H), 6.72 (s, 1H), 6.58 (d, J=7.2 Hz, 1H), 6.53 (d, J=1.1 Hz, 1H), 4.03 (dd, J=8.1, 5.9 Hz, 1H), 3.91-3.80 (m, 2H), 3.64 (dd, J=13.8, 5.8 Hz, 1H), 3.51-3.40 (m, 3H), 2.93 (d, J=6.9 Hz, 2H), 2.89-2.83 (m, 2H), 2.80 (t, J=6.3 Hz, 2H), 2.59 (s, 6H), 2.25 (s, 3H), 1.93 (quin, J=5.9 Hz, 2H), 1.04 (t, J=7.0 Hz, 3H). HPLC retention time (Method #2): 1.952 min.; LCMS (ES): m/z 568.5 [M+H]$^+$.

23A-2. Ethyl (2S)-3-(4-(2-(1,2,3,4-tetrahydro-1,8-naphthyridin-2-yl)ethyl)-1H-pyrrole-2-carboxamido)-2-((2,4,6-trimethylphenyl)sulfonamido)propanoate: The chiral preparative SFC purification detailed for 23A-1 also yielded 23A-2 (36.6 mg, 5%) as a yellow solid. $^1$H NMR (500 MHz, CD$_3$OD) δ 7.72-7.62 (m, 2H), 6.92 (s, 2H), 6.82-6.73 (m, 2H), 6.60 (s, 1H), 4.04 (dd, J=7.8, 5.9 Hz, 1H), 3.87 (q, J=7.2 Hz, 2H), 3.70-3.57 (m, 2H), 3.46 (dd, J=13.6, 8.1 Hz, 1H), 2.89 (br. s., 1H), 2.84 (dd, J=9.5, 5.1 Hz, 1H), 2.65 (t, J=7.7 Hz, 2H), 2.59 (s, 6H), 2.25 (s, 3H), 2.09 (dd, J=13.5, 5.2 Hz, 1H), 1.96-1.91 (m, 1H), 1.89-1.82 (m, 1H), 1.76-1.68 (m, 1H), 1.04 (t, J=7.2 Hz, 3H). HPLC retention time (Method #2): 1.972 min.; LCMS (ES): m/z 568.5 [M+H]$^+$.

Example 23

To a solution of 23A-1 (50.0 mg, 0.078 mmol) in EtOH (1.41 mL) at room temperature was added 1M aq. NaOH (0.271 mL, 0.271 mmol) and the reaction mixture was stirred for 21 h whereupon the EtOH was removed in vacuo. After drying under vacuum to remove trace EtOH, the residue was acidified to pH ~2 with 1M aq. HCl. The water was removed in vacuo and the residue was purified by preparative HPLC (Column: Luna-AXIA C18 5 um 30×100 mm, Gradient Time: 10 min, Stop Time: 15 min, Start % B: 20%; Final % B: 100% Solvent B=90% MeOH-10% $H_2O$-0.1% $NH_4OAc$, Solvent A=10% MeOH-90% $H_2O$-0.1 $NH_4OAc$; Injection Volume: 2000 uL; Flowrate: 40 mL/min; Wavelength: 220 nm) to yield Example 23 (15.2 mg, 36%). $^1H$ NMR (500 MHz, DMSO-$d_6$) δ 11.06 (br. s., 1H), 8.12-7.74 (m, 2H), 7.05 (d, J=7.2 Hz, 1H), 6.91 (s, 2H), 6.61 (s, 1H), 6.51 (s, 1H), 6.41 (br. s., 1H), 6.29 (d, J=7.4 Hz, 1H), 3.83 (d, J=6.3 Hz, 1H), 3.47-3.12 (m, 4H), 2.67 (s, 4H), 2.60 (t, J=6.2 Hz, 2H), 2.53 (s, 6H), 2.20 (s, 3H), 1.75 (quin, J=5.8 Hz, 2H). HPLC retention time (Method #2): 1.608 min.; LCMS (ES): m/z 540.4 [M+H]$^+$. Human αVβ6 IC50 (nM)=1.02; Human αVβ3 IC50 (nM)=5.36; Human αVβ5 IC50 (nM)=0.54; and Human αVβ8 IC50 (nM)=9.06.

Example 24

Following the procedure described in Example 23, 23-2A (30 mg, 0.050 mmol) and 1M aq. NaOH (0.174 mL, 0.174 mmol) in EtOH (0.904 mL) yielded Example 24 (7.4 mg, 26%) as a mixture of diastereomers. $^1H$ NMR (500 MHz, DMSO-$d_6$) δ 11.08 (br. s., 1H), 7.88 (d, J=5.2 Hz, 2H), 7.74 (d, J=4.7 Hz, 1H), 7.14 (d, J=6.6 Hz, 1H), 6.92 (s, 2H), 6.67 (s, 1H), 6.51 (br. s., 1H), 6.44-6.37 (m, 1H), 6.32 (br. s., 1H), 3.80 (br. s., 1H), 3.44-3.35 (m, 5H), 2.73-2.60 (m, 2H), 2.54 (s, 6H), 2.21 (s, 3H), 1.92-1.85 (m, 1H), 1.82-1.71 (m, 1H), 1.67-1.56 (m, 1H), 1.51 (dd, J=13.1, 7.8 Hz, 1H). HPLC retention time (Method #2): 1.635 min.; LCMS (ES): m/z 540.4 [M+H]$^+$. Human αVβ6 IC50 (nM)=0.61; Human αVβ1 IC50 (nM)=3.03; Human αVβ3 IC50 (nM)=2.00; Human αVβ5 IC50 (nM)=0.23; and Human αVβ8 IC50 (nM)=11.87.

Example 25

(S)-2-(((Benzyloxy)carbonyl)amino)-3-(4-(2-(5,6,7,8-tetrahydro-1,8-naphthyridin-2-yl)ethyl)-1H-pyrrole-2-carboxamido)propanoic Acid, TFA

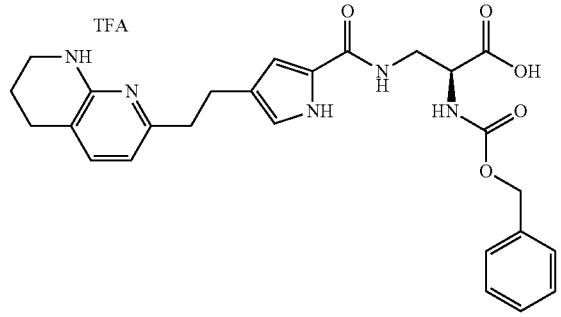

Example 25

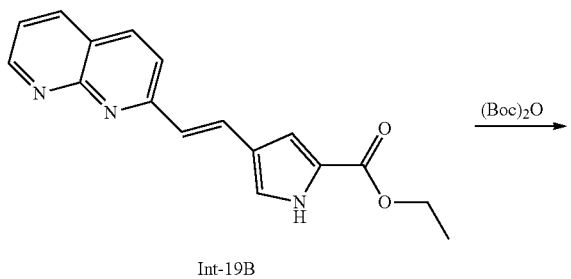

Int-19B

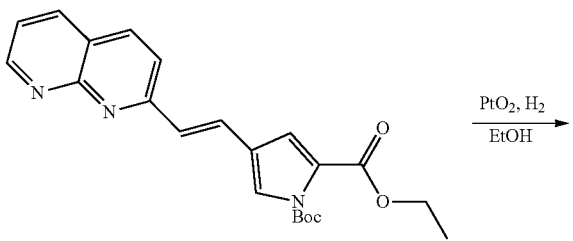

25A

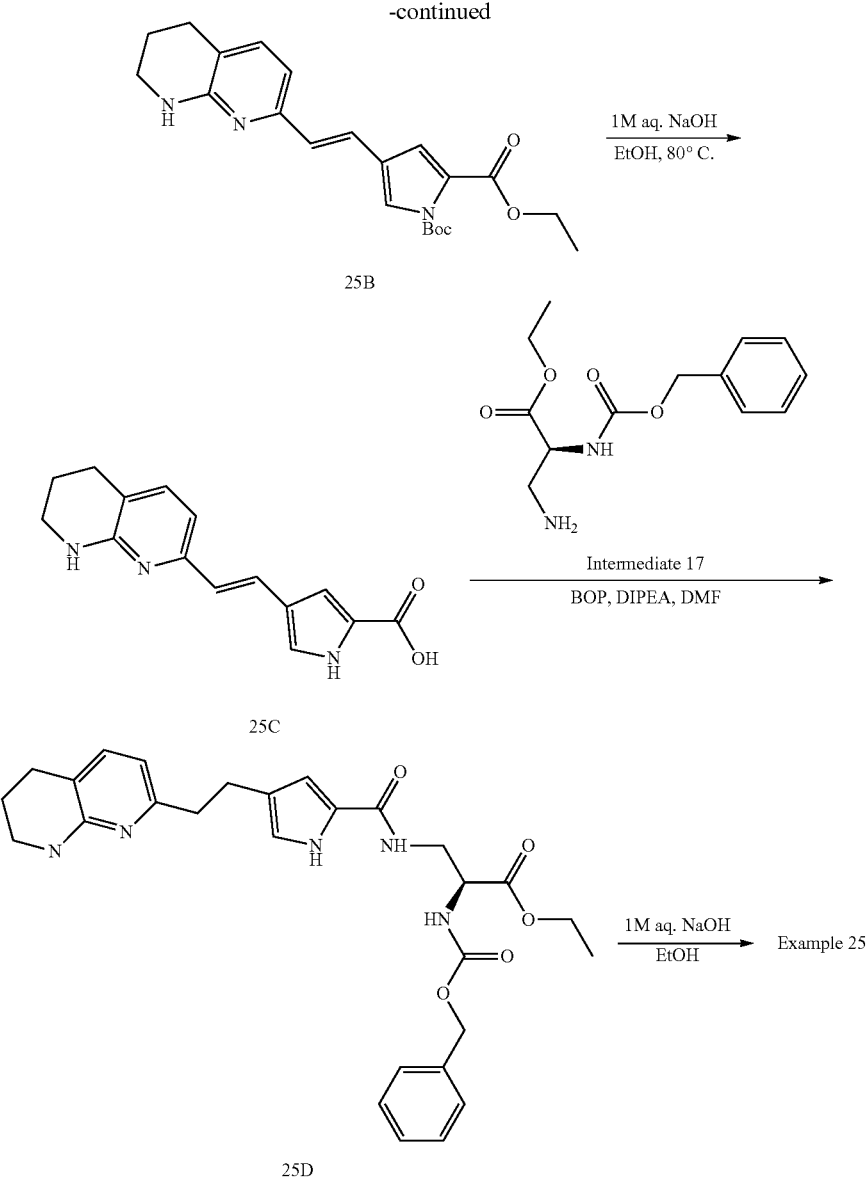

25A. 1-(tert-Butyl) 2-ethyl (E)-4-(2-(1,8-naphthyridin-2-yl)vinyl)-1H-pyrrole-1,2-dicarboxylate: To a solution of Int-19B (2.50 g, 8.52 mmol) in ACN (17.2 mL) were added DMAP (0.104 g, 0.852 mmol) and Boc₂O (2.42 g, 11.1 mmol). The reaction mixture was stirred at room temperature for 2 h then quenched with sat. NH₄Cl and diluted with EtOAc (50 mL). The organic layer was separated and washed with sat. NaHCO₃, water and sat. brine. The organic layer was then dried over anhydrous Na₂SO₄ concentrated in vacuo, and the residue was purified by flash chromatography (silica gel, DCM:EtOAc, 100:0 to 50:50) to yield 25A (2.40 g, 72%) as a light green solid. $^1$H NMR (500 MHz, CDCl₃) δ 9.09 (dd, J=4.1, 1.9 Hz, 1H), 8.18-8.07 (m, 2H), 7.84 (d, J=16.0 Hz, 1H), 7.57 (d, J=8.3 Hz, 1H), 7.51 (d, J=1.7 Hz, 1H), 7.42 (dd, J=8.1, 4.3 Hz, 1H), 7.18-7.06 (m, 2H), 4.35 (q, J=7.0 Hz, 2H), 1.61 (s, 9H), 1.39 (t, J=7.2 Hz, 3H). HPLC retention time (Method #2): 1.973 min.; LCMS (ES): m/z 394.2 [M+H]⁺.

25B. 1-(tert-Butyl) 2-ethyl 4-(2-(5,6,7,8-tetrahydro-1,8-naphthyridin-2-yl)ethyl)-1H-pyrrole-1,2-dicarboxylate: To a solution of 25A (2.40 g, 6.10 mmol) in EtOH (81 mL) was added PtO₂ (0.277 g, 1.22 mmol). The suspension was hydrogenated (1 atm H₂, balloon) at room temperature for 3.5 h. After filtration of the reaction mixture through a CELITE® pad and subsequent washing of the cake with EtOH, the filtrate was concentrated in vacuo. The residue was purified by flash chromatography (silica gel, DCM:MeOH, 100:0 to 95:5) to yield 25B (1.46 g, 60%) as an orange oil. $^1$H NMR (500 MHz, CDCl₃) δ 7.09 (d, J=1.7 Hz, 1H), 7.06 (d, J=7.4 Hz, 1H), 6.72 (d, J=1.9 Hz, 1H), 6.34 (d, J=7.2 Hz, 1H), 4.78 (br. s., 1H), 4.29 (q, J=7.2 Hz, 2H), 3.46-3.37 (m, 2H), 2.81-2.74 (m, 4H), 2.70 (t, J=6.3 Hz, 2H), 1.92 (quin, J=6.0 Hz, 2H), 1.57 (s, 9H), 1.35 (t, J=7.2 Hz, 3H). HPLC retention time (Method #2): 2.080 min.; LCMS (ES): m/z 400.3 [M+H]⁺.

25C. 4-(2-(5,6,7,8-Tetrahydro-1,8-naphthyridin-2-yl)ethyl)-1H-pyrrole-2-carboxylic acid, HCl: A solution of NaOH (1.50 g, 37.5 mmol) in water (2.78 mL) was added dropwise to a solution of 25B (5.00 g, 12.5 mmol) in EtOH (52.8 mL). The reaction mixture was stirred at 80° C. for 2 h whereupon the EtOH was removed in vacuo. After air drying under vacuum to remove trace EtOH, the residue was acidified to pH ~6 with 1M HCl. The precipitate was collected by filtration, washed with water and air-dried under vacuum. This material was dissolved in 4M HCl in Dioxane (2 mL) and stirred at room temperature for 5 min. The solvent was removed in vacuo and the residue was air-dried under vacuum to yield the HCl salt of 25C (2.03 g, 53%) as a crude orange solid. The filtrate was concentrated in vacuo and then purified by reverse phase ISCO chromatography (50 g column—HPC 18 Aq silica gel cartridge, 24 min. run) and eluted with a gradient from 10% ACN/H$_2$O/TFA (5%/95%/0.05%) to 100% ACN/H$_2$O/TFA (95%.5%/0.05%) to yield additional 25C (0.679 mg, 14%) as the TFA salt. $^1$H NMR (500 MHz, CD$_3$OD) δ 7.09 (d, J=7.4 Hz, 1H), 6.57-6.51 (m, 2H), 6.34 (d, J=7.4 Hz, 1H), 3.40-3.34 (m, 2H), 2.74 (s, 4H), 2.68 (t, J=6.3 Hz, 2H), 1.96-1.79 (m, 2H). HPLC retention time (Method #2): 0.930 min.; LCMS (ES): m/z 272.1 [M+H]$^+$.

25D. Ethyl (S)-2-(((benzyloxy)carbonyl)amino)-3-(4-(2-(5,6,7,8-tetrahydro-1,8-naphthyridin-2-yl)ethyl)-1H-pyrrole-2-carboxamido)propanoate, TFA: To a solution of 25C (HCl salt) (0.750 g, 2.44 mmol) and Intermediate 17 (0.738 g, 2.44 mmol) in DMF (4.65 mL) were added BOP (1.62 g, 3.66 mmol) and DIPEA (2.13 mL, 12.2 mmol). The reaction mixture was stirred at room temperature overnight whereupon it was diluted with water and extracted with EtOAc (3×). The combined organic phases were with washed water, sat. brine, dried over anhydrous Na$_2$SO$_4$ and concentrated. The residue was purified by flash chromatography (silica gel, DCM:MeOH, 100:0 to 90:10) to yield 25D (1.1 g, 87%) as an off-white solid. $^1$H NMR (500 MHz, DMSO-d$_6$) δ 11.16 (br. s., 1H), 7.97 (t, J=6.1 Hz, 1H), 7.70 (d, J=7.7 Hz, 1H), 7.41-7.20 (m, 5H), 7.06 (d, J=7.2 Hz, 1H), 6.64 (s, 1H), 6.59 (d, J=1.9 Hz, 1H), 6.35 (br. s., 1H), 6.29 (d, J=7.4 Hz, 1H), 5.05 (s, 2H), 4.23 (d, J=7.4 Hz, 1H), 4.07 (q, J=7.2 Hz, 2H), 3.60-3.51 (m, 2H), 3.25 (br. s., 2H), 2.69 (s, 4H), 2.62 (t, J=6.1 Hz, 2H), 1.78-1.71 (m, 2H), 1.13 (t, J=7.0 Hz, 3H). HPLC retention time (Method #2): 1.815 min.; LCMS (ES): m/z 520.3 [M+H]$^+$. Example 25: 1M aq. NaOH (0.202 mL, 0.202 mmol) was added to a solution of 25D (0.030 g, 0.058 mmol) in EtOH (1.05 mL) and the reaction mixture was stirred at room temperature for 1 h. The EtOH was removed in vacuo and air drying under vacuum to remove trace EtOH. The residue was dissolved in ACN, acidified with 1M aq. HCl and then reconcentrated in vacuo. The residue was purified by preparative HPLC (Phenomenex Luna AXIA 5u C18 21.2×100 mm, 10 min gradient, 15 min run, 5% to 100% Solvent B=90% MeOH-10% H$_2$O-0.1% TFA, Solvent A=10% MeOH-90% H$_2$O-0.1% TFA) to yield Example 25 (25 mg, 71%). $^1$H NMR (500 MHz, DMSO-d$_6$) δ 12.70 (br. s., 1H), 11.25 (br. s., 1H), 7.99 (t, J=5.9 Hz, 1H), 7.85 (br. s., 1H), 7.58 (dd, J=10.7, 7.7 Hz, 2H), 7.39-7.24 (m, 5H), 6.69 (br. s., 1H), 6.63-6.55 (m, 2H), 5.02 (s, 2H), 4.22-4.12 (m, 1H), 3.66-3.46 (m, 2H), 3.40 (br. s., 2H), 2.94-2.84 (m, 2H), 2.80-2.65 (m, 4H), 1.88-1.74 (m, 2H). HPLC retention time (Method #2): 1.423 min.; LCMS (ES): m/z 492.3 [M+H]$^+$. Human αVβ6 IC50 (nM)=0.34; Human αVβ3 IC50 (nM)=1.50; Human αVβ5 IC50 (nM)=0.16; and Human αVβ8 IC50 (nM)=12.60.

Example 26

(S)-2-((((Cyclopentyloxy)carbonyl)amino)-3-(4-(2-(5,6,7,8-tetrahydro-1,8-naphthyridin-2-yl)ethyl)-1H-pyrrole-2-carboxamido)propanoic Acid

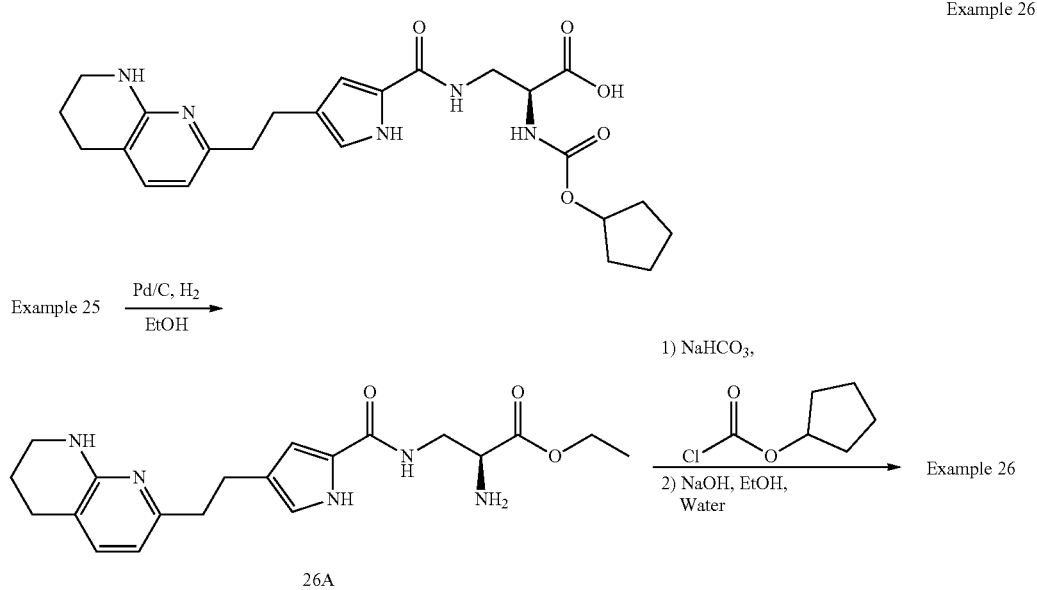

Example 26

26A. Ethyl (S)-2-amino-3-(4-(2-(5,6,7,8-tetrahydro-1,8-naphthyridin-2-yl)ethyl)-1H-pyrrole-2-carboxamido)propanoate, 3 TFA: To a solution of Example 25 (60.6 mg, 0.117 mmol) in EtOH (3.53 mL) were added TFA (0.468 mmol, 36 uL) and Pd/C (12.4 mg, 0.012 mmol). The suspension was hydrogenated (1 atm, H$_2$, balloon) at room temperature for 8 h. After filtration of the reaction mixture through a CELITE® pad and subsequent washing of the cake with EtOH, the filtrate was concentrated and dried under vacuum to yield 26A (59.4 mg, 72%) as a yellow oil. $^1$H NMR (500 MHz, CD$_3$OD) δ 10.87 (br. s., 1H), 7.54 (d, J=7.4 Hz, 1H), 6.78 (s, 1H), 6.68 (s, 1H), 6.55 (d, J=7.4 Hz, 1H), 4.38-4.26 (m, 2H), 4.22 (dd, J=5.9, 4.3 Hz, 1H), 3.91-3.85 (m, 1H), 3.81-3.75 (m, 1H), 3.54-3.43 (m, 2H), 2.94 (d, J=7.7 Hz, 2H), 2.90-2.83 (m, 2H), 2.80 (t, J=6.2 Hz, 2H), 2.05-1.90 (m, 2H), 1.30 (t, J=7.2 Hz, 3H). HPLC retention time (Method #2): 0.775 min.; LCMS (ES): m/z 386.3 [M+H]+.

Example 26

To a mixture of 26A (15 mg, 0.039 mmol) and NaHCO$_3$ (8.17 mg, 0.097 mmol) in THF (1.37 mL) and H$_2$O (0.683 mL) was added cyclopentyl carbonochloridate (6.94 mg, 0.047 mmol). The reaction mixture was stirred at room temperature for 21 h. The solvent was removed in vacuo and the residue was dissolved in EtOH (1.37 mL) and 1M aq. NaOH (0.136 mL, 0.136 mmol) was added. The reaction mixture was stirred at room temperature overnight at which point the solvent was removed in vacuo and the residue was purified preparative HPLC (Column: XBridge C18, 19×200 mm, 5-µm particles; Mobile Phase A: 5:95 acetonitrile: water with 10 mM ammonium acetate; Mobile Phase B: 95:5 acetonitrile: water with 10 mM ammonium acetate; Gradient: 13-43% B over 25 minutes, then a 4-minute hold at 43% B; Flow: 20 mL/min.) to yield Example 26 (5 mg, 26%). $^1$H NMR (500 MHz, DMSO-d$_6$) δ 11.14 (br. s., 1H), 7.95 (br. s., 1H), 7.21 (br. s., 1H), 7.02 (d, J=7.2 Hz, 1H), 6.64 (s, 1H), 6.60 (s, 1H), 6.34-6.22 (m, 2H), 4.94 (dt, J=5.9, 3.0 Hz, 1H), 4.10 (d, J=5.8 Hz, 1H), 4.03 (br. s., 1H), 3.56-3.44 (m, 2H), 3.24 (br. s., 2H), 2.74-2.63 (m, 4H), 2.61 (t, J=6.3 Hz, 2H), 1.79-1.73 (m, 3H), 1.66-1.49 (m, 6H). LCMS (ES): m/z 470.3 [M+H]+. Human αVβ6 IC50 (nM)=0.28; Human αVβ3 IC50 (nM)=1.67; Human αVβ5 IC50 (nM)=0.09; and Human αVβ8 IC50 (nM)=8.78.

Biological Evaluation

All binding assays used the HTRF (homogeneous time resolved fluorescence) technology from Cisbio International, therefore all assays are described as HTRF binding assays. The assay results for the Examples are listed above together with the characterization data. The HTRF binding assays are established for the following integrins: human αVβ6, human αVβ1, human αVβ3, human αVβ5, and human αVβ8. All assays used the following assay buffer: 20 mM Tris, pH 7.4, 1 mM MgCl$_2$, 1 mM MnCl$_2$, 0.01% Tween 20, and 0.01% BSA. Alternatively, a SPA-based assay was used for evaluation of receptor binding.

The following describes the components and a representative procedure for the human αVβ6 HTRF binding assay: Recombinant human αVβ6 Integrin (R & D systems, 3817-AV) was biotinylated. Biotinylated human αVβ6 Integrin was added to assay vessel at a final concentration of 1.25 nM. FITC-conjugated fibronectin (Cytoskeleton, FNR02) was then added at the final concentration of 5 nM. The mixture was centrifuged at 600 rpm for three minutes using Thermo Fisher Heraeus Multifuge X3 centrifuge and then incubated at RT for an hour. Streptavidin Terbium (Cisbio international 610STLB) was then added at the final concentration of 0.625 nM. The resulting mixture was centrifuged at 600 rpm for three minutes using Thermo Fisher Heraeus Multifuge X3 centrifuge and then incubated at room temperature overnight in dark before reading HTRF signals.

The SPA-based assay was carried out according to the protocol and procedures similar to the ones described in the following reference with appropriate modifications to agents and ligands which are readily understood by one skilled in the art: Pachter J A, Zhang R, Mayer-Ezell R., "Scintillation proximity assay to measure binding of soluble fibronectin to antibody-captured αVβ1 integrin" Anal Biochem. 1995 Sep. 1; 230(1):101-7.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (I):

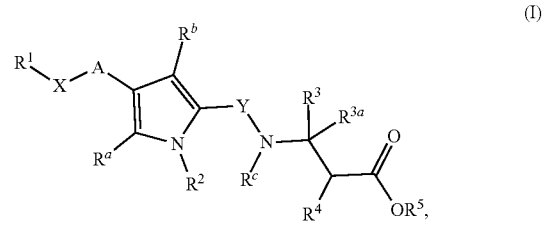

wherein:

A is a covalent bond, O, S, NH, —O—(C$_{1-3}$ alkylene)-, —S—(C$_{1-3}$ alkylene)-, or —NH—(C$_{1-3}$ alkylene)-, wherein the C$_{1-3}$ alkylene is each independently substituted with 0, 1, or 2 R$^{7a}$;

X is absent or a C$_{1-5}$ linear alkylene substituted with 0, 1, 2, or 3 R$^{7b}$;

Y is C(O) or C(R$^{6a}$R$^{6b}$);

L$^1$ and L$^2$ are each independently C$_{1-4}$ alkylene;

n is an integer of 1 or 2;

r is an integer of 0, 1, 2, or 3;

R$^1$ is an Arginine mimetic moiety selected from the group consisting of

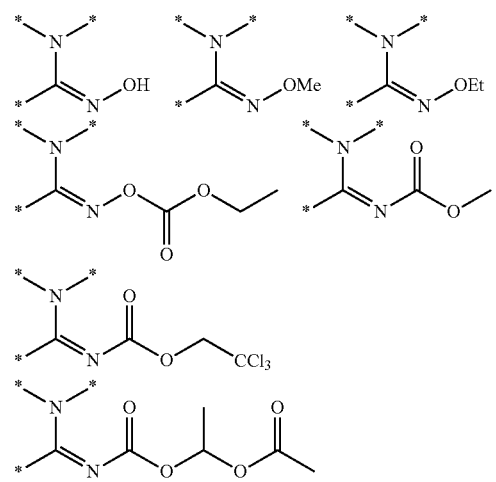

-continued

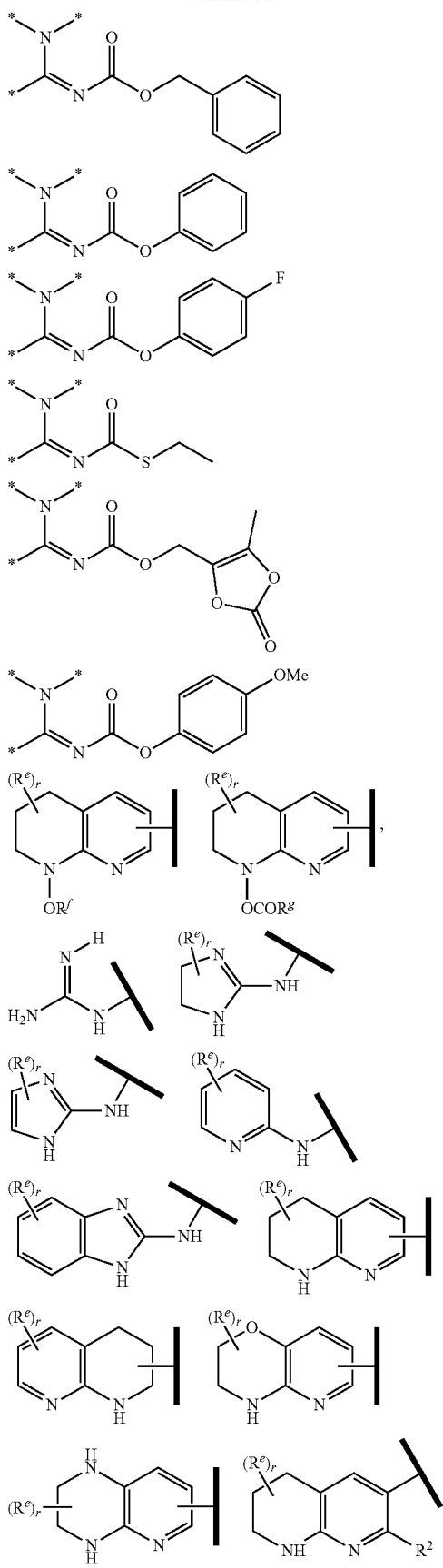

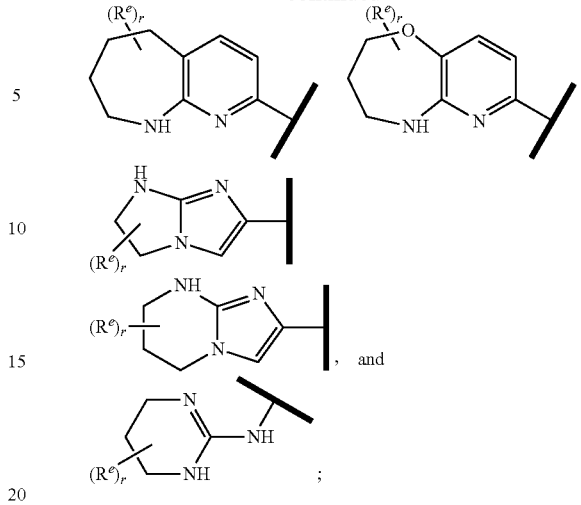

one of the asterisks in each of the arginine mimetics moiety is an attachment point to X and the other two asterisks are hydrogen;

$R^2$ is hydrogen or $C_{1-6}$ alkyl;

$R^3$ is hydrogen, $C_{1-6}$ alkyl, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$;

$R^{3a}$ is hydrogen; or alternatively, $R^{3a}$ and $R^3$, together with the atom or atoms to which they are attached, form a 3- to 6-membered carbocyclic or heterocyclic ring which is optionally substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^4$ is hydrogen, $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^9$;

$R^5$ is hydrogen, $R^{5a}$, or a structural moiety selected from

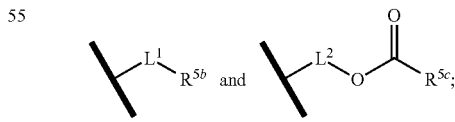

$R^{5a}$ and $R^{5b}$ are each independently $C_{1-6}$ alkyl, phenyl, benzyl, or 5- to 7-membered heterocyclyl; wherein the alkyl, phenyl, and heterocyclyl are each independently substituted with 0 to 3 $R^{5d}$;

$R^{5c}$ is $C_{1-6}$ alkyl or 5- to 7-membered carbocyclyl; wherein the alkyl and heterocyclyl are each independently substituted with 0 to 3 $R^{5d}$;

$R^{5d}$, at each occurrence, is independently halo, OH, alkoxy, oxo, or alkyl; or alternatively, two adjacent $R^{5d}$, together with the atoms to which they are attached, form a carbocyclyl moiety;

$R^{6a}$ and $R^{6b}$ are each independently hydrogen or $C_{1-6}$ alkyl;

$R^{7a}$ and $R^{7b}$ are each independently halo, cyano, hydroxyl, amino, $C_{1-6}$ alkyl, haloalkyl, hydroxyalkyl, aminoalkyl, alkoxy, haloalkoxy, amido, carbamate, or sulfonamide;

$R^8$ at each occurrence is independently halo, cyano, OH, $NR^aR^b$, $C_{1-6}$ alkyl, alkoxy, alkylamino, haloalkyl, haloalkoxy, haloaminoalkyl, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^8$ at adjacent positions, together with the atoms to which they are attached, form a carbocyclyl or heterocyclyl; wherein the aryl and heteroaryl are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^9$ at each occurrence is independently halo, cyano, OH, $NR^aR^b$, $C_{1-6}$ alkyl, alkoxy, alkylamino, haloalkyl, haloalkoxy, haloaminoalkyl, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^9$ at adjacent positions, together with the atoms to which they are attached, form a carbocyclyl or heterocyclyl; wherein the aryl and heteroaryl are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{10}$ is $C_{1-6}$ alkyl, 3- to 10-membered carbocyclyl, 3- to 10-membered heterocyclyl, 6- to 10-membered aryl, or 5- to 10-membered heteroaryl; wherein the alkyl, carbocyclyl, and heterocyclyl are each independently substituted with 0, 1, 2, or 3 $R^{11}$;

$R^{11}$ is halo, cyano, hydroxyl, amino, amino, amido, carbamate, sulfonamide, $C_{1-6}$ alkyl, alkoxy, 3- to 10-membered carbocyclyl, 3- to 10-membered heterocyclyl, 6- to 10-membered aryl, or 5- to 10-membered heteroaryl; wherein the aryl, alkyl, and heteroaryl are each independently substituted with 0, 1, 2, or 3 $R^{12}$;

$R^{12}$ and $R^{13}$, at each occurrence, are independently halo, cyano, OH, amino, $C_{1-6}$ alkyl, alkoxy, alkylamino, haloalkyl, haloalkoxy, haloaminoalkyl, 3 to 6 membered carbocyclyl, 3 to 6 membered heterocyclyl, 6- to 10-membered aryl, or 5- to 10-membered heteroaryl; wherein the aryl and heteroaryl are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^a$, $R^b$, and $R^c$, at each occurrence, are independently hydrogen, $C_{1-10}$ alkyl, 3- to 10-membered carbocyclyl, or 3- to 10-membered heterocyclyl; wherein the alkyl, carbocyclyl, heterocyclyl are each independently substituted with 0, 1, 2, or 3 $R^{13}$;

$R^e$ is OH, amino, amido, carbamate, sulfonamide, $C_{1-4}$ alkyl, halo, $C_{1-4}$ haloalkyl, or $C_{3-6}$ cycloalkyl;

$R^f$ is hydrogen, $CH_3$, $CH_2CH_3$, or $C(O)OCH_2CH_3$; and $R^g$ is $CH_3$, $CH_2CH_3$, $CH_2CCl_3$, phenyl, 4-fluorophenyl, 4-methoxyphenyl, benzyl,

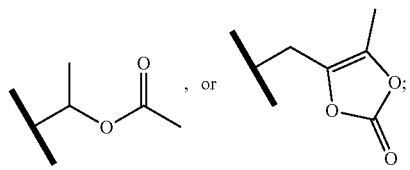

or a pharmaceutically acceptable salt thereof.

2. The compound of claim 1 or a pharmaceutically acceptable salt thereof, wherein Y is C(O).

3. The compound of claim 1 or a pharmaceutically acceptable salt thereof, wherein X is $C_{2-4}$ linear alkylene.

4. The compound of claim 1 or a pharmaceutically acceptable salt thereof, wherein $R^1$ is selected from the group consisting of

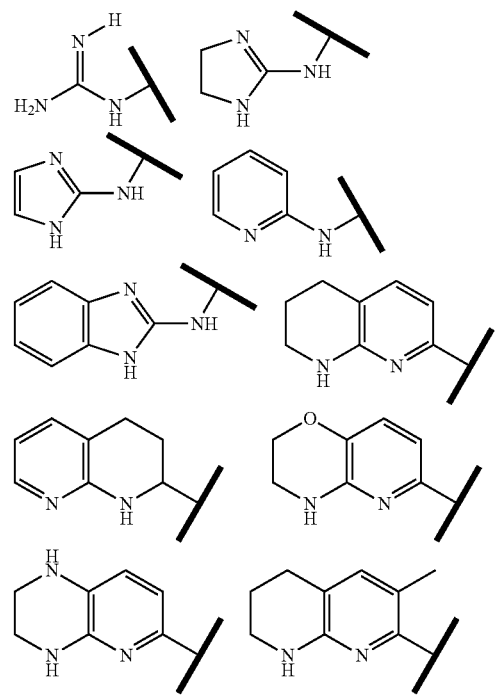

-continued

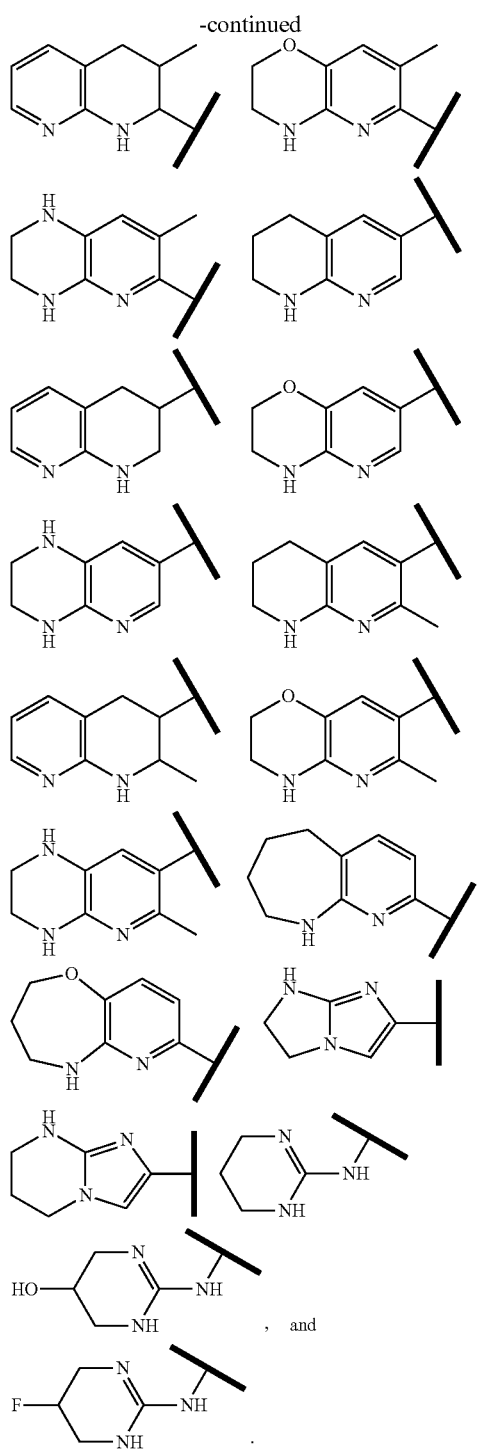

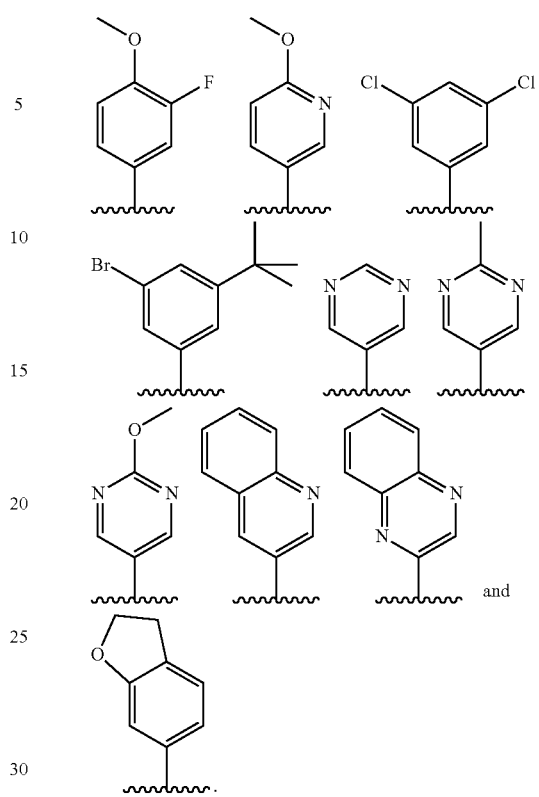

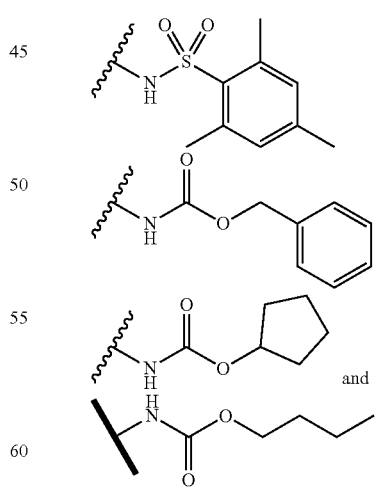

5. The compound of claim 1 or a pharmaceutically acceptable salt thereof, wherein $R^4$ is hydrogen; and $R^3$ is 3- to 10-membered carbocyclyl, 6- to 10-membered aryl, 3- to 14-membered heterocyclyl, or 5- to 14-membered heteroaryl, wherein the carbocyclyl, heterocyclyl, aryl, and heteroaryl are each independently substituted with 0, 1, 2, or 3 $R^8$.

6. The compound of claim 1 or a pharmaceutically acceptable salt thereof, wherein $R^3$ is selected from hydrogen, 7. The compound of claim 1 or a pharmaceutically acceptable salt thereof, wherein $R^3$ is hydrogen; and $R^4$ is $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$.

8. The compound of claim 1 or a pharmaceutically acceptable salt thereof, wherein $R^4$ is selected from hydrogen and the following structural moieties:

9. The compound of claim 1 or a pharmaceutically acceptable salt thereof, wherein $R^5$ is hydrogen or $R^{5a}$; and $R^{5a}$ is methyl, ethyl, isopropyl, n-butyl, isopentyl, or a structural moiety selected from

101

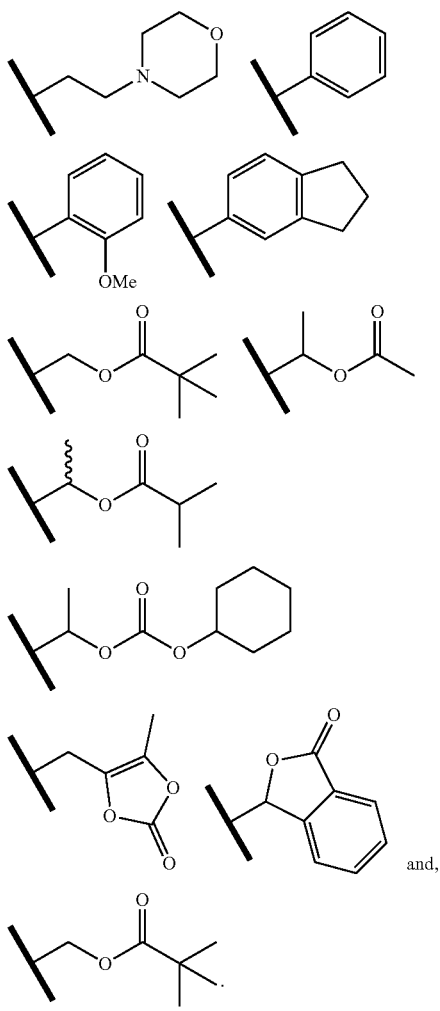

and,

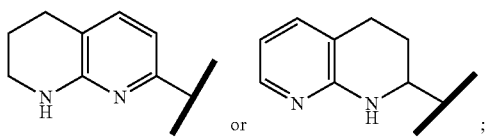

10. The compound of claim 1 or a pharmaceutically acceptable salt thereof, wherein $R^2$ is hydrogen; and $R^5$ is hydrogen.

11. A pharmaceutical composition comprising a compound of claim 1, or a pharmaceutically acceptable salt thereof, and a pharmaceutically acceptable carrier.

12. The compound of claim 1 or a pharmaceutically acceptable salt thereof, wherein:
A is a covalent bond;
X is absent or a $C_{2-3}$ linear alkylene;
Y is C(O);
$R^1$ is:

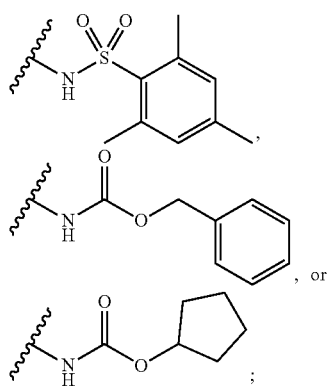

102

$R^2$ is hydrogen or $C_{1-2}$ alkyl;
$R^3$ is:

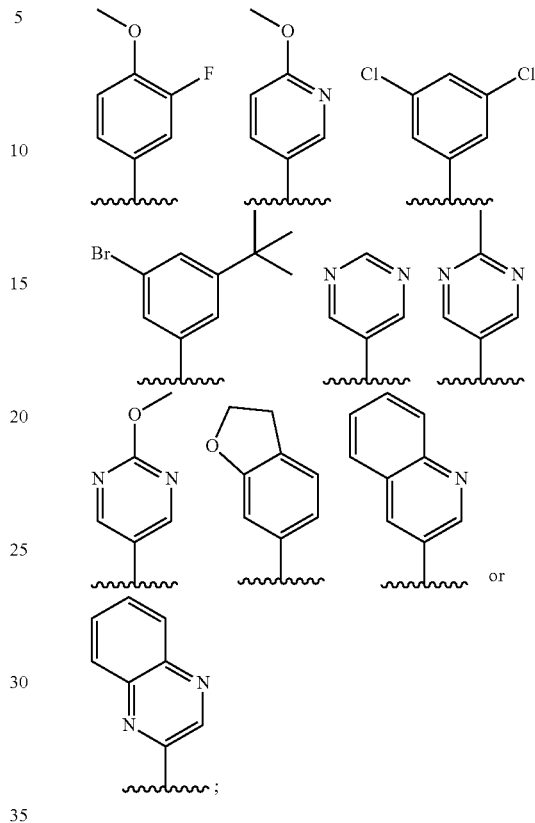

$R^{3a}$ is hydrogen;
$R^4$ is hydrogen, $R^a$ is hydrogen or methyl;
$R^b$ is hydrogen;
$R^c$ is hydrogen; and
$R^5$ is hydrogen.

13. The compound of claim 1 or a pharmaceutically acceptable salt thereof, wherein:
A is a covalent bond;
X is absent or a $C_{2-3}$ linear alkylene;
Y is C(O);
$R^1$ is;

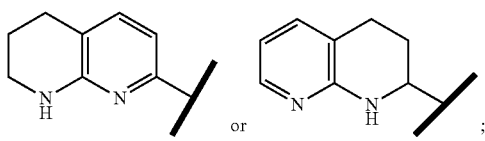

R² is hydrogen or C₁₋₂ alkyl;
R³ is hydrogen,

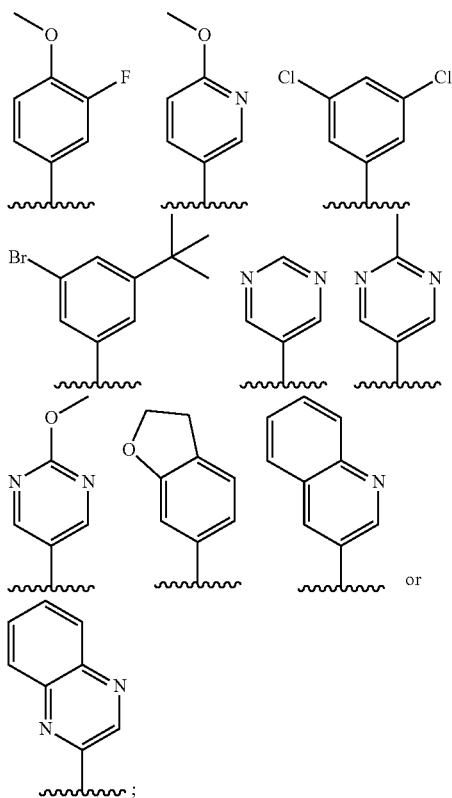

R³ᵃ is hydrogen;
R⁴ is hydrogen;
Rᵃ is hydrogen or methyl;
Rᵇ is hydrogen;
Rᶜ is hydrogen; and
R⁵ is hydrogen.

14. The compound of claim 1 or a pharmaceutically acceptable salt thereof, wherein:
A is a covalent bond;
X is a C₂ linear alkylene;
Y is C(O);
R¹ is

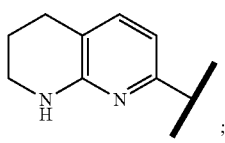

R² is hydrogen;
R³ is hydrogen;
R⁴ is

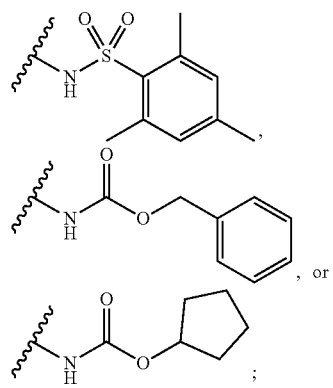

Rᵃ is hydrogen;
Rᵇ is hydrogen;
Rᶜ is hydrogen; and
R⁵ is hydrogen.

15. The compound of claim 1 or a pharmaceutically acceptable salt thereof, wherein said compound is:
(S)-3-(3-fluoro-4-methoxyphenyl)-3-(4-(2-(5,6,7,8-tetrahydro-1,8-naphthyridin-2-yl)ethyl)-1H-pyrrole-2-carboxamido)propanoic acid (1-2);
(R)-3-(3-fluoro-4-methoxyphenyl)-3-(4-(2-(5,6,7,8-tetrahydro-1,8-naphthyridin-2-yl)ethyl)-1H-pyrrole-2-carboxamido)propanoic acid (3);
(S)-3-(3-fluoro-4-methoxyphenyl)-3-(1-methyl-4-(2-(5,6,7,8-tetrahydro-1,8-naphthyridin-2-yl)ethyl)-1H-pyrrole-2-carboxamido)propanoic acid (4);
ethyl (S)-3-(1-ethyl-4-(2-(5,6,7,8-tetrahydro-1,8-naphthyridin-2-yl)ethyl)-1H-pyrrole-2-carboxamido)-3-(3-fluoro-4-methoxyphenyl)propanoate (5);
(S)-3-(3-fluoro-4-methoxyphenyl)-3-(5-methyl-4-(2-(5,6,7,8-tetrahydro-1,8-naphthyridin-2-yl)ethyl)-1H-pyrrole-2-carboxamido)propanoic acid (6);
(S)-3-(6-methoxypyridin-3-yl)-3-(4-(2-(5,6,7,8-tetrahydro-1,8-naphthyridin-2-yl)ethyl)-1H-pyrrole-2-carboxamido)propanoic acid (7);
(S)-3-(6-methoxypyridin-3-yl)-3-(1-methyl-4-(2-(5,6,7,8-tetrahydro-1,8-naphthyridin-2-yl)ethyl)-1H-pyrrole-2-carboxamido)propanoic acid (8);
ethyl (S)-3-(1-ethyl-4-(2-(5,6,7,8-tetrahydro-1,8-naphthyridin-2-yl)ethyl)-1H-pyrrole-2-carboxamido)-3-(6-methoxypyridin-3-yl)propanoate (9);
(S)-3-(6-ethoxypyridin-3-yl)-3-(5-methyl-4-(2-(5,6,7,8-tetrahydro-1,8-naphthyridin-2-yl)ethyl)-1H-pyrrole-2-carboxamido)propanoic acid (10);
(S)-3-(3,5-dichlorophenyl)-3-(4-(2-(5,6,7,8-tetrahydro-1,8-naphthyridin-2-yl)ethyl)-1H-pyrrole-2-carboxamido)propanoic acid (11);
(S)-3-(3-bromo-5-(tert-butyl)phenyl)-3-(4-(2-(5,6,7,8-tetrahydro-1,8-naphthyridin-2-yl)ethyl)-1H-pyrrole-2-carboxamido)propanoic acid (12);
3-(2-methylpyrimidin-5-yl)-3-(4-(2-(5,6,7,8-tetrahydro-1,8-naphthyridin-2-yl)ethyl)-1H-pyrrole-2-carboxamido)propanoic acid (13);
3-(2-methoxypyrimidin-5-yl)-3-(4-(2-(5,6,7,8-tetrahydro-1,8-naphthyridin-2-yl)ethyl)-1H-pyrrole-2-carboxamido)propanoic acid (14);
3-(pyrimidin-5-yl)-3-(4-(2-(5,6,7,8-tetrahydro-1,8-naphthyridin-2-yl)ethyl)-1H-pyrrole-2-carboxamido)propanoic acid (15);

(S)-3-(quinolin-3-yl)-3-(4-(2-(5,6,7,8-tetrahydro-1,8-naphthyridin-2-yl)ethyl)-1H-pyrrole-2-carboxamido)propanoic acid (16);

(S)-3-(2,3-dihydrobenzofuran-6-yl)-3-(4-(2-(5,6,7,8-tetrahydro-1,8-naphthyridin-2-yl)ethyl)-1H-pyrrole-2-carboxamido)propanoic acid (17);

3-(quinoxalin-2-yl)-3-(4-(2-(5,6,7,8-tetrahydro-1,8-naphthyridin-2-yl)ethyl)-1H-pyrrole-2-carboxamido)propanoic acid (18);

(S)-3-(3-fluoro-4-methoxyphenyl)-3-(4-(5,6,7,8-tetrahydro-1,8-naphthyridin-2-yl)-1H-pyrrole-2-carboxamido)propanoic acid (19);

(S)-3-(6-methoxypyridin-3-yl)-3-(4-(3-(5,6,7,8-tetrahydro-1,8-naphthyridin-2-yl)propyl)-1H-pyrrole-2-carboxamido)propanoic acid, 2 TFA (20);

(S)-3-(2-methylpyrimidin-5-yl)-3-(4-(3-(5,6,7,8-tetrahydro-1,8-naphthyridin-2-yl)propyl)-1H-pyrrole-2-carboxamido)propanoic acid, TFA (21);

(S)-3-(2-methoxypyrimidin-5-yl)-3-(4-(3-(5,6,7,8-tetrahydro-1,8-naphthyridin-2-yl)propyl)-1H-pyrrole-2-carboxamido)propanoic acid (22);

(S)-3-(4-(2-(5,6,7,8-Tetrahydro-1,8-naphthyridin-2-yl)ethyl)-1H-pyrrole-2-carboxamido)-2-((2,4,6-trimethylphenyl)sulfonamido)propanoic acid (23);

(2S)-3-(4-(2-(1,2,3,4-Tetrahydro-1,8-naphthyridin-2-yl)ethyl)-1H-pyrrole-2-carboxamido)-2-((2,4,6-trimethylphenyl)sulfonamido)propanoic acid (24);

(S)-2-(((benzyloxy)carbonyl)amino)-3-(4-(2-(5,6,7,8-tetrahydro-1,8-naphthyridin-2-yl)ethyl)-1H-pyrrole-2-carboxamido)propanoic acid, TFA (25); or (S)-2-(((cyclopentyloxy)carbonyl)amino)-3-(4-(2-(5,6,7,8-tetrahydro-1,8-naphthyridin-2-yl)ethyl)-1H-pyrrole-2-carboxamido)propanoic acid (26).

* * * * *

UNITED STATES PATENT AND TRADEMARK OFFICE
CERTIFICATE OF CORRECTION

PATENT NO. : 10,717,736 B2
APPLICATION NO. : 16/347826
DATED : July 21, 2020
INVENTOR(S) : Guohua Zhao et al.

Page 1 of 1

It is certified that error appears in the above-identified patent and that said Letters Patent is hereby corrected as shown below:

On the Title Page

Column 2 (Abstract), Line 12 (Approx.), delete "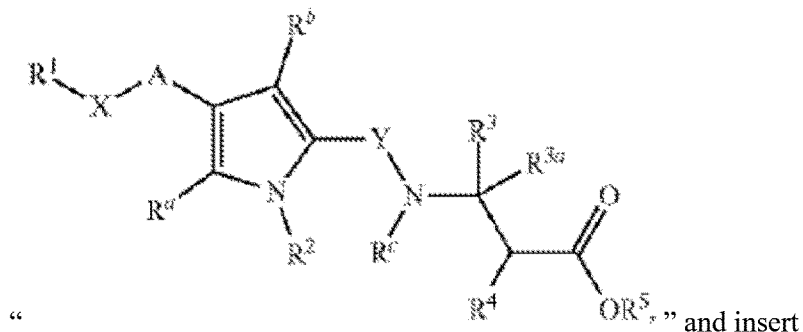," and insert

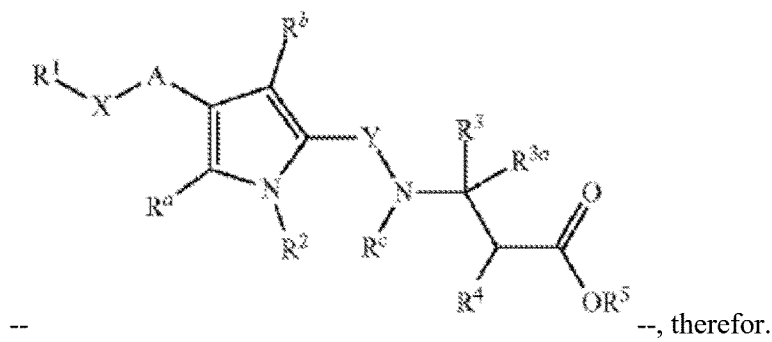

--, therefor.

In the Claims

In Claim 1, Column 97, Line 54, delete "amino, amino," and insert -- amino, --, therefor.

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*